US012807953B1

(12) United States Patent
Picher et al.

(10) Patent No.: US 12,807,953 B1
(45) **Date of Patent: *Nov. 24, 2026**

(54) LINEAR DNA PRODUCTS

(71) Applicants: 4Basebio, S.L.U., Madrid (ES); 4Basebio UK LTD, Cambridge (GB)

(72) Inventors: Ángel Picher, Madrid (ES); Heikki Lanckriet, Cambridge (GB); Amy Walker, Cambridge (GB)

(73) Assignees: 4Basebio UK LTD, Cambridge (GB); 4Basebio, S.L.U., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 19/306,828

(22) Filed: Aug. 21, 2025

Related U.S. Application Data

(63) Continuation of application No. 18/261,083, filed as application No. PCT/EP2022/071413 on Jul. 29, 2022.

(30) Foreign Application Priority Data

Jul. 30, 2021 (EP) .................................... 21382725

(51) Int. Cl.
*C12N 15/85* (2006.01)
*A61K 38/00* (2006.01)
*A61K 39/00* (2006.01)
*A61K 48/00* (2006.01)
*C12N 9/22* (2006.01)
*C12N 15/113* (2010.01)

(52) U.S. Cl.
CPC ............ *C12N 15/113* (2013.01); *A61K 38/00* (2013.01); *A61K 39/00* (2013.01); *A61K 48/00* (2013.01); *C12N 9/226* (2025.05); *C12N 15/85* (2013.01); *C12N 2310/20* (2017.05); *C12N 2310/315* (2013.01); *C12N 2310/53* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 8,278,051 | B2 | 10/2012 | Rhee |
| 2011/0269193 | A1 | 11/2011 | Rhee et al. |
| 2012/0094847 | A1 | 4/2012 | Warthmann et al. |
| 2014/0295498 | A1 | 10/2014 | Turner et al. |
| 2014/0329282 | A1 | 11/2014 | Nelson et al. |
| 2017/0369889 | A1 | 12/2017 | Weber et al. |
| 2018/0291445 | A1 | 10/2018 | Betts et al. |
| 2019/0360043 | A1 | 11/2019 | Pham et al. |
| 2020/0080130 | A1 | 3/2020 | Dapprich et al. |
| 2020/0362403 | A1 | 11/2020 | Serantes et al. |
| 2021/0214780 | A1 | 7/2021 | Jiang |
| 2023/0048994 | A1* | 2/2023 | Smith .................... C12N 15/86 |

FOREIGN PATENT DOCUMENTS

| | | |
|---|---|---|
| EP | 3763823 | 1/2021 |
| EP | 3812472 | 4/2021 |
| EP | 4310182 | 1/2024 |
| WO | 2000046402 | 8/2000 |
| WO | WO 2010086626 | 8/2010 |
| WO | 2012012037 | 1/2012 |
| WO | 2016195598 | 12/2016 |
| WO | 2018031588 | 2/2018 |
| WO | 2019032102 | 2/2019 |
| WO | 2019053039 | 3/2019 |
| WO | 2020178759 | 9/2020 |
| WO | WO 2020218924 | 10/2020 |
| WO | WO 2021034275 | 2/2021 |
| WO | WO 2021152146 | 8/2021 |
| WO | WO 2021152147 | 8/2021 |
| WO | 2021252354 | 12/2021 |
| WO | WO 2022058755 | 3/2022 |
| WO | WO 2023006985 | 2/2023 |
| WO | 2024017978 | 1/2024 |

OTHER PUBLICATIONS

D'Amore et al. (2017) "SMRT Gate: A method for validation of synthetic constucts on Pacific Biosciences sequencing platforms" Biotechniques, 63:13-20.

Eckstein (2014) "Phosphorothioates, Essential Components of Therapeutic Oligonucleotides" Nucleic Acid Therapeutics, 24(6):374-387.

Engler et al. (2009) "Golden Gate Shuffling: A One-Pot DNA Shuffling Method Based on Type IIs Restriction Enzymes" PLoS ONE, 4(5):e5553, 9 pages.

Engler et al. (2008) "A One Pot, One Step, Precision Cloning Method with High Throughput Capability" PLoS ONE, 3(11):e3647, 7 pages.

Extended European Search Report dated Jan. 20, 2022, Appl. No. EP 21382725.6, 13 pp.

Intention to Grant along with the claims dated May 23, 2024, Appl. No. GB2317071.5, 6 pp.

International Preliminary Report on Patentability dated Oct. 30, 2023, Appl. No. PCT/EP2022/071413, 14 pp.

International Search Report dated Nov. 16, 2022, Appl. No. PCT/EP2022/071413, 13 pp.

(Continued)

*Primary Examiner* — Marcia S Noble
(74) *Attorney, Agent, or Firm* — Brian E. Davy; Bozicevic, Field & Francis LLP

(57) ABSTRACT

Methods for producing a linear deoxyribonucleic acid (DNA) product with enhanced resistance to nuclease digestion are provided. The methods comprise: (a) contacting a double-stranded DNA molecule with an endonuclease, a ligase and first and second adaptor molecules to form a single contiguous aqueous volume; and (b) incubating the single contiguous aqueous volume to generate a linear DNA product. There are also provided linear deoxyribonucleic acid (DNA) products with enhanced resistance to nuclease digestion and uses thereof.

17 Claims, 30 Drawing Sheets

Specification includes a Sequence Listing.

(56) References Cited

OTHER PUBLICATIONS

Karbowniczek et al. (2017) "Doggybone™ DNA: an advanced platform for AAV production" Cell and Gene Therapy Insights, 3(9):731-738.
Karda et al. (2019) "Production of lentiviral vectors using novel, enzymatically produced, linear DNA", Gene Therapy, 26(3):86-92.
Lee et al. (1996) "Sequential amplification of cloned DNA as tandem multimers using class-IIS restriction enzymes" Genetic Analysis: Biomolecular Engineering, 13:139-145.
Notice of Opposition (English Translation) dated May 23, 2025, Appln. No. ES202390123, 33 pages.
Office Action dated Jun. 12, 2024, Appl. No. ES 202390123, 5 pp.
Padgett et al. (1996) "Creating seamless junctions independent of restriction sites in PCR cloning" Gene, 168:31-35.
Potapov et al. (2018) "Comprehensive Profiling of Four Base Overhang Ligation Fidelity by T4 DNA Ligase and Application to DNA Assembly" ACS Synth. Biol., 7:2665-2674.
Pryor et al. (2020) "Enabling one-pot Golden Gate assemblies of unprecedented complexity using data-optimized assembly design" PLOS ONE, 15(9):e0238592.
Sanjana et al. (2013) "A Transcription Activator-Like Effector (TALE) Toolbox for Genome Engineering" Nat Protoc. 7(1):171-192.
Sambrook, J. and Russell, DW "Molecular Cloning: A Laboratory Manual", Chapter 9 "Preparation of Radiolabelled DNA and RNA probes", Chapter 13 "Mutagenesis", Chapter 15 "Expression of Cloned Genes in *Escherichia coli*", Chapter 16 "Introducing Cloned Genes into Cultured Mammalian Cells", Chapter 17 "Analysis of Gene Expression in Cultured Mammalian Cells", Cold Spring Harbor, 3rd Ed., 2001.
Scior et al. (2011) "Directed PCR-free engineering of highly repetitive DNA sequences" BMC Biotechnology, 11:87, 9 pages.
Search Report dated Jul. 23, 2024, Appl. No. GB2407102.9, 3 pp.
Tang et al. (1993) "Self-stabilized antisense oligodeoxynucleotide phosphorothioates: properties and anti-HIV activity" Nucleic Acids Research, 21(11):2729-2735.
Todoroya et al. (2017) "Electroporation as a vaccine delivery system and a natural adjuvant to intradermal administration of plasmid DNA in Macaques" Scientific Reports, 7:4122, 11 pages.
Walters et al. (2014) "Comparative analysis of enzymatically produced novel linear DNA constructs with plasmids for use as DNA vaccines", Gene Therapy, 21(7):645-652.
Werner et al. (2012) "Fast track assembly of multigene constructs using Golden Gate cloning and the MoClo system" Bioengineered, 3(1):38-43.
Yan et al. (2012) "Parallel assembly for multiple site-directed mutagenesis of plasmids" Analytical Biochemistry, 430:65-67.
Combined Search and Examination Report dated Dec. 23, 2025, Appl. No. GB2518093.6, 5 pp.
Search Report dated Dec. 19, 2025, Appl. No. GB2518084.5, 4 pp.
Search Report dated Dec. 24, 2025, Appl. No. GB2518057.1, 4 pp.
Search Report dated Dec. 24, 2025, Appl. No. GB2518059.7, 4 pp.
Search Report dated Jan. 29, 2026, Appl. No. GB2522983.2, 4 pp.
Combined Search and Examination Report dated Aug. 7, 2025, Appl. No. GB2508033.4, 7 pp.
Moreno et al. (2004) "DNA immunisation with minimalistic expression constructs" Vaccine. 22(13-14):1709-1716.
Search Report and Written Opinion (English Translation) dated Jul. 7, 2025, Appl. No. ES 202430713, 6 pp.
Putney et al. (1981) "A DNA fragment with an α-phosphorothioate nucleotide at one end is asymmetrically blocked from digestion by exonuclease III and can be replicated in vivo" Proc. Natl. Acad. Sci. USA, 78(12)7350-7354.
Third-Party Observations dated Feb. 9, 2026, Appln. No. ES 202430713, 7 pages.
Notice of Grounds for Refusal (English Translation) dated Jul. 7, 2026, Appln. No. JP 2024-505284, 4 pages.

* cited by examiner

| DNA construct | Starting amplified DNA | Ligation yield | Linear covalently closed DNA produced |
|---|---|---|---|
| A | 577 µg<br>577 µg | 82%<br>84% | 470 µg<br>484 µg |
| B | 577 µg<br>577 µg | 61%<br>77% | 350 µg<br>445 µg |
| C | 577 µg<br>577 µg | 61%<br>88% | 354 µg<br>507 µg |

Fig. 8 u/t

Construct B

| DNA construct | Starting amplified DNA | Ligation yield | Linear covalently closed DNA produced |
|---|---|---|---|
| Luciferase | 1,73 mg | 67% | 1,10 mg |

| DNA type | Starting amplified DNA | Ligation yield | DNA produced |
|---|---|---|---|
| Partially closed DNA | 2,32 mg | 85% | 1,98 mg |
| Linear DNA comprising protected nucleotides | 2,32 mg | 94% | 2,19 mg |

| DNA type | Starting amplified DNA | Ligation yield | DNA produced |
|---|---|---|---|
| Partially closed DNA | 2,92 mg | 88% | 2,57 mg |
| Linear DNA comprising protected nucleotides | 3,07 mg | 84% | 2,58 mg |

| DNA type | Starting amplified DNA | Ligation yield | DNA produced |
|---|---|---|---|
| Closed linear DNA | 2,32 mg | 62% | 1,44 mg |
| Linear DNA comprising protected nucleotides | 2,21 mg | 71% | 1,57 mg |

LINEAR DNA PRODUCTS

CROSS-REFERENCES TO RELATED APPLICATIONS

This application is a continuation of U.S. patent application Ser. No. 18/261,083 filed on Jul. 11, 2023, which is a national stage filing under 35 U.S.C. § 371 of International Patent Application No. PCT/EP2022/071413, filed on Jul. 29, 2022, which claims the benefit of European Patent Application No. 21382725.6, filed on Jul. 30, 2021, which applications are incorporated herein by reference in their entireties.

TECHNICAL FIELD

The present invention relates to methods for producing a linear deoxyribonucleic acid (DNA) product (e.g. a closed linear DNA product) with enhanced resistance to nuclease digestion. The present invention relates to methods comprising the steps: (a) contacting a double-stranded DNA molecule with an endonuclease, a ligase and first and second adaptor molecules to form a single contiguous aqueous volume; and (b) incubating the single contiguous aqueous volume to generate a linear DNA product (e.g. a closed linear DNA product). The present invention also relates to linear deoxyribonucleic acid (DNA) products (e.g. a closed linear DNA products) with enhanced resistance to nuclease digestion and uses thereof.

INCORPORATION BY REFERENCE OF SEQUENCE LISTING PROVIDED AS A SEQUENCE LISTING XML FILE

A Sequence Listing is provided herewith as a Sequence Listing XML, BOULT_SequenceList_ST26_8-21-25, created on Aug. 21, 2025 and having a size of 32,380 bytes. The contents of the Sequence Listing XML are incorporated herein by reference in their entirety.

BACKGROUND

DNA is susceptible to degradation by nucleases which are naturally occurring enzymes within organisms and which have a vital role in the regulation of many cellular processes, while also protecting against foreign DNA species. Enzymatic DNA degradation can render gene therapies ineffective and is a substantial consideration when developing gene therapies or DNA vaccines.

Considerable efforts have been made to extend the effective molecular lifetime of nucleic acids by increasing resistance of the nucleic acid molecules to both extracellular and intracellular nucleases.

For linear molecules, one of the proposed solutions includes the use of phosphorothioated nucleotides (i.e. 2'-deoxynucleotides-5'-(α-thio)-triphosphate).

Phosphorothioated nucleotides comprise a sulphur atom instead of a non-bridging oxygen atom. These modified nucleotides show comparable physical and chemical characteristics to corresponding unmodified nucleotides, but are resistant to exonuclease digestion. As such, the incorporation of the phosphorothioate functional group can prolong the half-life of the nucleic acid molecule.

Phosphorothioate modifications are used in nucleic acid drug development programmes. In therapeutic nucleic acids, the phosphorothioated nucleotides are incorporated into short, single-stranded polynucleotide chains. For example, an antisense oligonucleotide fomivirsen is a 21-mer phosphorothioate oligodeoxynucleotide used to treat cytomegalovirus retinitis (Stein and Castanotto, "FDA-approved oligonucleotide therapies in 2017." *Molecular Therapy* 25.5 (2017): 1069-1075). Similarly, pegaptanib (brand name Macugen) is a short (27-nucleotides) aptamer with a phosphorothioate 3'-3' deoxythymidine cap used for treating age-related macular degeneration of the retina.

Phosphorothioate modifications have also been used in the context of a linear double-stranded polynucleotide chain (e.g. double-stranded DNA) to cap the ends of the polynucleotide chain to increase resistance to exonuclease digestion (Putney et al. "A DNA fragment with an alpha-phosphorothioate nucleotide at one end is asymmetrically blocked from digestion by exonuclease III and can be replicated in vivo." Proceedings of the National Academy of Sciences 78.12 (1981): 7350-7354). To cap the ends of the polynucleotide chain, the ends are digested with a restriction enzyme and treated with a DNA polymerase and a mixture of deoxyribonucleotide triphosphates (dNTPs), at least one type of which is a phosphorothioated nucleotide complementary to a nucleotide in the overhanging strand. Since DNA polymerases add nucleotides in the 5' to 3' direction, the result of this treatment is a blunt-ended polynucleotide fragment with a phosphorothioated nucleotide located at the 3'-end of each strand (i.e. in "the cap").

Resistance to nuclease digestion can also be accomplished by using closed DNA molecules, such as plasmids or minicircles. However, plasmids and minicircles have limited utility in vivo due to their frequent contamination with toxic agents derived from cell components, fidelity issues that alter the sequence of interest, and presence of different species (supercoiled, linear and open circular).

Alternatively, resistance to nuclease digestion may be accomplished by producing closed linear DNA molecules. For example, WO2010/086626 A1 describes a method for producing a closed linear DNA by utilizing a protelomerase. However, this method is limited in that the action of protelomerase produces the same sequence at both ends of the closed linear DNA molecule.

Thus, a need exists for a more flexible method for producing a linear DNA product with an enhanced resistance to nuclease (e.g. exonuclease) digestion.

DESCRIPTION

The invention provides a method for producing a linear deoxyribonucleic acid (DNA) product (e.g. a closed linear DNA product) with enhanced resistance to nuclease digestion. The invention is based on the addition of adaptor molecules to a double-stranded DNA molecule. The method of the invention relies on the addition of the adaptor molecules, an endonuclease and a ligase to the double-stranded DNA molecule in a single reaction volume (or single contiguous aqueous volume). Thus, the method for producing a linear DNA product comprises the steps: (a) contacting a double-stranded DNA molecule with an endonuclease, a ligase and first and second adaptor molecules to form a single contiguous aqueous volume; and (b) incubating the single contiguous aqueous volume to generate the linear DNA product. Preferably, the linear DNA product has enhanced resistance to exonuclease (e.g. exonuclease I, exonuclease III and/or exonuclease VIII) digestion. The linear DNA product may be a closed linear DNA product. The linear DNA product may comprise nuclease-resistant nucleotides (i.e. protected nucleotides), such as phosphorothioated nucleotides. The linear DNA product may be a partially closed linear DNA product. The partially closed linear DNA product may comprise nuclease-resistant nucleotides (i.e. protected nucleotides), such as phosphorothioated nucleotides. The linear DNA product may comprise a cassette. The cassette may comprise a coding sequence.

The invention provides a method for producing a linear DNA product, wherein the method comprises:

(a) contacting a double-stranded DNA molecule with an endonuclease and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a portion of the double-stranded DNA molecule, and wherein the first adaptor molecule is appended to a first end of the linear double-stranded region and the second adaptor molecule is appended to a second end of the linear double-stranded region.

The first and second adaptor molecules may be identical molecules or they may be different molecules. For example, the first adaptor molecule and/or the second adaptor molecule may comprise a hairpin. The first adaptor molecule and/or the second adaptor molecule may double-stranded linear nucleic acid molecules comprising one or more nuclease-resistant nucleotides. The first adaptor molecule may comprise a hairpin and the second adaptor molecule may be a double-stranded linear nucleic acid molecule comprising one or more nuclease-resistant nucleotides. Thus, the linear DNA product produced by the methods described herein is resistant to nuclease (e.g. exonuclease) digestion.

The step of contacting the double-stranded DNA molecule with the endonuclease and first and second adaptor molecules is preferably performed in the presence of a ligase. Thus, the invention provides a method for producing a linear deoxyribonucleic acid (DNA) product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region.

The appending (or linking or closing) of the first adaptor molecule and/or the second adaptor molecule may be performed by hybridization or ligation of the adaptor molecules to the ends of the linear double-stranded region. Thus, the first adaptor molecule may be hybridized to the first end of the linear double-stranded region. The second adaptor molecule may be hybridized to the second end of the linear double-stranded region. The first adaptor molecule may be ligated to the first end of the linear double-stranded region. The second adaptor molecule may be ligated to the second end of the linear double-stranded region. The appending of the first adaptor molecule and the second adaptor molecule may be performed by both hybridization and ligation of the adaptor molecules to the ends of the linear double-stranded region. Thus, the first adaptor molecule may be hybridized and ligated to the first end of the linear double-stranded region. The second adaptor molecule may be hybridized and ligated to the second end of the linear double-stranded region. The appending may be performed via a linker or spacer molecule which facilitates joining of the adaptor molecule to the first and/or second end of the linear double-stranded region.

The method may further comprise, before step (a) (i.e. the step of contacting the double-stranded DNA molecule with the endonuclease, the ligase and the first and second adaptor molecules), a step of amplification of a DNA template molecule to produce the double-stranded DNA molecule. Thus, the invention provides a method for producing a linear DNA product, the method comprises:

(a) amplification of a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume; and (c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region.

The amplification may be an in vitro or in vivo amplification. Preferably, the amplification is an in vitro amplification. For example, the amplification may be performed by rolling circle amplification (RCA), MALBAC method, traditional polymerase chain reaction (PCR), nucleic acid sequence-based amplification (NASBA), loop-mediated isothermal amplification (LAMP), helicase-dependent amplification (HDA), multiple displacement amplification (MDA) and recombinase polymerase amplification (RPA). Preferably, the amplification is rolling circle amplification. Thus, the invention provides a method for producing a linear deoxyribonucleic acid (DNA) product, the method comprises:

(a) rolling circle amplification of a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume; and (c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region.

The method may further comprise (after the step of amplification and before the step of contacting the double-stranded DNA molecule with an endonuclease, a ligase and first and second adaptor molecules) a step of heat-deactivation. Thus, the invention provides a method for producing a linear DNA product, the method comprises:

(a) amplification of a DNA template molecule comprising at least one cleavable (e.g. endonuclease) target sequence to generate a double-stranded DNA molecule;

(b) heat-deactivation of the reaction of step (a);

(c) contacting the double-stranded DNA molecule with an endonuclease, a ligase and first and second adaptor molecules to form a single contiguous aqueous volume; and (d) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region.

Preferably, amplification is rolling-circle amplification.

The step of heat-deactivation may be performed under conditions sufficient to inactive the reagents used during the amplification reaction. The step of heat-deactivation may be performed at a temperature of at least 50° C., at least 55° C., at least 60° C., at least 65° C., at least 70° C., at least 75° C., at least 80° C., at least 85° C., at least 90° C., at least 95° C., or at least 100° C. The step of heat-deactivation may be performed for at least 1 min, at least 3 mins, at least 5 mins, at least 10 mins, at least 15 mins, or at least 20 mins.

The inventors of the present application have surprisingly discovered that large concatemeric products of the rolling circle amplification reaction can be used to produce the DNA products described herein. This is surprising as the product of the rolling circle amplification has high viscosity and typically has to undergo purification steps before it can be utilized for downstream applications.

In the method described herein, after the step of amplification, the step of contacting the double-stranded DNA molecule with an endonuclease, a ligase and first and second adaptor molecules to form a single contiguous aqueous volume may be performed without purifying the product of the amplification reaction. That is to say that the step of contacting the double-stranded DNA molecule with an endonuclease, a ligase and first and second adaptor molecules may be performed directly after the step of amplification. The step of contacting the double-stranded DNA molecule with an endonuclease, a ligase and first and second adaptor molecules may be performed directly after the step of heat-deactivation.

The inventors of the present application have discovered a method which requires a very few steps to produce the DNA product described herein. The methods described herein are very time efficient. This is, in part, due to the fact that a step of purification is not required after the amplification reaction. Optionally, the product of the amplification reaction may be heat-deactivated. Surprising, the method described herein where the step of contacting the double-stranded DNA molecule with an endonuclease, a ligase and first and second adaptor molecules is performed directly after the step of amplification (i.e. without the step of purification) produces higher yields of the DNA product described herein when compared to a method in which the two steps are separated by purification of the amplification product.

The method may further comprise, after the step of incubating the single contiguous aqueous volume, a step of purification of the linear DNA product.

The method may further comprise, after the step of incubating the single contiguous aqueous volume, a step of nuclease digestion. The nuclease digestion may be exonuclease digestion, such as exonuclease I and/or exonuclease III digestion. The step of nuclease digestion may take place before or after the step of purification. The step of nuclease digestion may allow for removal of any double-stranded DNA molecules and/or adaptor molecules which have not been used to produce linear DNA products. Thus, the method for producing a linear DNA product may comprise the steps:

(a) contacting a double-stranded DNA molecule with an endonuclease, a ligase and first and second adaptor molecules to form a single contiguous aqueous volume;

(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region; and (c) incubating the single contiguous aqueous volume with a nuclease (e.g. an exonuclease).

The method for producing a linear DNA product may comprise the steps:

(a) amplification of a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume;

(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region; and (d) incubating the single contiguous aqueous volume with a nuclease (e.g. an exonuclease).

The method for producing a linear DNA product may comprise the steps:

(a) amplification of a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume;

(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region;

(d) purification of the linear DNA product; and (e) incubating the product of step (d) with a nuclease (e.g. an exonuclease).

The method for producing a linear DNA product may comprise the steps:

(a) amplification of a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume;

(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region;

(d) incubating the single contiguous aqueous volume with a nuclease (e.g. an exonuclease); and (e) purification of the linear DNA product.

The endonuclease may be a restriction enzyme endonuclease. The endonuclease may be a Type IIS restriction enzyme. The endonuclease may be any enzyme that recognizes a DNA sequence and cleaves outside of the recognition sequence. For example, the endonuclease may be a BbsI, BsaI, BsmBI, BspQI, BtgZI, Esp3I, SapI, AarI, Acc36I, AclWI, AcuI, AjuI, AloI, Alw26I, AIwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, BtsI-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction enzyme.

Type IIS restriction endonucleases cleave the double-stranded DNA molecule outside of the recognition sequence (i.e. an endonuclease target sequence), which means that the recognition sequence (i.e. endonuclease target sequence) is not included in the linear DNA product.

The present inventors have surprisingly discovered methods for production of a linear DNA product of enhanced resistance to nuclease digestion. Specifically, the linear DNA product produced by the methods described herein has enhanced resistance to exonuclease digestion (e.g. exonuclease III digestion). The enhanced resistance to exonuclease digestion extends the life of the linear DNA product in a cell (i.e. the linear DNA product has enhanced resistance to intracellular exonucleases) and in a cell-free system (i.e. the linear DNA product has enhanced resistance to extracellular exonucleases). The present inventors have developed a method which relies on the addition of adaptor molecules (i.e. a first adaptor molecule and a second adaptor molecule) to both ends of a double-stranded DNA molecule. The adaptor molecules may comprise a hairpin or a loop to form a closed linear DNA product with enhanced resistance to nuclease (e.g. exonuclease) digestion. In addition, the present inventors have discovered a method for efficient introduction of protected nucleotides in the form of a first adaptor molecule and a second adaptor molecule at both ends of a linear double-stranded region of the linear DNA product. The methods described herein may use a hairpin or a loop adaptor on one end of the DNA product and a linear adaptor comprising protected nucleotides on the other end of the DNA product. That is to say that any type of adaptors described herein may be used as long as the final DNA product is protected from nuclease (e.g. exonuclease) digestion. The methods of the invention provide protection from digestion by exonucleases that cleave the 3'-end nucleotides (e.g. exonuclease III) and exonucleases that cleave the 5'-end nucleotides (e.g. exonuclease VIII). Thus, the linear DNA product produced by the methods of the invention has prolonged in vivo expression when compared to a linear DNA product that does not comprise an adaptor molecule described herein.

As used herein the term "protected nucleotide" or "nuclease-resistant nucleotide" is intended to encompass any type of molecule that provides or enhances resistance to nuclease digestion (especially exonuclease digestion). Although the adaptor molecules are described herein as comprising phosphorothioated nucleotides, the skilled person would appreciate that the adaptor molecules may instead comprise any molecules that provide resistance to nuclease digestion (e.g. exonuclease III digestion). For example, the adaptor molecules may comprise nuclease resistant nucleotides i.e. modified nucleotides that provide or increase resistance to nucleases (e.g. exonucleases). The adaptor molecules may comprise a peptide, polypeptide or protein that provides or increases resistance to nucleases (e.g. exonucleases) digestion. The adaptor molecules may comprise 2'-O-methyl nucleotides or 2'-O-methoxyethyl (MOE) nucleotides.

As used herein, the term "phosphorothioated nucleotide" refers to a nucleotide that has an altered phosphate backbone, wherein, the sugar moieties are linked by a phosphorothioate bond. In the phosphate backbone of an oligonucleotide sequence, the phosphorothioate bond contains a sulphur atom as a substitute for a non-bridging oxygen atom. This modification renders the internucleotide linkage resistant to nuclease degradation.

The linear DNA product (e.g. the closed linear DNA product) produced by the methods of the present invention has additional advantageous properties, such as a substantial lack of a bacterial backbone and/or antibiotic resistant genes. Lack of these features is particularly beneficial in the production of a cell delivery system, such as a viral vector or a nanoparticle, for example, for cell therapy. Lack of these features makes the linear DNA product produced by the methods of the present invention particularly suitable for use in a pharmaceutical composition.

Unexpectedly, the present inventors have discovered a method for production of a linear DNA product of enhanced resistance to nuclease digestion which allows for efficient production of large quantities of the linear DNA product with enhanced resistance to exonuclease digestion. The large-scale manufacture of the product may be in a cell-free system, which results in the production of a pure sample comprising the linear DNA product substantively free of bacterial contaminants (e.g. remaining after cell lysis).

1. Methods for Producing Closed Linear DNA Product

The methods described herein may be used to produce a closed linear DNA product e.g. a covalently closed linear DNA product.

The invention provides a method for producing a closed linear DNA product, the method comprises:

(a) contacting a double-stranded DNA molecule with an endonuclease and first and second adaptor molecules to form a single contiguous aqueous volume; and (b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

The step of contacting the double-stranded DNA molecule with the endonuclease and first and second adaptor molecules is preferably performed in the presence of a ligase. Thus, the invention provides a method for producing a closed linear DNA product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

The linear double-stranded region may be the linear portion of the double-stranded DNA molecule.

The invention provides a method for producing a closed linear DNA product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the closed linear DNA product, wherein the closed linear DNA product comprises a linear portion of the double-stranded DNA molecule, and wherein the linear portion of the double-stranded DNA molecule is closed at a first end by the first adaptor molecule and closed at a second end by the second adaptor molecule.

A closed linear DNA product has particular utility as a therapeutic agent (i.e. DNA therapeutic) which can be used to express a gene product in vivo. This is because its closed structure (e.g. covalently closed structure) prevents attack by enzymes such as exonucleases, leading to enhanced stability and longevity of gene expression as compared to "open" DNA molecules with exposed DNA ends.

Linear double-stranded open-ended cassettes have been demonstrated to be inefficient with respect to gene expression when introduced into host tissue. This has been attributed to cassette instability due to the action of exonucleases in the extracellular space.

Sequestering DNA ends inside closed structures also has other advantages. The DNA ends are prevented from integrating with genomic DNA and so closed linear DNA products offer improved safety. In addition, the closed linear structure reduces concatamerisation of DNA products inside host cells and thus expression levels of the gene product can be regulated in a more sensitive manner.

The method of the invention may be used for production of DNA for in vitro expression in a host cell, for example, in DNA vaccines. DNA vaccines typically encode a modified form of an infectious organism's DNA. DNA vaccines are administered to a subject where they then express the selected protein of the infectious organism, initiating an immune response against that protein which is typically protective. DNA vaccines may also encode a tumour antigen in a cancer immunotherapy approach. The method may produce other types of therapeutic DNA molecules e.g. those used in gene therapy. For example, such DNA molecules can be used to express a functional gene where a subject has a genetic disorder caused by a dysfunctional version of that gene. Examples of such diseases include sickle cell anaemia, cystic fibrosis, Huntington disease, Duchenne's Muscular Dystrophy, Haemophilia A, α1-antitrypsin deficiency, primary ciliary dyskinesia, or respiratory distress syndrome of prematurity. Other diseases where gene therapy may be useful include metabolic diseases, respiratory diseases, inflammatory diseases, autoimmune, chronic and infectious diseases, including such disorders as AIDS, cancer, neurological diseases, cardiovascular disease, hypercholesterolemia, various blood disorders including various anaemias, thalassemia and haemophilia, and emphysema. For the treatment of solid tumours, genes encoding toxic peptides (i.e., chemotherapeutic agents such as ricin, diptheria toxin and cobra venom factor), tumour suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, may be expressed.

The closing of the linear double-stranded region by the first adaptor molecule and/or the second adaptor molecule may be performed by hybridization or ligation of the adaptor molecules to the ends of the linear double-stranded region. Thus, the first adaptor molecule may be hybridized to the first end of the linear double-stranded region. The second adaptor molecule may be hybridized to the second end of the linear double-stranded region. The first adaptor molecule may be ligated to the first end of the linear double-stranded region. The second adaptor molecule may be ligated to the second end of the linear double-stranded region. The closing of the linear double-stranded region by the first adaptor molecule and the second adaptor molecule may be performed by both hybridization and ligation of the adaptor molecules to the ends of the linear double-stranded region. Thus, the first adaptor molecule may be hybridized and ligated to the first end of the linear double-stranded region. The second adaptor molecule may be hybridized and ligated to the second end of the linear double-stranded region.

The step of incubating the single contiguous aqueous volume to generate the closed linear DNA product may comprise generating the linear portion of the double-stranded DNA molecule by digesting the double-stranded DNA molecule with the endonuclease.

The step of incubating the single contiguous aqueous volume may be performed under conditions that promote appending (or linking) of the first and second adaptor molecules to the linear double-stranded region to produce the closed linear DNA product. The appending may be performed by creating a covalent link between the first and/or second adaptor molecule and the first and/or second end of the linear double-stranded region.

The step of incubating the single contiguous aqueous volume may be performed under conditions that promote digestion of the double-stranded DNA molecule to produce the linear portion of the double-stranded DNA molecule. The digestion of the double-stranded DNA molecule to produce the linear portion of the double-stranded DNA molecule may be performed at a first temperature of 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or at about 37° C. The digestion may be endonuclease digestion, preferably Type IS endonuclease digestion.

The step of incubating the single contiguous aqueous volume may be performed under conditions that promote ligation of the linear double-stranded region to the first and second adaptor molecules. The ligation may be at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% efficient. For example, at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% of the linear double-stranded regions (or the portions of the double-stranded DNA molecules) may be incorporated into closed linear DNA products. Preferably, the ligation is at least 15% efficient.

Ligation efficiency may be established based on DNA quantification values before and after the digestion/ligation reaction. Thus, ligation efficiency may be established based on the equation: (starting amplified DNA amount)/(final linear DNA amount)×100%.

Ligation efficiency may also be established based on DNA quantification values before and after the digestion/ligation reaction and the subsequent exonuclease treatment to remove remaining open DNA constructs and adaptor molecules excess.

For example, the double-stranded DNA molecule generated by the rolling circle amplification is first quantified so that the amount of the double-stranded DNA molecule used as the starting material during the digestion/ligation reaction is known. After all the enzymatic reactions, the linear DNA product is quantified to calculate the ligation efficiency as per the equation above.

DNA quantification methods are known to a person skilled in the art. For example, DNA quantifications may be carried out using the Qubit dsDNA BR assay from ThermoFisher (world-wide-website:thermofisher.com/order/catalog/product/Q32850 #/Q32850).

The step of ligation of the linear double-stranded region to the first and second adaptor molecules may be performed at a second temperature of 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C.

The step of incubating the single contiguous aqueous volume may comprise incubating at a first temperature and then incubating at a second temperature. The first temperature may be 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or about 37° C. The second temperature may be 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C. Preferably, the first temperature is 35° C.-39° C. and the second temperature is 14° C.-18° C. Using these conditions the endonuclease may be a Type IIS restriction endonuclease (e.g. BsaI) and the ligase may be T4 DNA ligase, T7 DNA ligase, mammalian DNA ligase I, III and IV; Taq DNA ligase, Tth DNA ligase, or *E. coli* DNA ligase.

The step of incubating the single contiguous aqueous volume may be performed isothermally. The step of incubating the single contiguous aqueous volume may comprise incubating at a constant temperature. The constant temperature promotes simultaneous digestion of the double-stranded DNA molecule to produce the linear portion of the double-stranded DNA molecule and ligation of the linear double-stranded region to the first and second adaptor molecules. For example, the constant temperature may be 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. Preferably, the constant temperature is 30° C. The constant temperature is intended to mean that the temperature does not significantly change during the reaction. The constant temperature is intended to mean that the temperature variation during the step of incubating the single contiguous aqueous volume is less than 10° C., less than 9° C., less than 8° C., less than 7° C., less than 6° C., less than 5° C., less than 4° C., less than 3° C., less than 2° C., or less than 1° C. In a preferred embodiment the temperature during the step of incubating the single contiguous aqueous does not deviate by more than 5° C., preferably by not more than 3° C., even more preferably not more than 1° C. Thus, the constant temperature may be a temperature in a range of 20° C.-30° C., 22° C.-32° C., 24° C.-34° C., 26° C.-36° C., 28° C.-38° C., 30° C.-40° C., 22° C.-28° C., 32° C.-38° C., 25° C.-35° C., 26° C.-34° C., 27° C.-33° C., 27.5° C.-32.5° C., 28° C.-32° C., 28.5° C.-31.5° C., 29° C.-31° C., or 29.5° C.-30.5° C. Preferably, the constant temperature is a temperature in a range of 27.5° C.-32.5° C. Alternatively, the constant temperature may be a temperature in a range of 32° C.-42° C., 33° C.-41° C., 34° C.-40° C., 35° C.-39° C., 36° C.-38° C. Preferably, the constant temperature is a temperature in a range of 34.5° C.-39.5° C.

The step of incubating the single contiguous aqueous volume may comprise cycling between the first temperature and the second temperature. The step of incubating the single contiguous aqueous volume may comprise cycling between the first temperature and the second temperature at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 80, at least 90, or at least 100 times, preferably at least 20 times. The step of incubating the single contiguous aqueous volume may comprise cycling between the first temperature and the second temperature less than 40, less than 35, less than 30 times, less than 29, less than 25 times. The step of incubating the single contiguous aqueous volume may comprise cycling between the first temperature and the second temperature 2-100, 5-80, 10-70, 20-60, or 30-60 times. The step of incubating the single contiguous aqueous volume may comprise cycling between the first temperature and the second temperature 2-20, 5-29, 61-100, or 65-80 times.

The method may further comprise, before step (a) (i.e. the step of contacting the double-stranded DNA molecule with the endonuclease, the ligase and the first and second adaptor molecules), a step of amplifying a DNA template molecule to produce the double-stranded DNA molecule. Thus, the invention provides a method for producing a closed linear DNA product, the method comprises:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume; and
(c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

The step of amplifying may be performed by in vitro or in vivo amplification. Preferably, the step of amplifying is performed by in vitro amplification. For example, the step of amplifying may be performed by rolling circle amplification (RCA), MALBAC method, traditional polymerase chain reaction (PCR), nucleic acid sequence-based amplification (NASBA), loop-mediated isothermal amplification (LAMP), helicase-dependent amplification (HDA), multiple displacement amplification (MDA) and recombinase polymerase amplification (RPA). Preferably, the step of amplifying is performed by rolling circle amplification. Thus, the invention provides a method for producing a closed linear DNA product, the method comprises:

(a) amplifying a DNA template molecule comprising at least one cleavable (e.g. endonuclease) target sequence to generate a double-stranded DNA molecule, wherein the DNA template molecule is amplified by rolling circle amplification;

(b) contacting the double-stranded DNA molecule with an endonuclease, a ligase and first and second adaptor molecules to form a single contiguous aqueous volume; and (c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

Rolling circle amplification may be performed without any primers, or in the presence of a primer or multiple primers. For example, the primer may be a synthetic primer. The primers may be random primers. Rolling circle amplification may be performed in the presence of a primase. The primase may be TthPrimPol. Preferably, if the rolling circle amplification is performed without any primers, it is performed in the presence of a primase, such as TthPrimPol. Similarly, if a primer is used during amplification reaction, a primase is not used. The double-stranded DNA product may be generated by the rolling circle amplification in vitro under isothermal conditions using a suitable nucleic acid polymerase, such as Phi29 DNA polymerase.

In the methods described herein, the DNA template molecule may comprise at least one cleavable target sequence. The cleavable target sequence may be an endonuclease target sequence. Thus, the DNA template molecule may comprise at least one endonuclease target sequence. Preferably, the DNA template molecule comprises at least two endonuclease target sequences. The endonuclease target sequences may be the same or different. Preferably, the at least one endonuclease target sequence is a restriction endonuclease target sequence. Different restriction endonuclease target sequences would be known to the skilled person. The cleavable target sequence may be a Type IIS restriction endonuclease target sequence. For example, the restriction endonuclease target sequence may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequence. The at least one cleavable sequence (e.g. endonuclease target sequence) may be a native cleavable sequence (i.e. a cleavable sequence present in the template molecule). Alternatively, the at least one cleavable sequence (e.g. endonuclease target sequence) may be introduced to the DNA template molecule prior to the production of the closed linear DNA product.

The endonuclease may be a restriction enzyme endonuclease. The endonuclease may be a Type IIS restriction enzyme. The endonuclease may be any enzyme that recognizes a DNA sequence and cleaves outside of the recognition sequence. For example, the endonuclease may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction enzyme.

The ligase may be a DNA ligase, such as a T4 DNA ligase, T7 DNA ligase, mammalian DNA ligase I, III and IV; Taq DNA ligase, Tth DNA ligase, or *E. coli* DNA ligase.

The DNA template molecule used in the methods described herein may be single-stranded or double-stranded. Preferably, the DNA template molecule is double-stranded. The DNA template molecule may be a natural circular DNA molecule. For example, the DNA template molecule may be (i) a plasmid, (ii) a minicircle, (iii) a cosmid, (iv) a bacterial artificial chromosome (BAC), or (v) a molecular inversion probe (MIP). The DNA template molecule may be an enzymatically produced circular DNA molecule. For example, the DNA template molecule may be (i) a circular DNA molecule obtained from recombinase reaction, preferably Cre recombinase reaction, or (ii) a circular DNA molecule obtained from ligase reaction, preferably using the golden gate assembly. The DNA template molecule may be an enzymatically produced covalently-closed linear DNA molecule. For example, the DNA template molecule may be (i) a DNA molecule processed with TelN protelomerase; or (ii) a DNA molecule generated by ligation of the DNA ends with an adaptor. The DNA template molecule may comprise an element that is double-stranded and an element that is single-stranded. For example, the template DNA molecule may comprise a double-stranded DNA and a single-stranded hairpin loop.

The DNA template molecule may be linear. If the DNA template molecule is linear, prior to amplification (e.g. rolling circle amplification), a DNA template molecule may be circularized to produce a DNA template molecule suitable for use in the methods described herein.

The template DNA molecule may comprise a cassette. The cassette may be a mammalian expression cassette. The cassette may further comprise a promoter. The promoter may be a CMV promoter. The cassette may further comprise an enhancer. The cassette may further comprise a reporter gene, such as an eGFP reporter gene or a luciferase reporter gene. The cassette may further comprise a homopolymeric sequence. The cassette may further comprise a LoxP sequence, preferably two LoxP sequences. If the two LoxP sequences are oriented in the same direction, the DNA sequence between the two LoxP sequences is excised as a circular loop of DNA. If the two LoxP sequences are oriented in the opposite direction, the DNA sequence between the two LoxP sequences is inverted. Thus, preferably, the two LoxP sequences are in the same orientation (i.e. the same direction) in the template DNA molecule.

The DNA template molecule may comprise a homopolymeric sequence at a 5'-end or a 3'-end or both a 5'-end and a 3'-end. The homopolymeric sequence may be added to the DNA template molecule before circularization. The homopolymeric sequence may be a polyA, a polyC, a polyG, or a polyT sequence. The homopolymeric sequence may be between 3-200 nucleotides in length. The homopolymeric sequence may be used to facilitate purification of the linear DNA product, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The method may further comprise (after the step of amplification and before the step of contacting the double-stranded DNA molecule with an endonuclease, a ligase and first and second adaptor molecules) a step of heat-deactivation. Thus, the invention provides a method for producing a closed linear DNA product, the method comprises:

(a) amplification of a DNA template molecule comprising at least one cleavable (e.g. endonuclease) target sequence to generate a double-stranded DNA molecule;
(b) heat-deactivation of the reaction of step (a);
(c) contacting the double-stranded DNA molecule with an endonuclease, a ligase and first and second adaptor molecules to form a single contiguous aqueous volume; and
(d) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

Preferably, amplification is rolling-circle amplification.

The step of heat-deactivation may be performed under conditions sufficient to inactive the reagents used during the amplification reaction. The step of heat-deactivation may be performed at a temperature of at least 50° C., at least 55° C., at least 60° C., at least 65° C., at least 70° C., at least 75° C., at least 80° C., at least 85° C., at least 90° C., at least 95° C., or at least 100° C. The step of heat-deactivation may be performed for at least 1 min, at least 3 mins, at least 5 mins, at least 10 mins, at least 15 mins, or at least 20 mins.

In the method described herein, after the step of amplification, the step of contacting the double-stranded DNA molecule with an endonuclease, a ligase and first and second adaptor molecules to form a single contiguous aqueous volume may be performed without purifying the product of the amplification reaction. That is to say that the step of contacting the double-stranded DNA molecule with an endonuclease, a ligase and first and second adaptor molecules may be performed directly after the step of amplification. The step of contacting the double-stranded DNA molecule with an endonuclease, a ligase and first and second adaptor molecules may be performed directly after the step of heat-deactivation.

The method may further comprise, after the step of incubating the single contiguous aqueous volume, a step of purification of the closed linear DNA product.

The method may further comprise, after the step of incubating the single contiguous aqueous volume, a step of nuclease digestion. The nuclease digestion may be exonuclease digestion, such as exonuclease I and/or exonuclease III digestion. The step of nuclease digestion may take place before or after the step of purification. This step allows for removal of any double-stranded DNA molecules and/or adaptor molecules which have not been used in the course of performing the method. Thus, the method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule; and
(d) incubating the single contiguous aqueous volume with a nuclease (e.g. exonuclease).

In the method described herein, after the step of amplification, the step of contacting the double-stranded DNA molecule with an endonuclease, a ligase and first and second adaptor molecules to form a single contiguous aqueous volume may be performed without purifying the product of the amplification reaction. That is to say that the step of contacting the double-stranded DNA molecule with an endonuclease, a ligase and first and second adaptor molecules may be performed directly after the step of amplification. The step of contacting the double-stranded DNA molecule with an endonuclease, a ligase and first and second adaptor molecules may be performed directly after the step of heat-deactivation.

The method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(d) purifying the closed linear DNA product; and (e) incubating the purified product of step (d) with a nuclease (e.g. exonuclease).

The method may comprise the steps:

(a) amplifying a DNA template molecule comprising at least one cleavable (e.g. endonuclease) target sequence to generate a double-stranded DNA molecule;

(b) heat-deactivation of the reaction of step (a);

(c) contacting the double-stranded DNA molecule with an endonuclease, a ligase and first and second adaptor molecules to form a single contiguous aqueous volume;

(d) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(e) purifying the closed linear DNA product; and (f) incubating the purified product of step (d) with a nuclease (e.g. exonuclease).

The method may comprise the steps:

(a) amplifying a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume;

(c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(d) incubating the single contiguous aqueous volume with a nuclease (e.g. exonuclease); and (e) purifying the closed linear DNA product.

The method may comprise the steps:

(a) amplifying a DNA template molecule comprising at least one cleavable (e.g. endonuclease) target sequence to generate a double-stranded DNA molecule;

(b) heat-deactivation of the reaction of step (a);

(c) contacting the double-stranded DNA molecule with an endonuclease, a ligase and first and second adaptor molecules to form a single contiguous aqueous volume;

(d) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(e) incubating the single contiguous aqueous volume with a nuclease (e.g. exonuclease); and (f) purifying the closed linear DNA product.

The step of incubating the single contiguous aqueous volume (or the purified product of step (d)) with a nuclease may be performed at a temperature of 5-90° C., 10-80° C., 15-70° C., 20-60° C., 25-50° C., 30-45° C. or 35-40° C. The step of incubating the single contiguous aqueous volume (or the purified product of step (d)) with a nuclease may be performed for at least 10, at least 20, at least 30, at least 40, at least 50, or at least 60 min. The step of incubating the single contiguous aqueous volume (or the purified product of step (d)) may be performed at two different temperatures. For example, the step of incubating the single contiguous aqueous volume (or the purified product of step (d)) may be performed at 15-40° C. for 10-60 minutes followed by a temperature of 60-90° C. for 10-30 min. The higher temperature typically inactivates the nuclease (e.g. exonuclease). Thus, the method further provides a step of inactivating the nuclease (e.g. exonuclease). The step of incubating the single contiguous aqueous volume (or the purified product of step (d)) may be performed at 37° C. for 30 min and 80° C. for 20 min. Preferably, the step of inactivating the nuclease (e.g. exonuclease) is performed at a temperature of 70-80° C. The step of inactivating the nuclease (e.g. exonuclease) may be performed for at least 1, at least 5, at least 10, at least 20 or at least 30 minutes. Preferably, the step of inactivating the nuclease (e.g. exonuclease) is performed for at least 5 minutes.

The method may be a cell-free method.

The closed linear DNA product may be partially double-stranded and/or partially single-stranded. The closed linear DNA product may comprise a portion that is double-stranded and a portion that is single-stranded.

The closed linear DNA product may comprise a cassette. The cassette may comprise a coding sequence. The coding sequence may encode a gene of interest, for example a gene encoding a protein.

The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. For example, the homopolymeric sequence may comprise a polyA sequence of at least 120 nucleotides.

The closed linear DNA product may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long.

The closed linear DNA product may comprise an inverted terminal repeat sequence.

The closed linear DNA product may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the closed linear DNA product is at least 50 base pairs long.

The double-stranded DNA molecule may be circular, or branched.

The double-stranded DNA molecule may not comprise an adaptor. The double-stranded DNA molecule may not comprise a hairpin, a loop or a stem-loop structure.

The double-stranded DNA molecule may comprise a cassette. The cassette may comprise a coding sequence. The coding sequence may encode a gene of interest, for example a gene encoding a protein. The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The double-stranded DNA molecule may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long. The spacer may improve an amplification yield of the double-stranded DNA molecule.

The double-stranded DNA molecule may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The double-stranded DNA molecule may comprise one or more cleavable (e.g. endonuclease) target sequences. The double-stranded DNA molecule may comprise two cleavable (e.g. endonuclease) target sequences. The one or more cleavable (e.g. endonuclease) target sequences may be Type IIS endonuclease target sequences. The one or more cleavable (e.g. endonuclease) target sequences may be BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstFSI, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequences.

The double-stranded DNA molecule may be a product of amplification. Preferably, the amplification is rolling circle amplification.

The linear double-stranded region (e.g. the linear portion of the double-stranded molecule) may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The linear double-stranded region (e.g. the linear portion of the double-stranded molecule) may comprise a sequence that is at least 40%, 45%, 50%, 55%, 60%, 65%, 70%, 75%, 80%, 85%, 90%, 95%, or 100% identical to the sequence of the double-stranded DNA molecule.

The first end and the second end of the linear double-stranded region (e.g. the linear portion of the double-stranded molecule) may be resistant to nuclease digestion. Preferably, the first end and the second end of the linear double-stranded region are resistant to the exonuclease digestion, such as exonuclease III digestion and/or exonuclease I digestion.

The linear double-stranded region may comprise a 3'-OH group at first and/or second ends. The 3'-OH group may facilitate ligation to the first and/or second adaptor molecule (s) (which may comprise a 5' phosphate). The linear double-stranded region may comprise a 5' phosphate at first and/or second ends. The 5' phosphate may facilitate ligation to the first and/or second adaptor molecule(s) (which may comprise a 3'-OH group).

The linear double-stranded region (e.g. the linear portion of the double-stranded molecule) may comprise an overhang. For example, the linear double-stranded region may comprise a 5' overhang or a 3' overhang. The linear double-stranded region may comprise a blunt end or blunt ends. The linear double-stranded region may comprise: a 5' overhang and a blunt end, two 5' overhangs, a 3' overhang and a blunt end, two 3' overhangs, or a 5' overhang and a 3' overhang. The overhang may have at least 3 nucleotides (preferably from 4 to 8 nucleotides). The overhang may be in the sense strand or the antisense strand of the linear double-stranded region.

The linear portion of the double-stranded DNA molecule (e.g. the linear portion of the double-stranded molecule) may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, double-stranded DNA molecule is at least 50 base pairs long.

The first adaptor molecule and/or the second adaptor molecule may be a synthetic adaptor molecule.

The first adaptor molecule may be a nucleic acid adaptor molecule. The second adaptor molecule may be a nucleic acid adaptor molecule. The first adaptor molecule and/or the second adaptor molecule may comprise a self-complementary element which creates a loop, such as a hairpin loop or a stem loop. Thus, the first adaptor molecule may comprise a hairpin or a stem-loop. The second adaptor molecule may comprise a hairpin or a stem-loop. Both the first and second adaptor molecules may comprise a hairpin or a stem-loop. The adaptor molecules may each comprise a double-stranded portion comprising a sense strand and an antisense strand, wherein the sense strand and the antisense strand are linked together in a hairpin such that the sense strand is hybridized to the antisense strand. The double-stranded portion of an adaptor may comprise a 3' overhang or a 5' overhang of at least 1, at least 2, at least 3, at least 4, or at least 5 nucleotides. Preferably the 3' overhang or the 5' overhang is 4-8 nucleotides. Each end of the linear double-stranded region (or linear portion of the double-stranded DNA molecule) may comprise a 3' or a 5' overhang. A portion of the first adaptor molecule (e.g. the overhang) may be complementary to the first end of the linear double-stranded region. A portion of the second adaptor molecule may be complementary to the second end of the linear double-stranded region.

The closed linear DNA product may be a covalently closed linear DNA product. Thus, in embodiments where the adaptor molecules comprise a loop (e.g. a hairpin), the adaptor molecules close the ends of the linear double-stranded region forming a covalently closed linear DNA product.

The invention provides a method for producing a covalently closed linear DNA product, wherein the method comprises:

(a) contacting a double-stranded DNA molecule with an endonuclease, a ligase and first and second adaptor molecules to form a single contiguous aqueous volume, wherein the first and second adaptor molecules are nucleic acid adaptor molecules that each comprise a hairpin; and (b) incubating the single contiguous aqueous volume to generate the covalently closed linear DNA product, wherein the covalently closed linear DNA product comprises a linear double-stranded region, wherein the linear double-stranded region comprises a linear portion of the double-stranded DNA molecule, wherein the linear double-stranded region is closed at a first end by the first adaptor molecule and closed at a second end by the second adaptor molecule, wherein (i) the first adaptor molecule comprises an overhang that is complementary to and anneals to an overhang at the first end of the linear double-stranded region thereby closing the first end of the linear double-stranded region and (ii) the second adaptor molecule comprises an overhang that is complementary to and anneals to an overhang at the second end of the linear double-stranded region thereby closing the second end of the linear double-stranded region.

The invention provides a method for producing a covalently closed linear DNA product, wherein the method comprises:

(a) contacting a double-stranded DNA molecule with an endonuclease, a ligase and first and second adaptor molecules to form a single contiguous aqueous volume, wherein the first and second adaptor molecules are nucleic acid adaptor molecules that each comprise a hairpin; and (b) incubating the single contiguous aqueous volume to generate the covalently closed linear DNA product, wherein the covalently closed linear DNA product comprises a linear double-stranded region, wherein the linear double-stranded region comprises a linear portion of the double-stranded DNA molecule, wherein the linear double-stranded region is closed at a first end by the first adaptor molecule and closed at a second end by the second adaptor molecule, wherein (i) the first adaptor molecule comprises an overhang that is complementary to and anneals to an overhang at the first end of the linear double-stranded region thereby closing the first end of the linear double-stranded region and (ii) the second adaptor molecule comprises an overhang that is complementary to and anneals to an overhang at the second end of the linear double-stranded region thereby closing the second end of the linear double-stranded region, and wherein the first adaptor molecule is ligated to the first end of the linear double-stranded region and the second adaptor molecule is ligated to the second end of the linear double-stranded region.

The invention provides a method for producing a covalently closed linear DNA product, wherein the method comprises:

(a) contacting a double-stranded DNA molecule with an endonuclease, a ligase and first and second adaptor molecules to form a single contiguous aqueous volume, wherein the first and second adaptor molecules are nucleic acid adaptor molecules that each comprise a hairpin; and (b) incubating the single contiguous aqueous volume to generate the covalently closed linear DNA product, wherein the covalently closed linear DNA product comprises a linear portion of the double-stranded DNA molecule, wherein the linear portion of the double-stranded DNA molecule is closed at a first end by the first adaptor molecule and closed at a second end by the second adaptor molecule, wherein (i) the first adaptor molecule comprises an overhang that is complementary to and anneals to an overhang at the first end of the linear portion of the double-stranded DNA molecule thereby closing the first end of the linear portion of the double-stranded DNA molecule and (ii) the second adaptor molecule comprises an overhang that is complementary to and anneals to an overhang at the second end of the linear portion of the double-stranded DNA molecule thereby closing the second end of the linear portion of the double-stranded DNA molecule, and wherein the first adaptor molecule is ligated to the first end of the linear portion of the double-stranded DNA molecule and the second adaptor molecule is ligated to the second end of the linear portion of the double-stranded DNA molecule.

The first adaptor molecule and/or the second adaptor molecule may not be a plasmid or a vector DNA.

The first adaptor molecule and/or the second adaptor molecule may comprise a single-stranded portion. The single-stranded portion may form a hairpin or a stem-loop. Thus, the first adaptor molecule and/or the second adaptor molecule may comprise a loop portion. The single-stranded portion may comprise less than 10, 9, 8, 7, 6, 5, 4, 3, 2 nucleotides. Preferably, the single-stranded portion comprises 5 nucleotides.

The first adaptor molecule and/or the second adaptor molecule may comprise a double-stranded portion. The double-stranded portion may comprise less than 50, less than 45, less than 40, less than 35, less than 30, less than 25, less than 20, less than 15, or less than 10 base pairs. The double-stranded portion may comprise at least 5, at least 6, at least 7, at least 8, at least 9, at least 10, at least 11, at least 12, at least 13, at least 14, or at least 15 base pairs.

The first adaptor molecule and/or the second adaptor molecule may comprise a 5' phosphate. The 5' phosphate may facilitate ligation to the linear double-stranded region (which may comprise a 3'-OH group at first and/or second ends). The first adaptor molecule and/or the second adaptor molecule may comprise a 3'-OH. The 3'-OH may facilitate ligation to the linear double-stranded region (which may comprise a 5' phosphate at first and/or second ends).

The first adaptor molecule and/or the second adaptor molecule may comprise the sequence of SEQ ID NO: 1 or a portion thereof. The first adaptor molecule and/or the second adaptor molecule may comprise at least 13, at least 14, at least 15, at least 16, at least 17, at least 18, or at least 19 contiguous nucleotides of SEQ ID NO: 1. The double-stranded portion of the first adaptor molecule and/or the second adaptor molecule may comprise the sequence of SEQ ID NO: 2 or a portion thereof. The double-stranded portion of the first adaptor molecule and/or the second adaptor molecule may comprise at least 8, at least 9, at least 10, at least 11, at least 12, at least 13, at least 14 or at least 15 contiguous nucleotides of SEQ ID NO: 2. The single-stranded portion of the first adaptor molecule and/or the second adaptor molecule may comprise a sequence of ACTCA. The single-stranded portion of the first adaptor molecule and/or the second adaptor molecule may comprise at least 1, at least 2, at least 3, at least 4 or at least 5 contiguous nucleotides of the sequence ACTCA. The first and second adapter molecules may comprise an identical nucleic acid sequence. The first and second adapter molecules may comprise a different nucleic acid sequence.

The first adaptor molecule may comprise a portion that is complementary to the first end of the linear double-stranded region (or the linear portion of the double-stranded DNA molecule). The second adaptor molecule may comprise a portion that is complementary to the second end of the linear double-stranded region (or the linear portion of the double-stranded DNA molecule). The first adaptor molecule may comprise a portion that anneals to the first end of the linear double-stranded region (or the linear portion of the double-stranded DNA molecule). The second adaptor molecule may comprise a portion that anneals to the second end of the linear double-stranded region (or the linear portion of the double-stranded DNA molecule). The first adaptor molecule may comprise a portion that is complementary and anneals to the first end of the linear double-stranded region (or the linear portion of the double-stranded DNA molecule). The second adaptor molecule may comprise a portion that is complementary and anneals to the second end of the linear double-stranded region (or the linear portion of the double-stranded DNA molecule).

The portion that is complementary or anneals to the first or second end of the linear double-stranded region (or the linear portion of the double-stranded DNA molecule) may be a 5' overhang or a 3' overhang of the first and/or second adaptor molecule. The overhang of the first adaptor molecule may be complementary to the first end of the linear double-stranded region and/or the overhang of the second adaptor molecule may be complementary to the second end of the double-stranded region.

The overhang of the first adaptor molecule may anneal to the first end of the linear double-stranded region and/or the overhang of the second adaptor molecule may anneal to the second end of the linear double-stranded region. The overhang of the first adaptor molecule may be complementary to and anneal to the first end of the linear double-stranded region and/or the overhang of the second adaptor molecule may be complementary to and anneal to the second end of the linear double-stranded region.

The first adaptor molecule and/or the second adaptor molecule may not comprise a Type IIS endonuclease target sequence. The first adaptor molecule and/or the second adaptor molecule may not comprise BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequences.

The first adaptor molecule and/or the second adaptor molecule may comprise one or more locked nucleic acids (LNAs).

The first adaptor molecule and/or the second adaptor molecule may comprise one or more protected nucleotides (i.e. nuclease-resistant nucleotides), such as phosphorothioated nucleotides. The protected nucleotides may be located in the single-stranded portion (e.g. hairpin portion) or the double-stranded portion. The protected nucleotides may be located in the overhang portion of the adaptor molecules.

The closed linear DNA product may comprise a plurality of phosphorothioated nucleotides at internal positions in each strand. For example, the closed linear DNA product may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, or at least 500 protected nucleotides (e.g. phosphorothioated nucleotides) at internal positions in each strand. Preferably, the closed linear DNA product comprises at least 2 protected nucleotides (e.g. phosphorothioated nucleotides) at internal positions in each strand.

The internal positions may not be located between the second and penultimate nucleotide of the closed linear DNA product.

The linear double-stranded region (or linear portion of the double-stranded molecule) may comprise a plurality of phosphorothioated nucleotides at internal positions in each strand. For example, the linear double-stranded region (or linear portion of the double-stranded molecule) may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, at least or 500 protected nucleotides (e.g. phosphorothioated nucleotides) at internal positions in each strand. Preferably, the linear double-stranded region (or linear portion of the double-stranded molecule) comprises at least 2 protected nucleotides (e.g. phosphorothioated nucleotides) at internal positions in each strand. The internal positions may not be located between the second and penultimate nucleotide of the linear double-stranded region (or linear portion of the double-stranded molecule).

The nucleotides resistant to exonuclease digestion (i.e. protected nucleotides) suitable for use in the methods described herein may be phosphorothioated nucleotides. For example, phosphorothioated nucleotides may be α-S-dATP (i.e. 2'-deoxyadenosine-5'-(α-thio)-triphosphate), α-S-dCTP (i.e. 2'-deoxycytidine-5'-(α-thio)-triphosphate), α-S-dGTP (i.e. 2'-deoxyguanosine-5'-(α-thio)-triphosphate), α-S-dTTP (i.e. 2'-deoxythymidine-5'-(α-thio)-triphosphate), α-S-dUTP (i.e. 2'-deoxyuridine-5'-(α-thio)-triphosphate), and/or uridine 2', 3'-cyclophosphorothioate.

The phosphorothioated nucleotides may be Sp-isomers, Rp-isomers or a mixture of both Sp- and Rp-isomers.

The nucleotides resistant to exonuclease digestion (i.e. protected nucleotides) may be 2'-O-methyl nucleotides or 2'-O-methoxyethyl (MOE) nucleotides. For example, the MOE nucleotides may be 2'-O-methoxy-ethyl guanosine, 2'-O-methoxy-ethyl cytidine, 2'-O-methoxy-ethyl adenosine, and/or 2'-O-methoxy-ethyl thymidine.

The first end of the linear double-stranded region may be complementary to a portion of the first adaptor molecule. The second end of the linear double-stranded region may be complementary to a portion of the second adaptor molecule. The first end and/or the second end of the linear double-stranded region may be generated by endonuclease digestion.

The first adaptor molecule and/or the second adaptor molecule may comprise a functional portion. The functional portion may be a binding molecule, a targeting sequence, or a probe.

The functional portion may be a probe. As used herein, the term "probe" refers to a fragment of DNA, RNA or DNA/RNA chimera of variable length (e.g. 3-1000 bases long), which is used to detect the presence of target nucleotide sequences that are complementary to the sequence in the probe. Typically, the probe hybridizes to single-stranded nucleic acid whose base sequence allows probe-target base pairing due to complementarity between the probe and target. Thus, the functional portion may be a DNA sequence, a RNA sequence or a DNA/RNA chimera sequence. As used herein, the term "complementary" refers to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence.

The functional portion may be a binding molecule. The term "binding molecule" refers to any molecule capable of binding to the linear DNA product described herein and/or that is capable of binding to a further molecule or target. The binding molecule may be a protein, a polypeptide, or a peptide. The binding molecule may be an antibody, such as a monoclonal antibody or a polyclonal antibody. The binding molecule may be an antibody fragment.

The functional portion may facilitate detection of the DNA product by binding to capture molecules (e.g. capture antibodies bound by protein-protein interactions). The functional portion may bind to a cell target, for example, a cell receptor.

The functional portion may be a label. The 'label' can be any chemical entity which enable the detection of the double-stranded nucleic acid molecule via, physical, chemical and/or biological means. The label may be a chromophore, a fluorophore and/or a radioactive molecule.

The functional portion may be a targeting sequence. The targeting sequence may be a fragment of DNA or RNA of variable length, which is used to target the DNA product to a specific location in a cell. The targeting sequence may be used to increased transfection efficiency of non-viral gene delivery by virtue of enhanced nuclear import of the closed linear DNA product. For example, the targeting sequence may be a DNA nuclear targeting sequences (i.e. a recognition sequence for endogenous DNA-binding proteins), such as SV40 enhancer sequence (preferably downstream from the cassette).

To facilitate detection and/or quantification of the DNA product, the functional portion may comprise a fluorophore, a radioactive compound or a barcode.

A signal corresponding to the presence, absence and/or level of the closed linear DNA product may be measured using a barcode. The barcode may comprise at least one binding moiety linked to a barcoded portion, wherein the barcoded portion comprises at least one nucleotide (i.e. wherein the barcoded portion comprises a nucleotide sequence at least one nucleotide in length), and wherein the binding moiety is capable of binding to the 3' overhang, the 5' overhang or the blunt end of the closed linear DNA product. The binding moiety is capable of binding to 3' and/or 5' end of the closed linear DNA product. The signal may be measured by determining the presence, absence and/or level of the barcoded portion of the barcode (e.g. by sequencing or PCR). The barcoded portion may comprise at least 2, at least 3, at least 4, at least 5, at least 6, at least 7, at least 8, at least 9, or at least 10 nucleotides. The barcode may comprise at least 2 binding moieties (e.g. a first binding moiety and a second binding moiety). For example, the first binding moiety linked to the first barcoded portion may bind to the 3' end of the closed linear DNA product and the second binding moiety linked to the second barcoded portion may bind to the 5' end of the closed linear DNA product. The 3' and 5' ends may comprise a 3' overhang, a 5' overhang or a blunt end.

A signal corresponding to the presence, absence and/or level of the closed linear DNA product may be measured using a fluorophore (i.e. a fluorescently-labelled molecule), which is attached or bound to the 3' overhang, the 5' overhang or the blunt end of the closed linear DNA product. The signal may be measured by flow cytometry and/or fluorescence-activated cell sorting.

The functional portion may also facilitate DNA sequencing. For example, the functional portion may be a sequencing adapter. The term "sequencing adapter" is intended to encompass one or more nucleic acid domains that include at least a portion of a nucleic acid sequence (or complement thereof) utilized by a sequencing platform of interest, such as a sequencing platform provided by Illumina® (e.g. the HiSeq™, MiSeq™ and/or Genome Analyzer™ sequencing systems), Oxford Nanopore™ Technologies (e.g. the MinION sequencing system), Ion Torrent™ (e.g. the Ion PGM™ and/or Ion Proton™ sequencing systems), Pacific Biosciences (e.g. the PACBIO RS II sequencing system); Life Technologies™ (e.g. a SOLiD sequencing system), Roche (e.g. the 454 GS FLX+ and/or GS Junior sequencing systems), or any other sequencing platform of interest.

The first adaptor molecule and/or the second adaptor molecule may comprise an inverted terminal repeat sequence. The inverted terminal repeat sequences of the first adaptor molecule and the second adaptor molecule may be symmetrical (i.e. have the same symmetrical three-dimensional organization with respect to each other) or asymmetrical (i.e. have different three-dimensional organization with respect to each other). The inverted terminal repeat sequences of the first adaptor molecule and the second adaptor molecule may be from the same or different serotypes. An inverted terminal repeat sequence may comprise a terminal resolution site and a Rep binding site.

The first adaptor molecule and/or the second adaptor molecule may comprise an aptamer.

The first adaptor molecule and/or the second adaptor molecule may confer resistance to the nuclease digestion, such as exonuclease digestion (e.g. exonuclease I and/or exonuclease III digestion).

The closing of the linear double-stranded region (or the linear portion of the double-stranded DNA molecule) at the first end may generate a first closed end of the closed linear DNA product. The closing of the linear double-stranded region (or the linear portion of the double-stranded DNA molecule) at the second end may generate a second closed end of the closed linear DNA product.

The first closed end and the second closed end of the closed linear DNA product may be resistant to nuclease digestion. The nuclease digestion may be exonuclease digestion. Preferably, the nuclease digestion is exonuclease III digestion and/or exonuclease I digestion.

2. Methods for Producing a Linear DNA Product Comprising Nuclease-Resistant Nucleotides The methods described herein may be used to produce a linear DNA product comprising nuclease-resistant (i.e. protected nucleotides).

The invention provides a method for producing a linear deoxyribonucleic acid (DNA) product, wherein the method comprises:

(a) contacting a double-stranded DNA molecule with an endonuclease and first and second adaptor molecules to form a single contiguous aqueous volume; and
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides).

The step of contacting the double-stranded DNA molecule with the endonuclease and first and second adaptor molecules is preferably performed in the presence of a ligase. Thus, the method for producing a linear DNA product may comprise the steps:

(a) contacting a double-stranded DNA molecule with an endonuclease, a ligase and first and second adaptor molecules to form a single contiguous aqueous volume; and
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides).

The linear DNA product produced by the methods described herein has enhanced resistance to nuclease (e.g. exonuclease) digestion. For example, the linear DNA product has prolonged in vivo expression when compared to a linear DNA product that does not contain protected nucleotides.

The appending of the first adaptor molecule and/or the second adaptor molecule may be performed by hybridization or ligation of the adaptor molecules to the ends of the linear double-stranded region. Thus, the first adaptor molecule may be hybridized to the first end of the linear double-stranded region. The second adaptor molecule may be hybridized to the second end of the linear double-stranded region. The first adaptor molecule may be ligated to the first end of the linear double-stranded region. The second adaptor molecule may be ligated to the second end of the linear double-stranded region. The appending of the first adaptor molecule and the second adaptor molecule may be performed by both hybridization and ligation of the adaptor molecules to the ends of the linear double-stranded region. Thus, the first adaptor molecule may be hybridized and ligated to the first end of the linear double-stranded region. The second adaptor molecule may be hybridized and ligated to the second end of the linear double-stranded region. The hybridization is based on complementarity of a portion of the first and/or second adaptor molecules to the first and/or second end of the linear double-stranded region.

The method for producing a linear DNA product may comprise the steps:

(a) contacting a double-stranded DNA molecule with an endonuclease, a ligase and first and second adaptor molecules to form a single contiguous aqueous volume; and
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides (i.e. protected nucleotides).

The method for producing a linear DNA product may comprise the steps:

(a) contacting a double-stranded DNA molecule with an endonuclease, a ligase and first and second adaptor molecules to form a single contiguous aqueous volume; and (b) incubating the single contiguous aqueous volume to generate the linear DNA product, wherein the linear DNA product comprises a linear portion of the double-stranded DNA molecule, and wherein the first adaptor molecule is ligated to a first end of the linear portion of the double-stranded DNA molecule and the second adaptor molecule is ligated to a second end of the linear portion of the double-stranded DNA molecule, and wherein the first and second adaptor molecules are nucleic acid molecules that comprise one or more nuclease-resistant nucleotides (i.e. protected nucleotides).

As used herein, the term “complementary” refers to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence.

Preferably, the step of contacting the double-stranded DNA molecule with the endonuclease, the ligase and first and second adaptor molecules is performed in a single reaction (i.e. a single step).

The step of incubating the single contiguous aqueous volume to generate the linear DNA product may comprise generating the linear portion of the double-stranded DNA molecule by digesting the double-stranded DNA molecule with the endonuclease.

The step of incubating the single contiguous aqueous volume may be performed under conditions that promote appending (or linking) of the first and second adaptor molecules to the linear double-stranded region to produce the linear DNA product. The appending may be performed by creating a covalent link between the first and/or second adaptor molecule and the end(s) of the linear double-stranded region (or linear portion of the double-stranded DNA molecule).

The step of incubating the single contiguous aqueous volume may be performed under conditions that promote digestion of the double-stranded DNA molecule to produce the linear portion of the double-stranded DNA molecule. The digestion of the double-stranded DNA molecule to produce the linear portion of the double-stranded DNA molecule may be performed at a first temperature of 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or at about 37° C. The digestion may be endonuclease digestion, preferably Type IS endonuclease digestion.

The step of incubating the single contiguous aqueous volume may be performed under conditions that promote ligation of the linear double-stranded region to the first and second adaptor molecules. The ligation may be at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% efficient. For example, at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% of the linear double-stranded regions (or the portions of the double-stranded DNA molecules) may be incorporated into closed linear DNA products. Preferably, the ligation is at least 15% efficient.

The step of ligation of the linear double-stranded region to the first and second adaptor molecules may be performed at a second temperature of 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C.

The step of incubating the single contiguous aqueous volume may comprise incubating at a first temperature and then incubating at a second temperature. The first temperature may be 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or about 37° C. The second temperature may be 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C. Preferably, the first temperature is 35° C.-39° C. Preferably, the second temperature is 14° C.-18° C.

The step of incubating the single contiguous aqueous volume may comprise cycling between the first temperature and the second temperature. The step of incubating the single contiguous aqueous volume may comprise cycling between the first temperature and the second temperature at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 80, at least 90, or at least 100 times, preferably at least 20 times. The step of incubating the single contiguous aqueous volume may comprise cycling between the first temperature and the second temperature less than 40, less than 35, less than 30 times, less than 29, less than 25 times. The step of incubating the single contiguous aqueous volume may comprise cycling between the first temperature and the second temperature 2-100, 5-80, 10-70, 20-60, or 30-60 times. The step of incubating the single contiguous aqueous volume may comprise cycling between the first temperature and the second temperature 2-20, 5-29, 61-100, or 65-80 times.

The step of incubating the single contiguous aqueous volume may be performed isothermally. The step of incubating the single contiguous aqueous volume may comprise incubating at a constant temperature. The constant temperature promotes simultaneous digestion of the double-stranded DNA molecule to produce the linear portion of the double-stranded DNA molecule and ligation of the linear double-stranded region to the first and second adaptor molecules. For example, the constant temperature may be 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. Preferably, the constant temperature is 30° C. The constant temperature is intended to mean that the temperature does not significantly change during the reaction. The constant temperature is intended to mean that the temperature variation during the step of incubating the single contiguous aqueous volume is less than 10° C., less than 9° C., less than 8° C., less than 7° C., less than 6° C., less than 5° C., less than 4° C., less than 3° C., less than 2° C., or less than 1° C. In a preferred embodiment the temperature during the step of incubating the single contiguous aqueous does not deviate by more than 5° C., preferably by not more than 3° C., even more preferably not more than 1° C. Thus, the constant temperature may be a temperature in a range of 20° C.-30° C., 22° C.-32° C., 24° C.-34° C., 26° C.-36° C., 28° C.-38° C., 30° C.-40° C., 22°

C.-28° C., 32° C.-38° C., 25° C.-35° C., 26° C.-34° C., 27° C.-33° C., 27.5° C.-32.5° C., 28° C.-32° C., 28.5° C.-31.5° C., 29° C.-31° C., or 29.5° C.-30.5° C. Preferably, the constant temperature is a temperature in a range of 27.5° C.-32.5° C. Alternatively, the constant temperature may be a temperature in a range of 32° C.-42° C., 33° C.-41° C., 34° C.-40° C., 35° C.-39° C., 36° C.-38° C. Preferably, the constant temperature is a temperature in a range of 34.5° C.-39.5° C.

The first and second adaptor molecules may comprise one or more phosphorothioated nucleotides, such that, once the adaptor molecules are appended (e.g. ligated) to the linear double-stranded region, the linear DNA product is resistant to nuclease digestion or has improved or enhanced resistance to nuclease digestion. The linear DNA product may be resistant to 3'-end exonuclease digestion (e.g. by exonuclease III) and/or 5'-end exonuclease digestion (e.g. by exonuclease VIII).

The adaptor molecule may comprise a plurality of phosphorothioated nucleotides. For example, the adaptor molecules may comprise at least 2, at least 3, at least 4, at least 5, at least 6, at least 7, at least 8, at least 9, at least 10, at least 11, at least 12, at least 13, at least 14, at least 15 or at least 16 phosphorothioated nucleotides in each strand.

The adaptor molecule may be a nucleic acid adaptor molecule. The adaptor molecule may be double-stranded. The adaptor molecule may comprise a portion that is double-stranded.

The first and/or second adaptor molecules may comprise at least 3, at least 4, at least 5, at least 6, at least 7, at least 8, at least 9, at least 10, at least 11, at least 12, at least 13, at least 14, at least 15, or at least 16 base pairs.

The adaptor molecule may comprise a plurality of phosphorothioated nucleotides in each strand. For example, the adaptor molecules may comprise at least 2, at least 3, at least 4, at least 5, at least 6, at least 7, at least 8, at least 9, at least 10, at least 11, at least 12, at least 13, at least 14, at least 15 or at least 16 phosphorothioated nucleotides in each strand.

The adaptor molecule may comprise a plurality of phosphorothioated nucleotides at internal positions in each strand. For example, the adaptor molecules may comprise at least 1, at least 2, at least 3, at least 4, at least 5, at least 6, at least 7, at least 8, at least 9, at least 10, at least 11, at least 12, at least 13, at least 14, at least 15 or at least 16 phosphorothioated nucleotides at internal positions in each strand. Preferably, the adaptor molecule comprises at least 2 phosphorothioated nucleotides at internal positions in each strand.

The internal positions may not be located between the second and penultimate nucleotide of the adaptor molecule. The internal positions may be any position in the adaptor molecules other than the last nucleotide at the end of each strand.

The adaptor molecule may comprise at least 5%, at least 10%, at least 20%, at least 30%, at least 40%, at least 50%, at least 60%, at least 70%, at least 80%, at least 90%, at least 95%, or at least 100% of protected nucleotides.

Once the adaptor molecules are appended to the linear double-stranded region, the linear DNA product may comprise a protected nucleotide (e.g. phosphorothioated nucleotide) at the 5'-end (or at the 5'-end region) of one or both strands. Preferably, the linear DNA product comprises a phosphorothioated nucleotide at the 5'-end (or at the 5'-end region) of one or both strands. The linear DNA product may comprise a phosphorothioated nucleotide at the 5'-end (or at the 5'-end region) of one or both strands. As most exonucleases, for example exonuclease III, remove nucleotides from the 3'-end of the polynucleotide chain, the linear DNA product may comprise a protected nucleotide at the 3'-end (or at the 3'-end region) of one or both strands. Preferably, the linear DNA product comprises a phosphorothioated nucleotide at the 3'-end (or the 3'-end region) of one or both strands. The linear DNA product may comprise at least one phosphorothioated nucleotide at the 3'-end (or the 3'-end region) and at least one phosphorothioated nucleotide at the 5'-end (or the 5'-end region) of one or both strands. The linear DNA product may comprise a phosphorothioated nucleotide at the 3'-end (or the 3'-end region) and the 5'-end (or the 5'-end region) of one or both strands.

The linear DNA product may additionally comprise a plurality of protected nucleotides (e.g. phosphorothioated nucleotides) at internal positions in each strand. For example, the linear DNA product may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, or at least 500 protected nucleotides (e.g. phosphorothioated nucleotides) at internal positions in each strand. Preferably, the linear DNA product comprises at least 2 protected nucleotides (e.g. phosphorothioated nucleotides) at internal positions in each strand.

The internal positions may not be located between the second and penultimate nucleotide of the linear DNA product. The internal positions may be any position in the adaptor molecules other than the last nucleotide at the end of each strand.

The linear double-stranded region (or linear portion of the double-stranded molecule) may comprise a plurality of phosphorothioated nucleotides at internal positions in each strand. For example, the linear double-stranded region (or linear portion of the double-stranded molecule) may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, or at least 500 protected nucleotides (e.g. phosphorothioated nucleotides) at internal positions in each strand. Preferably, the linear double-stranded region (or linear portion of the double-stranded molecule) comprises at least 2 protected nucleotides (e.g. phosphorothioated nucleotides) at internal positions in each strand. The internal positions may not be located between the second and penultimate nucleotide of the linear double-stranded region (or linear portion of the double-stranded molecule).

The nucleotides resistant to exonuclease digestion (i.e. protected nucleotides) may be phosphorothioated nucleotides of at least one type. For example, the at least one type of phosphorothioated nucleotides is α-S-dATP (i.e. 2'-deoxyadenosine-5'-(α-thio)-triphosphate), α-S-dCTP (i.e. 2'-deoxycytidine-5'-(α-thio)-triphosphate), α-S-dGTP (i.e. 2'-deoxyguanosine-5'-(α-thio)-triphosphate), α-S-dTTP (i.e. 2'-deoxythymidine-5'-(α-thio)-triphosphate), α-S-dUTP (i.e. 2'-deoxyuridine-5'-(α-thio)-triphosphate), and/or uridine 2', 3'-cyclophosphorothioate.

The adaptor molecules may comprise at least two types of phosphorothioated nucleotides. For example, the at least two types of phosphorothioated nucleotides are: α-S-dATP and α-S-dCTP, α-S-dATP and α-S-dGTP, α-S-dATP and α-S-dTTP, α-S-dCTP and α-S-dGTP, α-S-dCTP and α-S-dTTP, or α-S-dGTP and α-S-dTTP.

The adaptor molecules may comprise at least three types of phosphorothioated nucleotides. For example, the at least three types of phosphorothioated nucleotides are:

(a) α-S-dATP, α-S-dCTP and α-S-dGTP;
(b) α-S-dATP, α-S-dCTP and α-S-dTTP;
(c) α-S-dATP, α-S-dGTP and α-S-dTTP; or
(d) α-S-dCTP, α-S-dGTP and α-S-dTTP.

The adaptor molecules may comprise at least four types of phosphorothioated nucleotides. For example, the at least four types of protected nucleotides are α-S-dATP, α-S-dCTP, α-S-dGTP and α-S-dTTP.

The phosphorothioated nucleotides may be Sp-isomers, Rp-isomers or a mixture of both Sp- and Rp-isomers.

The nucleotides resistant to exonuclease digestion (i.e. protected nucleotides) may be MOE nucleotides of at least one type, or at least two, three or four types. For example, the MOE nucleotides may be 2'-O-methoxy-ethyl guanosine, 2'-O-methoxy-ethyl cytidine, 2'-O-methoxy-ethyl adenosine, and/or 2'-O-methoxy-ethyl thymidine.

The method may further comprise, before step (a) (i.e. the step of contacting the double-stranded DNA molecule with the endonuclease, the ligase and the first and second adaptor molecules), a step of amplifying a DNA template molecule to produce the double-stranded DNA molecule. Thus, the invention provides a method for producing a linear DNA product, the method comprises:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume; and
(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides).

The step of amplifying may be performed by in vitro or in vivo amplification. Preferably, the step of amplifying is performed by in vitro amplification. For example, the step of amplifying may be performed by rolling circle amplification (RCA), MALBAC method, traditional polymerase chain reaction (PCR), nucleic acid sequence-based amplification (NASBA), loop-mediated isothermal amplification (LAMP), helicase-dependent amplification (HDA), multiple displacement amplification (MDA) and recombinase polymerase amplification (RPA). Preferably, the step of amplifying is performed by rolling circle amplification. Thus, the invention provides a method for producing a linear DNA product, the method comprises:

(a) amplifying a DNA template molecule comprising at least one cleavable (e.g. endonuclease) target sequence to generate a double-stranded DNA molecule, wherein the DNA template molecule is amplified by rolling circle amplification;
(b) contacting the double-stranded DNA molecule with an endonuclease, a ligase and first and second adaptor molecules to form a single contiguous aqueous volume; and
(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides).

Rolling circle amplification may be performed without any primers, or in the presence of a primer or multiple primers. For example, the primer may be a synthetic primer. The primers may be random primers. Rolling circle amplification may be performed in the presence of a primase. The primase may be TthPrimPol. Preferably, if the rolling circle amplification is performed without any primers, it is performed in the presence of a primase, such as TthPrimPol. Similarly, if a primer is used during amplification reaction, a primase is not used. The double-stranded DNA product may be generated by the rolling circle amplification in vitro under isothermal conditions using a suitable nucleic acid polymerase, such as Phi29 DNA polymerase.

In the methods described herein, the DNA template molecule may comprise at least one cleavable target sequence. The cleavable target sequence may be an endonuclease target sequence. Thus, the DNA template molecule may comprise at least one endonuclease target sequence. Preferably, the DNA template molecule comprises at least two endonuclease target sequences. The endonuclease target sequences may be the same or different. Preferably, the at least one endonuclease target sequence is a restriction endonuclease target sequence. Different restriction endonuclease target sequences would be known to the skilled person. The cleavable target sequence may be a Type IIS restriction endonuclease target sequence. For example, the restriction endonuclease target sequence may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, BtsI-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequence. The at least one cleavable sequence (e.g. endonuclease target sequence) may be a native cleavable sequence (i.e. a cleavable sequence present in the template molecule). Alternatively, the at least one cleavable sequence (e.g. endonuclease target sequence) may be introduced to the DNA template molecule prior to the production of the linear DNA product.

The endonuclease may be a restriction enzyme endonuclease. The endonuclease may be a Type IIS restriction enzyme. The endonuclease may be any enzyme that recognizes a DNA sequence and cleaves outside of the recognition sequence. For example, the endonuclease may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, Bts-MutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction enzyme.

The ligase may be a DNA ligase, such as a T4 DNA ligase, T7 DNA ligase, mammalian DNA ligase I, III and IV; Taq DNA ligase, Tth DNA ligase, or *E. coli* DNA ligase.

The DNA template molecule used in the methods described herein may be single-stranded or double-stranded. Preferably, the DNA template molecule is double-stranded. The DNA template molecule may be a natural circular DNA molecule. For example, the DNA template molecule may be (i) a plasmid, (ii) a minicircle, (iii) a cosmid, (iv) a bacterial artificial chromosome (BAC), or (v) a molecular inversion probe (MIP). The DNA template molecule may be an enzymatically produced circular DNA molecule. For example, the DNA template molecule may be (i) a circular DNA molecule obtained from recombinase reaction, preferably Cre recombinase reaction, or (ii) a circular DNA molecule obtained from ligase reaction, preferably using the golden gate assembly. The DNA template molecule may be an enzymatically produced covalently-closed linear DNA molecule. For example, the DNA template molecule may be (i) a DNA molecule processed with TelN protelomerase; or (ii) a DNA molecule generated by ligation of the DNA ends with an adaptor. The DNA template molecule may comprise an element that is double-stranded and an element that is single-stranded. For example, the template DNA molecule may comprise a double-stranded DNA and a single-stranded hairpin loop.

The DNA template molecule may be linear. If the DNA template molecule is linear, prior to amplification (e.g. rolling circle amplification), a DNA template molecule may be circularized to produce a DNA template molecule suitable for use in the methods described herein.

The template DNA molecule may comprise a cassette. The cassette may be a mammalian expression cassette. The cassette may further comprise a promoter. The promoter may be a CMV promoter. The cassette may further comprise an enhancer. The cassette may further comprise a reporter gene, such as an eGFP reporter gene or a luciferase reporter gene. The cassette may further comprise a homopolymeric sequence. The cassette may further comprise a LoxP sequence, preferably two LoxP sequences. If the two LoxP sequences are oriented in the same direction, the DNA sequence between the two LoxP sequences is excised as a circular loop of DNA. If the two LoxP sequences are oriented in the opposite direction, the DNA sequence between the two LoxP sequences is inverted. Thus, preferably, the two LoxP sequences are in the same orientation in the template DNA molecule.

The DNA template molecule may comprise a homopolymeric sequence at a 5'-end or a 3'-end or both a 5'-end and a 3'-end. The homopolymeric sequence may be added to the DNA template molecule before circularization. The homopolymeric sequence may be a polyA, a polyC, a polyG, or a polyT sequence. The homopolymeric sequence may be between 3-200 nucleotides in length. The homopolymeric sequence may be used to facilitate purification of the linear DNA product, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The method may further comprise, after the step of incubating the single contiguous aqueous volume, a step of purification of the linear DNA product.

The method may further comprise, after the step of incubating the single contiguous aqueous volume, a step of nuclease digestion. The nuclease digestion may be exonuclease digestion, such as exonuclease I and/or exonuclease III digestion. The step of nuclease digestion may take place before or after the step of purification. This step allows for removal of any double-stranded DNA molecules and/or adaptor molecules which have not been used in the course of performing the method. Thus, the method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides); and
(d) incubating the single contiguous aqueous volume with a nuclease (e.g. exonuclease).

The method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides);

(d) purifying the closed linear DNA product; and (e) incubating the purified product of step (d) with a nuclease (e.g. exonuclease).

The method may comprise the steps:

(a) amplifying a DNA template molecule comprising at least one cleavable (e.g. endonuclease) target sequence to generate a double-stranded DNA molecule;

(b) contacting the double-stranded DNA molecule with an endonuclease, a ligase and first and second adaptor molecules to form a single contiguous aqueous volume;

(c) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides (i.e. protected nucleotides);

(d) incubating the single contiguous aqueous volume with a nuclease (e.g. exonuclease); and (e) purifying the closed linear DNA product.

The step of incubating the single contiguous aqueous volume (or the purified product of step (d)) with a nuclease may be performed at a temperature of 5-90° C., 10-80° C., 15-70° C., 20-60° C., 25-50° C., 30-45° C. or 35-40° C. The step of incubating the single contiguous aqueous volume (or the purified product of step (d)) with a nuclease may be performed for at least 10, at least 20, at least 30, at least 40, at least 50, or at least 60 min. The step of incubating the single contiguous aqueous volume (or the purified product of step (d)) may be performed at two different temperatures. For example, the step of incubating the single contiguous aqueous volume (or the purified product of step (d)) may be performed at 15-40° C. for 10-60 minutes followed by a temperature of 60-90° C. for 10-30 min. The higher temperature typically inactivates the nuclease (e.g. exonuclease). Thus, the method further provides a step of inactivating the nuclease (e.g. exonuclease). The step of incubating the single contiguous aqueous volume (or the purified product of step (d)) may be performed at 37° C. for 30 min and 80° C. for 20 min. Preferably, the step of inactivating the nuclease (e.g. exonuclease) is performed at a temperature of 70-80° C. The step of inactivating the nuclease (e.g. exonuclease) may be performed for at least 1, at least 5, at least 10, at least 20 or at least 30 minutes. Preferably, the step of inactivating the nuclease (e.g. exonuclease) is performed for at least 5 minutes.

The first adaptor molecule and/or the second adaptor molecule may comprise an overhang. The end of the linear double-stranded region may comprise a 3' or a 5' overhang. A portion of the first adaptor molecule (e.g. the overhang) may be complementary to the first end of the linear double-stranded region. A portion of the second adaptor molecule may be complementary to the second end of the linear double-stranded region.

The first end and the second end of the linear double-stranded region may be resistant to nuclease digestion. Preferably, the first end and the second end of the linear double-stranded region are resistant to the exonuclease digestion, such as exonuclease III digestion and/or exonuclease I digestion.

The linear DNA product may be partially double-stranded and/or partially single-stranded. The linear DNA product may comprise a portion that is double-stranded and a portion that is single-stranded.

The linear DNA product may comprise a cassette. The cassette may comprise a coding sequence. The coding sequence may encode a gene of interest, for example a gene encoding a protein. The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The linear DNA product may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long. The spacer may improve ligation efficiency of the first and second adaptor molecules to the linear double-stranded region. The spacer may improve a cell transfection yields.

The linear DNA product may comprise an inverted terminal repeat sequence.

The linear DNA product may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the linear DNA product is at least 50 base pairs long.

The double-stranded DNA molecule may be circular, or branched.

The double-stranded DNA molecule may not comprise an adaptor molecule. The double-stranded DNA molecule may not comprise a hairpin, a loop or a stem-loop structure.

The double-stranded DNA molecule may comprise a cassette. The cassette may comprise a coding sequence. The coding sequence may encode a gene of interest, for example a gene encoding a protein. The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length.

More preferably still, the homopolymeric sequence is at least 120 nucleotides in length. For example, the homopolymeric sequence may comprise a polyA sequence of at least 120 nucleotides.

The double-stranded DNA molecule may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long. The spacer may improve an amplification yield of the double-stranded DNA molecule. The spacer may improve ligation efficiency of the first and second adaptor molecules to the linear double-stranded region. The spacer may improve a cell transfection yields.

The double-stranded DNA molecule may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The double-stranded DNA molecule may comprise one or more cleavable (e.g. endonuclease) target sequences. The double-stranded DNA molecule may comprise two cleavable (e.g. endonuclease) target sequences. The one or more endonuclease target sequences may be Type IIS endonuclease target sequences. The one or more endonuclease target sequences may be BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnII, Mva1269I, NmeAIII, PaqCI, PciSI, PctI, PleI, PpsI, PsrI, SchI, SfaNI, TaqII, TspDTI and/or TspGWI target sequences.

The double-stranded DNA molecule may be a product of amplification. Preferably, the amplification is rolling circle amplification.

The linear double-stranded region may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The linear double-stranded region may comprise a 3'-OH group at first and/or second ends. The 3'-OH group may facilitate ligation to the first and/or second adaptor molecule (s) (which may comprise a 5' phosphate). The linear double-stranded region may comprise a 5' phosphate at first and/or second ends. The 5' phosphate may facilitate ligation to the first and/or second adaptor molecule(s) (which may comprise a 3'-OH group).

The linear double-stranded region (e.g. the linear portion of the double-stranded molecule) may comprise an overhang. For example, the linear double-stranded region may comprise a 5' overhang or a 3' overhang. The linear double-stranded region may comprise a blunt end or blunt ends. The linear double-stranded region may comprise: a 5' overhang and a blunt end, two 5' overhangs, a 3' overhang and a blunt end, two 3' overhangs, or a 5' overhang and a 3' overhang. The overhang may have at least 3 nucleotides (preferably from 4 to 8 nucleotides). The overhang may be in the sense strand or the antisense strand of the linear double-stranded region.

The linear portion of the double-stranded DNA molecule (e.g. the linear portion of the double-stranded molecule) may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, double-stranded DNA molecule is at least 50 base pairs long.

The first adaptor molecule and/or the second adaptor molecule may be a synthetic adaptor molecule.

The first adaptor molecule and/or the second adaptor molecule may not be a plasmid or a vector DNA.

The first adaptor molecule and/or the second adaptor molecule may comprise a single-stranded portion. The single-stranded portion may comprise less than 10, 9, 8, 7, 6, 5, 4, 3, 2 nucleotides. Preferably, the single-stranded portion comprises 5 nucleotides.

The first adaptor molecule and/or the second adaptor molecule may comprise a double-stranded portion. The double-stranded portion may comprise less than 50, less than 45, less than 40, less than 35, less than 30, less than 25, less than 20, less than 15, or less than 10 base pairs. The double-stranded portion may comprise at least 5, at least 6, at least 7, at least 8, at least 9, at least 10, at least 11, at least 12, at least 13, at least 14, or at least 15 base pairs.

The first adaptor molecule and/or the second adaptor molecule may comprise a 5' phosphate. The 5' phosphate may facilitate ligation to the linear double-stranded region.

The first adaptor molecule may comprise a portion that is complementary to the first end of the linear double-stranded region. The second adaptor molecule may comprise a portion that is complementary to the second end of the linear double-stranded region. The first adaptor molecule may comprise a portion that anneals to the first end of the linear double-stranded region. The second adaptor molecule may comprise a portion that anneals to the second end of the linear double-stranded region.

The first adaptor molecule and/or the second adaptor molecule may comprise an overhang. For example, the first adaptor molecule and/or the second adaptor molecule may comprise a 5' overhang or a 3' overhang. The first adaptor molecule and/or the second adaptor molecule may comprise a blunt end. The overhang may have at least 3 nucleotides (preferably from 4 to 6 nucleotides). The overhang of the first adaptor molecule and/or the second adaptor molecule may be complementary to the first and/or second end of the linear double-stranded region. The overhang of the first adaptor molecule and/or the second adaptor molecule may anneal to the first and/or second end of the linear double-stranded region.

The first adaptor molecule and/or the second adaptor molecule may not comprise a Type IIS endonuclease target sequence. The first adaptor molecule and/or the second adaptor molecule may not comprise BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI SapI target sequences.

The first adaptor molecule and/or the second adaptor molecule may comprise a functional portion. The functional portion may be a binding molecule, a targeting sequence, or a probe.

The functional portion may be a probe. As used herein, the term "probe" refers to a fragment of DNA, RNA or DNA/RNA chimera of variable length (e.g. 3-1000 bases long), which is used to detect the presence of target nucleotide sequences that are complementary to the sequence in the probe. Typically, the probe hybridizes to single-stranded nucleic acid whose base sequence allows probe-target base pairing due to complementarity between the probe and target. Thus, the functional portion may be a DNA sequence, a RNA sequence or a DNA/RNA chimera sequence. As used herein, the term "complementary" refers to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence.

The functional portion may be a binding molecule. The term "binding molecule" refers to any molecule capable of binding to the linear DNA product described herein and/or that is capable of binding to a further molecule or target. The binding molecule may be a protein, a polypeptide, or a peptide. The binding molecule may be an antibody, such as a monoclonal antibody or a polyclonal antibody. The binding molecule may be an antibody fragment.

The functional portion may facilitate detection of the DNA product by binding to capture molecules (e.g. capture antibodies bound by protein-protein interactions). The functional portion may bind to a cell target, for example, a cell receptor.

The functional portion may be a label. The 'label' can be any chemical entity which enable the detection of the double-stranded nucleic acid molecule via, physical, chemical and/or biological means. The label may be a chromophore, a fluorophore and/or a radioactive molecule.

The functional portion may be a targeting sequence. The targeting sequence may be a fragment of DNA or RNA of variable length, which is used to target the DNA product to a specific location in a cell. The targeting sequence may be used to increased transfection efficiency of non-viral gene delivery by virtue of enhanced nuclear import of the linear DNA product. For example, the targeting sequence may be a DNA nuclear targeting sequences (i.e. a recognition sequence for endogenous DNA-binding proteins), such as SV40 enhancer sequence (preferably downstream from the cassette).

To facilitate detection and/or quantification of the DNA product, the functional portion may comprise a fluorophore, a radioactive compound or a barcode.

A signal corresponding to the presence, absence and/or level of the linear DNA product may be measured using a barcode. The barcode may comprise at least one binding moiety linked to a barcoded portion, wherein the barcoded portion comprises at least one nucleotide (i.e. wherein the barcoded portion comprises a nucleotide sequence at least one nucleotide in length), and wherein the binding moiety is capable of binding to the 3' overhang, the 5' overhang or the blunt end of the linear DNA product. The binding moiety is capable of binding to 3' and/or 5' end of the linear DNA product. The signal may be measured by determining the presence, absence and/or level of the barcoded portion of the barcode (e.g. by sequencing or PCR). The barcoded portion may comprise at least 2, at least 3, at least 4, at least 5, at least 6, at least 7, at least 8, at least 9, or at least 10 nucleotides. The barcode may comprise at least 2 binding moieties (e.g. a first binding moiety and a second binding moiety). For example, the first binding moiety linked to the first barcoded portion may bind to the 3' end of the linear DNA product and the second binding moiety linked to the second barcoded portion may bind to the 5' end of the linear DNA product. The 3' and 5' ends may comprise a 3' overhang, a 5' overhang or a blunt end.

A signal corresponding to the presence, absence and/or level of the linear DNA product may be measured using a fluorophore (i.e. a fluorescently-labelled molecule), which is attached or bound to the 3' overhang, the 5' overhang or the blunt end of the linear DNA product. The signal may be measured by flow cytometry and/or fluorescence-activated cell sorting.

The functional portion may also facilitate DNA sequencing. For example, the functional portion may be a sequencing adapter. The term "sequencing adapter" is intended to encompass one or more nucleic acid domains that include at least a portion of a nucleic acid sequence (or complement thereof) utilized by a sequencing platform of interest, such as a sequencing platform provided by Illumina@(e.g. the HiSeq™, MiSeq™ and/or Genome Analyzer™ sequencing systems), Oxford Nanopore™ Technologies (e.g. the MinION sequencing system), Ion Torrent™ (e.g. the Ion PGM™ and/or Ion Proton™ sequencing systems), Pacific Biosciences (e.g. the PACBIO RS II sequencing system); Life Technologies™ (e.g. a SOLiD sequencing system), Roche (e.g. the 454 GS FLX+ and/or GS Junior sequencing systems), or any other sequencing platform of interest.

An example of the method is provided with reference to FIG. 3, which illustrates the workflow to obtain the linear DNA product by digestion and ligation of adaptor molecules in a single step, starting from amplified DNA obtained through rolling circle amplification of a circular DNA template generated through the action of Cre recombinase on substrates containing two LoxP sequences flanking the DNA of interest in the same direction.

The method is further described with reference to FIG. 4, which illustrates the sequences driving adaptor molecule ligation after BsaI digestion of amplified double-stranded DNA molecule in each cycle of the process. BsaI digestion produces 4-nucleotide protruding ends at 5' (TCCC 5') at both sides of the expression cassette. The adaptor molecules are ligated at both sides of the expression cassette, resulting in a linear protected DNA product due to the presence of protected nucleotides (marked with asterisk) at both sides and both strands of the expression cassette, which prevents exonuclease degradation of the linear DNA product.

3. Methods for Producing a Partially Closed Linear DNA Product Comprising Nuclease-Resistant Nucleotides The methods described herein may be used to produce a partially closed linear DNA product comprising nuclease-resistant (i.e. protected nucleotides).

The invention provides a method for producing a partially closed deoxyribonucleic acid (DNA) product, wherein the method comprises:

(a) contacting a double-stranded DNA molecule with an endonuclease and first and second adaptor molecules to form a single contiguous aqueous volume; and (b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first adaptor molecule is a nucleic acid molecule that comprises one or more nuclease-resistant nucleotides (i.e. protected nucleotides) and wherein the linear double-stranded region is closed at the second end by the second adaptor molecule.

The step of contacting the double-stranded DNA molecule with the endonuclease and first and second adaptor molecules is preferably performed in the presence of a ligase. Thus, the method for producing a partially closed linear DNA product may comprise the steps:

(a) contacting a double-stranded DNA molecule with an endonuclease, a ligase and first and second adaptor molecules to form a single contiguous aqueous volume; and (b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first adaptor molecule is a nucleic acid molecule that comprises one or more nuclease-resistant nucleotides (i.e. protected nucleotides) and wherein the linear double-stranded region is closed at the second end by the second adaptor molecule.

The partially closed linear DNA product produced by the methods described herein has enhanced resistance to nuclease (e.g. exonuclease) digestion.

The appending of the first adaptor molecule and/or the second adaptor molecule may be performed by hybridization or ligation of the adaptor molecules to the ends of the linear double-stranded region. Thus, the first adaptor molecule may be hybridized to the first end of the linear double-stranded region. The second adaptor molecule may be hybridized to the second end of the linear double-stranded region. The first adaptor molecule may be ligated to the first end of the linear double-stranded region. The second adaptor molecule may be ligated to the second end of the linear double-stranded region. The appending of the first adaptor molecule and the second adaptor molecule may be performed by both hybridization and ligation of the adaptor molecules to the ends of the linear double-stranded region. Thus, the first adaptor molecule may be hybridized and ligated to the first end of the linear double-stranded region. The second adaptor molecule may be hybridized and ligated to the second end of the linear double-stranded region. The hybridization is based on complementarity of a portion of the first and/or second adaptor molecules to the first and/or second end of the linear double-stranded region.

The method for producing a partially closed linear DNA product may comprise the steps:

(a) contacting a double-stranded DNA molecule with an endonuclease, a ligase and first and second adaptor molecules to form a single contiguous aqueous volume; and (b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprises one or more nuclease-resistant nucleotides (i.e. protected nucleotides), and wherein the linear double-stranded region is closed at the second end by the second adaptor molecule.

The method for producing a partially closed linear DNA product may comprise the steps:

(a) contacting a double-stranded DNA molecule with an endonuclease, a ligase and first and second adaptor molecules to form a single contiguous aqueous volume; and (b) incubating the single contiguous aqueous volume to generate the partially closed linear DNA product, wherein the partially closed linear DNA product comprises a linear portion of the double-stranded DNA molecule, and wherein the first adaptor molecule is ligated to a first end of the linear portion of the double-stranded DNA molecule and the second adaptor molecule is ligated to a second end of the linear portion of the double-stranded DNA molecule, and wherein the first adaptor molecule is a nucleic acid molecule that comprises one or more nuclease-resistant nucleotides (i.e. protected nucleotides), and wherein the linear double-stranded region is closed at the second end by the second adaptor molecule.

As used herein, the term "complementary" refers to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence.

Preferably, the step of contacting the double-stranded DNA molecule with the endonuclease, the ligase and first and second adaptor molecules is performed in a single reaction (i.e. a single step).

The step of incubating the single contiguous aqueous volume to generate the partially closed linear DNA product may comprise generating the linear portion of the double-stranded DNA molecule by digesting the double-stranded DNA molecule with the endonuclease.

The step of incubating the single contiguous aqueous volume may be performed under conditions that promote appending (or linking) of the first and second adaptor molecules to the linear double-stranded region to produce the partially closed linear DNA product. The appending may be performed by creating a covalent link between the first and/or second adaptor molecule and the end(s) of the linear double-stranded region (or linear portion of the double-stranded DNA molecule).

The step of incubating the single contiguous aqueous volume may be performed under conditions that promote digestion of the double-stranded DNA molecule to produce the linear portion of the double-stranded DNA molecule. The digestion of the double-stranded DNA molecule to produce the linear portion of the double-stranded DNA molecule may be performed at a first temperature of 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or at about 37° C. The digestion may be endonuclease digestion, preferably Type IIS endonuclease digestion.

The step of incubating the single contiguous aqueous volume may be performed under conditions that promote ligation of the linear double-stranded region to the first and second adaptor molecules. The ligation may be at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% efficient. For example, at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% of the linear double-stranded regions (or the portions of the double-stranded DNA molecules) may be incorporated into closed linear DNA products. Preferably, the ligation is at least 15% efficient.

The step of ligation of the linear double-stranded region to the first and second adaptor molecules may be performed at a second temperature of 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C.

The step of incubating the single contiguous aqueous volume may comprise incubating at a first temperature and then incubating at a second temperature. The first temperature may be 1° C.-100° C., 1° C.-80° C., 5° C.-70° C., 10° C.-60° C., 15° C.-55° C., 20° C.-50° C., 25° C.-45° C., 30° C.-40° C., 35° C.-39° C., 36° C.-38° C., or about 37° C. The second temperature may be 1° C.-90° C., 2° C.-70° C., 5° C.-60° C., 8° C.-55° C., 9° C.-50° C., 10° C.-45° C., 11° C.-40° C., 12° C.-37° C., 13° C.-30° C., 14° C.-25° C., 15° C.-20° C. or at about 16° C. Preferably, the first temperature is 35° C.-39° C. Preferably, the second temperature is 14° C.-18° C.

The step of incubating the single contiguous aqueous volume may comprise cycling between the first temperature and the second temperature. The step of incubating the single contiguous aqueous volume may comprise cycling between the first temperature and the second temperature at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 80, at least 90, or at least 100 times, preferably at least 20 times. The step of incubating the single contiguous aqueous volume may comprise cycling between the first temperature and the second temperature less than 40, less than 35, less than 30 times, less than 29, less than 25 times. The step of incubating the single contiguous aqueous volume may comprise cycling between the first temperature and the second temperature 2-100, 5-80, 10-70, 20-60, or 30-60 times. The step of incubating the single contiguous aqueous volume may comprise cycling between the first temperature and the second temperature 2-20, 5-29, 61-100, or 65-80 times.

The step of incubating the single contiguous aqueous volume may be performed isothermally. The step of incubating the single contiguous aqueous volume may comprise incubating at a constant temperature. The constant temperature promotes simultaneous digestion of the double-stranded DNA molecule to produce the linear portion of the double-stranded DNA molecule and ligation of the linear double-stranded region to the first and second adaptor molecules. For example, the constant temperature may be 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. Preferably, the constant temperature is 30° C. The constant temperature is intended to mean that the temperature does not significantly change during the reaction. The constant temperature is intended to mean that the temperature variation during the step of incubating the single contiguous aqueous volume is less than 10° C., less than 9° C., less than 8° C., less than 7° C., less than 6° C., less than 5° C., less than 4° C., less than 3° C., less than 2° C., or less than 1° C. In a preferred embodiment the temperature during the step of incubating the single contiguous aqueous does not deviate by more than 5° C., preferably by not more than 3° C., even more preferably not more than 1° C. Thus, the constant temperature may be a temperature in a range of 20° C.-30° C., 22° C.-32° C., 24° C.-34° C., 26° C.-36° C., 28° C.-38° C., 30° C.-40° C., 22° C.-28° C., 32° C.-38° C., 25° C.-35° C., 26° C.-34° C., 27° C.-33° C., 27.5° C.-32.5° C., 28° C.-32° C., 28.5° C.-31.5° C., 29° C.-31° C., or 29.5° C.-30.5° C. Preferably, the constant temperature is a temperature in a range of 27.5° C.-32.5° C. Alternatively, the constant temperature may be a temperature in a range of 32° C.-42° C., 33° C.-41° C., 34° C.-40° C., 35° C.-39° C., 36° C.-38° C. Preferably, the constant temperature is a temperature in a range of 34.5° C.-39.5° C.

The first and second adaptor molecules may comprise one or more phosphorothioated nucleotides, such that, once the adaptor molecules are appended (e.g. ligated) to the linear double-stranded region, the partially closed linear DNA product is resistant to nuclease digestion or has improved or enhanced resistance to nuclease digestion. The partially closed linear DNA product may be resistant to 3'-end exonuclease digestion (e.g. by exonuclease III) and/or 5'-end exonuclease digestion (e.g. by exonuclease VIII).

The adaptor molecule may comprise a plurality of phosphorothioated nucleotides. For example, the adaptor molecules may comprise at least 2, at least 3, at least 4, at least 5, at least 6, at least 7, at least 8, at least 9, at least 10, at least 11, at least 12, at least 13, at least 14, at least 15 or at least 16 phosphorothioated nucleotides in each strand.

The adaptor molecule may be a nucleic acid adaptor molecule. The adaptor molecule may be double-stranded. The adaptor molecule may comprise a portion that is double-stranded.

The first and/or second adaptor molecules may comprise at least 3, at least 4, at least 5, at least 6, at least 7, at least 8, at least 9, at least 10, at least 11, at least 12, at least 13, at least 14, at least 15, or at least 16 base pairs.

The adaptor molecule may comprise a plurality of phosphorothioated nucleotides in each strand. For example, the adaptor molecules may comprise at least 2, at least 3, at least 4, at least 5, at least 6, at least 7, at least 8, at least 9, at least 10, at least 11, at least 12, at least 13, at least 14, at least 15 or at least 16 phosphorothioated nucleotides in each strand.

The adaptor molecule may comprise a plurality of phosphorothioated nucleotides at internal positions in each strand. For example, the adaptor molecules may comprise at least 1, at least 2, at least 3, at least 4, at least 5, at least 6, at least 7, at least 8, at least 9, at least 10, at least 11, at least 12, at least 13, at least 14, at least 15 or at least 16 phosphorothioated nucleotides at internal positions in each strand. Preferably, the adaptor molecule comprises at least 2 phosphorothioated nucleotides at internal positions in each strand.

The internal positions may not be located between the second and penultimate nucleotide of the adaptor molecule. The internal positions may be any position in the adaptor molecules other than the last nucleotide at the end of each strand.

The adaptor molecule may comprise at least 5%, at least 10%, at least 20%, at least 30%, at least 40%, at least 50%, at least 60%, at least 70%, at least 80%, at least 90%, at least 95%, or at least 100% of protected nucleotides.

Once the adaptor molecules are appended to the linear double-stranded region, the partially closed linear DNA product may comprise a protected nucleotide (e.g. phosphorothioated nucleotide) at the 5'-end (or at the 5'-end region) of one or both strands. Preferably, the partially closed linear DNA product comprises a phosphorothioated nucleotide at the 5'-end (or at the 5'-end region) of one strand. The partially closed linear DNA product may comprise a phosphorothioated nucleotide at the 5'-end (or at the 5'-end region) of one strand. As most exonucleases, for example exonuclease III, remove nucleotides from the 3'-end of the polynucleotide chain, the linear DNA product may comprise a protected nucleotide at the 3'-end (or at the 3'-end region) of one strand. Preferably, the partially closed linear DNA product comprises a phosphorothioated nucleotide at the 3'-end (or the 3'-end region) of one strand. The partially closed linear DNA product may comprise at least one phosphorothioated nucleotide at the 3'-end (or the 3'-end region) and at least one phosphorothioated nucleotide at the 5'-end (or the 5'-end region) of one strand. The partially closed linear DNA product may comprise at least one phosphorothioated nucleotide at the 3'-end (or the 3'-end region) of the sense strand and the 5'-end (or the 5'-end region) if the antisense strand. The partially closed linear DNA product may comprise at least one phosphorothioated nucleotide at the 5'-end (or the 5'-end region) of the sense strand and the 3'-end (or the 3'-end region) if the antisense strand. Thus, both the sense and antisense strands in the double stranded partially closed linear DNA product may be protected from nuclease digestion by using nuclease-resistant nucleotides at one end of the partially closed linear DNA product.

One of the adaptor molecules used in the methods described herein may comprise a self-complementary element which creates a loop, such as a hairpin loop or a stem loop. Thus, the one of the adaptor molecules may comprise a hairpin or a stem-loop. The adaptor molecule may comprise a double-stranded portion comprising a sense strand and an antisense strand, wherein the sense strand and the antisense strand are linked together in a hairpin such that the sense strand is hybridized to the antisense strand. The double-stranded portion of an adaptor may comprise a 3' overhang or a 5' overhang of at least 1, at least 2, at least 3, at least 4, or at least 5 nucleotides. Preferably the 3' overhang or the 5' overhang is 4-8 nucleotides. Each end of the linear double-stranded region (or linear portion of the double-stranded DNA molecule) may comprise a 3' or a 5' overhang. A portion of the adaptor molecule (e.g. the overhang) may be complementary to the first end or the second end of the linear double-stranded region.

The method described herein may use a first adaptor molecule which is a linear nucleic acid molecule comprising nuclease-resistant nucleotides and a second adaptor molecule which comprises hairpin loop or stem loop, or any other structure which is able to close one end of the linear DNA molecule to produce a partially closed linear DNA product.

The partially closed linear DNA product may be a partially covalently closed DNA product. Thus, in embodiments where the adaptor molecules comprise a loop (e.g. a hairpin), the adaptor molecule closes one end of the linear double-stranded region forming a partially covalently closed DNA product.

The adaptor molecule may comprise a single-stranded portion. The single-stranded portion may form a hairpin or a stem-loop. The single-stranded portion may comprise less than 10, 9, 8, 7, 6, 5, 4, 3, 2 nucleotides. Preferably, the single-stranded portion comprises 5 nucleotides.

The partially closed linear DNA product may additionally comprise a plurality of protected nucleotides (e.g. phosphorothioated nucleotides) at internal positions in each strand. For example, the linear DNA product may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, or at least 500 protected nucleotides (e.g. phosphorothioated nucleotides) at internal positions in each strand. Preferably, the partially closed linear DNA product comprises at least 2 protected nucleotides (e.g. phosphorothioated nucleotides) at internal positions in each strand.

The internal positions may not be located between the second and penultimate nucleotide of the partially closed linear DNA product. The internal positions may be any position in the adaptor molecules other than the last nucleotide at the end of each strand.

The linear double-stranded region (or linear portion of the double-stranded molecule) may comprise a plurality of phosphorothioated nucleotides at internal positions in each strand. For example, the linear double-stranded region (or linear portion of the double-stranded molecule) may comprise at least 2, at least 4, at least 6, at least 8, at least 10, at least 12, at least 14, at least 16, at least 18, at least 20, at least 30, at least 40, at least 50, at least 60, at least 70, at least 80, at least 90, at least 100, at least 125, at least 150, at least 175, at least 200, at least 250, at least 300, at least 350, at least 400, at least 450, or at least 500 protected nucleotides (e.g. phosphorothioated nucleotides) at internal positions in each strand. Preferably, the linear double-stranded region (or linear portion of the double-stranded molecule) comprises at least 2 protected nucleotides (e.g. phosphorothioated nucleotides) at internal positions in each strand. The internal positions may not be located between the second and penultimate nucleotide of the linear double-stranded region (or linear portion of the double-stranded molecule).

The nucleotides resistant to exonuclease digestion (i.e. protected nucleotides) may be phosphorothioated nucleotides of at least one type. For example, the at least one type of phosphorothioated nucleotides is α-S-dATP (i.e. 2'-deoxyadenosine-5'-(α-thio)-triphosphate), α-S-dCTP (i.e. 2'-deoxycytidine-5'-(α-thio)-triphosphate), α-S-dGTP (i.e. 2'-deoxyguanosine-5'-(α-thio)-triphosphate), α-S-dTTP (i.e. 2'-deoxythymidine-5'-(α-thio)-triphosphate), α-S-dUTP (i.e. 2'-deoxyuridine-5'-(α-thio)-triphosphate), and/or uridine 2', 3'-cyclophosphorothioate.

The adaptor molecules may comprise at least two types of phosphorothioated nucleotides. For example, the at least two types of phosphorothioated nucleotides are: α-S-dATP and α-S-dCTP, α-S-dATP and α-S-dGTP, α-S-dATP and α-S-dTTP, α-S-dCTP and α-S-dGTP, α-S-dCTP and α-S-dTTP, or α-S-dGTP and α-S-dTTP.

The adaptor molecules may comprise at least three types of phosphorothioated nucleotides. For example, the at least three types of phosphorothioated nucleotides are:

(e) α-S-dATP, α-S-dCTP and α-S-dGTP;
(f) α-S-dATP, α-S-dCTP and α-S-dTTP;
(g) α-S-dATP, α-S-dGTP and α-S-dTTP; or
(h) α-S-dCTP, α-S-dGTP and α-S-dTTP.

The adaptor molecules may comprise at least four types of phosphorothioated nucleotides. For example, the at least four types of protected nucleotides are α-S-dATP, α-S-dCTP, α-S-dGTP and α-S-dTTP.

The phosphorothioated nucleotides may be Sp-isomers, Rp-isomers or a mixture of both Sp- and Rp-isomers.

The nucleotides resistant to exonuclease digestion (i.e. protected nucleotides) may be MOE nucleotides of at least one type, or at least two, three or four types. For example, the MOE nucleotides may be 2'-O-methoxy-ethyl guanosine, 2'-O-methoxy-ethyl cytidine, 2'-O-methoxy-ethyl adenosine, and/or 2'-O-methoxy-ethyl thymidine.

The method may further comprise, before step (a) (i.e. the step of contacting the double-stranded DNA molecule with the endonuclease, the ligase and the first and second adaptor molecules), a step of amplifying a DNA template molecule to produce the double-stranded DNA molecule. Thus, the invention provides a method for producing a partially closed linear DNA product, the method comprises:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume; and
(c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first adaptor molecule is a nucleic acid molecule that comprises one or more nuclease-resistant nucleotides (i.e. protected nucleotides) and wherein the linear double-stranded region is closed at the second end by the second adaptor molecule.

The step of amplifying may be performed by in vitro or in vivo amplification. Preferably, the step of amplifying is performed by in vitro amplification. For example, the step of amplifying may be performed by rolling circle amplification (RCA), MALBAC method, traditional polymerase chain reaction (PCR), nucleic acid sequence-based amplification (NASBA), loop-mediated isothermal amplification (LAMP), helicase-dependent amplification (HDA), multiple displacement amplification (MDA) and recombinase polymerase amplification (RPA). Preferably, the step of amplifying is performed by rolling circle amplification. Thus, the invention provides a method for producing a partially closed linear DNA product, the method comprises:

(a) amplifying a DNA template molecule comprising at least one cleavable (e.g. endonuclease) target sequence to generate a double-stranded DNA molecule, wherein the DNA template molecule is amplified by rolling circle amplification;
(b) contacting the double-stranded DNA molecule with an endonuclease, a ligase and first and second adaptor molecules to form a single contiguous aqueous volume; and
(c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first adaptor molecule is a nucleic acid molecule that comprises one or more nuclease-resistant nucleotides (i.e. protected nucleotides) and wherein the linear double-stranded region is closed at the second end by the second adaptor molecule.

Rolling circle amplification may be performed without any primers, or in the presence of a primer or multiple primers. For example, the primer may be a synthetic primer. The primers may be random primers. Rolling circle amplification may be performed in the presence of a primase. The primase may be TthPrimPol. Preferably, if the rolling circle amplification is performed without any primers, it is performed in the presence of a primase, such as TthPrimPol. Similarly, if a primer is used during amplification reaction, a primase is not used. The double-stranded DNA product may be generated by the rolling circle amplification in vitro under isothermal conditions using a suitable nucleic acid polymerase, such as Phi29 DNA polymerase.

In the methods described herein, the DNA template molecule may comprise at least one cleavable target sequence. The cleavable target sequence may be an endonuclease target sequence. Thus, the DNA template molecule may comprise at least one endonuclease target sequence. Preferably, the DNA template molecule comprises at least two endonuclease target sequences. The endonuclease target sequences may be the same or different. Preferably, the at least one endonuclease target sequence is a restriction endonuclease target sequence. Different restriction endonuclease target sequences would be known to the skilled person. The cleavable target sequence may be a Type IIS restriction endonuclease target sequence. For example, the restriction endonuclease target sequence may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequence. The at least one cleavable sequence (e.g. endonuclease target sequence) may be a native cleavable sequence (i.e. a cleavable sequence present in the template molecule). Alternatively, the at least one cleavable sequence (e.g. endonuclease target sequence) may be introduced to the DNA template molecule prior to the production of the partially closed linear DNA product.

The endonuclease may be a restriction enzyme endonuclease. The endonuclease may be a Type IIS restriction enzyme. The endonuclease may be any enzyme that recognizes a DNA sequence and cleaves outside of the recognition sequence. For example, the endonuclease may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction enzyme.

The ligase may be a DNA ligase, such as a T4 DNA ligase, T7 DNA ligase, mammalian DNA ligase I, III and IV; Taq DNA ligase, Tth DNA ligase, or *E. coli* DNA ligase.

The DNA template molecule used in the methods described herein may be single-stranded or double-stranded. Preferably, the DNA template molecule is double-stranded. The DNA template molecule may be a natural circular DNA molecule. For example, the DNA template molecule may be (i) a plasmid, (ii) a minicircle, (iii) a cosmid, (iv) a bacterial artificial chromosome (BAC), or (v) a molecular inversion probe (MIP). The DNA template molecule may be an enzymatically produced circular DNA molecule. For example, the DNA template molecule may be (i) a circular DNA molecule obtained from recombinase reaction, preferably Cre recombinase reaction, or (ii) a circular DNA molecule obtained from ligase reaction, preferably using the golden gate assembly. The DNA template molecule may be an enzymatically produced covalently-closed linear DNA molecule. For example, the DNA template molecule may be (i) a DNA molecule processed with TelN protelomerase; or (ii) a DNA molecule generated by ligation of the DNA ends with an adaptor. The DNA template molecule may comprise an element that is double-stranded and an element that is single-stranded. For example, the template DNA molecule may comprise a double-stranded DNA and a single-stranded hairpin loop.

The DNA template molecule may be linear. If the DNA template molecule is linear, prior to amplification (e.g. rolling circle amplification), a DNA template molecule may be circularized to produce a DNA template molecule suitable for use in the methods described herein.

The template DNA molecule may comprise a cassette. The cassette may be a mammalian expression cassette. The cassette may further comprise a promoter. The promoter may be a CMV promoter. The cassette may further comprise an enhancer. The cassette may further comprise a reporter gene, such as an eGFP reporter gene or a luciferase reporter gene. The cassette may further comprise a homopolymeric sequence. The cassette may further comprise a LoxP sequence, preferably two LoxP sequences. If the two LoxP sequences are oriented in the same direction, the DNA sequence between the two LoxP sequences is excised as a circular loop of DNA. If the two LoxP sequences are oriented in the opposite direction, the DNA sequence between the two LoxP sequences is inverted. Thus, preferably, the two LoxP sequences are in the same orientation in the template DNA molecule.

The DNA template molecule may comprise a homopolymeric sequence at a 5'-end or a 3'-end or both a 5'-end and a 3'-end. The homopolymeric sequence may be added to the DNA template molecule before circularization. The homopolymeric sequence may be a polyA, a polyC, a polyG, or a polyT sequence. The homopolymeric sequence may be between 3-200 nucleotides in length. The homopolymeric sequence may be used to facilitate purification of the partially closed linear DNA product, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The method may further comprise, after the step of incubating the single contiguous aqueous volume, a step of purification of the partially closed linear DNA product.

The method may further comprise, after the step of incubating the single contiguous aqueous volume, a step of nuclease digestion. The nuclease digestion may be exonuclease digestion, such as exonuclease I and/or exonuclease III digestion. The step of nuclease digestion may take place before or after the step of purification. This step allows for removal of any double-stranded DNA molecules and/or adaptor molecules which have not been used in the course of performing the method. Thus, the method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule; and
(d) incubating the single contiguous aqueous volume with a nuclease (e.g. exonuclease).

The method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule;
(d) purifying the closed linear DNA product; and
(e) incubating the purified product of step (d) with a nuclease (e.g. exonuclease).

The method may comprise the steps:

(a) amplifying a DNA template molecule comprising at least one cleavable (e.g. endonuclease) target sequence to generate a double-stranded DNA molecule;
(b) contacting the double-stranded DNA molecule with an endonuclease, a ligase and first and second adaptor molecules to form a single contiguous aqueous volume;
(c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule;
(d) incubating the single contiguous aqueous volume with a nuclease (e.g. exonuclease); and
(e) purifying the closed linear DNA product.

The step of incubating the single contiguous aqueous volume (or the purified product of step (d)) with a nuclease may be performed at a temperature of 5-90° C., 10-80° C., 15-70° C., 20-60° C., 25-50° C., 30-45° C. or 35-40° C. The step of incubating the single contiguous aqueous volume (or the purified product of step (d)) with a nuclease may be performed for at least 10, at least 20, at least 30, at least 40, at least 50, or at least 60 min. The step of incubating the single contiguous aqueous volume (or the purified product of step (d)) may be performed at two different temperatures. For example, the step of incubating the single contiguous aqueous volume (or the purified product of step (d)) may be performed at 15-40° C. for 10-60 minutes followed by a temperature of 60-90° C. for 10-30 min. The higher temperature typically inactivates the nuclease (e.g. exonuclease). Thus, the method further provides a step of inactivating the nuclease (e.g. exonuclease). The step of incubating the single contiguous aqueous volume (or the purified product of step (d)) may be performed at 37° C. for 30 min and 80° C. for 20 min. Preferably, the step of inactivating the nuclease (e.g. exonuclease) is performed at a temperature of 70-80° C. The step of inactivating the nuclease (e.g. exonuclease) may be performed for at least 1, at least 5, at least 10, at least 20 or at least 30 minutes. Preferably, the step of inactivating the nuclease (e.g. exonuclease) is performed for at least 5 minutes.

The first adaptor molecule and/or the second adaptor molecule may comprise an overhang. The end of the linear double-stranded region may comprise a 3' or a 5' overhang. A portion of the first adaptor molecule (e.g. the overhang) may be complementary to the first end of the linear double-stranded region. A portion of the second adaptor molecule may be complementary to the second end of the linear double-stranded region.

The first end and the second end of the linear double-stranded region may be resistant to nuclease digestion. Preferably, the first end and the second end of the linear double-stranded region are resistant to the exonuclease digestion, such as exonuclease III digestion and/or exonuclease I digestion.

The linear DNA product may be partially double-stranded and/or partially single-stranded. The linear DNA product may comprise a portion that is double-stranded and a portion that is single-stranded.

The partially closed linear DNA product may comprise a cassette. The cassette may comprise a coding sequence. The coding sequence may encode a gene of interest, for example a gene encoding a protein. The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The partially closed linear DNA product may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long. The spacer may improve ligation efficiency of the first and second adaptor molecules to the linear double-stranded region. The spacer may improve a cell transfection yields.

The partially closed linear DNA product may comprise an inverted terminal repeat sequence.

The partially closed linear DNA product may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the partially closed linear DNA product is at least 50 base pairs long.

The double-stranded DNA molecule may be circular or branched.

The double-stranded DNA molecule may not comprise an adaptor molecule. The double-stranded DNA molecule may not comprise a hairpin, a loop or a stem-loop structure.

The double-stranded DNA molecule may comprise a cassette. The cassette may comprise a coding sequence. The coding sequence may encode a gene of interest, for example a gene encoding a protein. The cassette may comprise at least a portion of a promoter and a coding sequence. The cassette may comprise a promoter and a coding sequence. The cassette may comprise a promoter, a coding sequence, a ribosomal binding site and a translational termination sequence. The cassette may additionally comprise sequences aiding protein expression, such as a cap-independent translation element. The cassette may comprise (or encode) a repair template (or editing template). The repair template (or editing template) may be for use in CRISPR-Cas mediated homology directed repair (HDR). The cassette may encode CRISPR guide RNA. The cassette may be a mammalian expression cassette. The promoter may be a CMV promoter. The cassette may further comprise an enhancer. The cassette may further comprise a reporter gene, such as an eGFP reporter gene or a luciferase reporter gene. The cassette may further comprise a homopolymeric sequence, such as a polyA, poly C, polyT or polyG sequence. The homopolymeric sequence may be between 3-200 nucleotides in length. The homopolymeric sequence may be used to facilitate purification of the cassette, in which case, the homopolymeric sequence may be between 4-12 nucleotides in length, or between 5-10 nucleotides in length. The homopolymeric sequence may be used to improve mRNA expression, in which case, the homopolymeric sequence may be between 10-200 nucleotides in length, preferably between 80-150 nucleotides in length. The homopolymeric sequence may be at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 nucleotides in length. Preferably, the homopolymeric sequence is at least 100 nucleotides in length. More preferably still, the homopolymeric sequence is at least 120 nucleotides in length. For example, the homopolymeric sequence may comprise a polyA sequence of at least 120 nucleotides.

The double-stranded DNA molecule may comprise a spacer. The spacer may be at least 10, at least 20, at least 30, at least 40, at least 50, at least 60, at least 70, at least 80, at least 90, at least 100, at least 125, at least 150, at least 175, or at least 200 base pairs long. The spacer may improve an amplification yield of the double-stranded DNA molecule. The spacer may improve ligation efficiency of the first and second adaptor molecules to the linear double-stranded region. The spacer may improve a cell transfection yields.

The double-stranded DNA molecule may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The double-stranded DNA molecule may comprise one or more cleavable (e.g. endonuclease) target sequences. The double-stranded DNA molecule may comprise two cleavable (e.g. endonuclease) target sequences. The one or more endonuclease target sequences may be Type IIS endonuclease target sequences. The one or more endonuclease target sequences may be BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequences.

The double-stranded DNA molecule may be a product of amplification. Preferably, the amplification is rolling circle amplification.

The linear double-stranded region may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, the double-stranded DNA molecule is at least 50 base pairs long.

The linear double-stranded region may comprise a 3'-OH group at first and/or second ends. The 3'-OH group may facilitate ligation to the first and/or second adaptor molecule(s) (which may comprise a 5' phosphate). The linear double-stranded region may comprise a 5' phosphate at first and/or second ends. The 5' phosphate may facilitate ligation to the first and/or second adaptor molecule(s) (which may comprise a 3'-OH group).

The linear double-stranded region (e.g. the linear portion of the double-stranded molecule) may comprise an overhang. For example, the linear double-stranded region may comprise a 5' overhang or a 3' overhang. The linear double-stranded region may comprise a blunt end or blunt ends. The linear double-stranded region may comprise: a 5' overhang and a blunt end, two 5' overhangs, a 3' overhang and a blunt end, two 3' overhangs, or a 5' overhang and a 3' overhang. The overhang may have at least 3 nucleotides (preferably from 4 to 8 nucleotides). The overhang may be in the sense strand or the antisense strand of the linear double-stranded region.

The linear portion of the double-stranded DNA molecule (e.g. the linear portion of the double-stranded molecule) may be at least 50, at least 100, at least 250, at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 base pairs long. Preferably, double-stranded DNA molecule is at least 50 base pairs long.

The first adaptor molecule and/or the second adaptor molecule may be a synthetic adaptor molecule.

The first adaptor molecule and/or the second adaptor molecule may not be a plasmid or a vector DNA.

The adaptor molecule may comprise a double-stranded portion. The double-stranded portion may comprise less than 50, less than 45, less than 40, less than 35, less than 30, less than 25, less than 20, less than 15, or less than 10 base pairs. The double-stranded portion may comprise at least 5, at least 6, at least 7, at least 8, at least 9, at least 10, at least 11, at least 12, at least 13, at least 14, or at least 15 base pairs.

The adaptor molecule may comprise a 5' phosphate. The 5' phosphate may facilitate ligation to the linear double-stranded region.

The first adaptor molecule may comprise a portion that is complementary to the first end of the linear double-stranded region. The second adaptor molecule may comprise a portion that is complementary to the second end of the linear double-stranded region. The first adaptor molecule may comprise a portion that anneals to the first end of the linear double-stranded region. The second adaptor molecule may comprise a portion that anneals to the second end of the linear double-stranded region.

The first adaptor molecule and/or the second adaptor molecule may comprise an overhang. For example, the first adaptor molecule and/or the second adaptor molecule may comprise a 5' overhang or a 3' overhang. The first adaptor molecule and/or the second adaptor molecule may comprise a blunt end. The overhang may have at least 3 nucleotides (preferably from 4 to 6 nucleotides). The overhang of the first adaptor molecule and/or the second adaptor molecule may be complementary to the first and/or second end of the linear double-stranded region. The overhang of the first adaptor molecule and/or the second adaptor molecule may anneal to the first and/or second end of the linear double-stranded region.

The first adaptor molecule and/or the second adaptor molecule may not comprise a Type IIS endonuclease target sequence. The first adaptor molecule and/or the second adaptor molecule may not comprise BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI SapI target sequences.

The first adaptor molecule and/or the second adaptor molecule may comprise a functional portion. The functional portion may be a binding molecule, a targeting sequence, or a probe.

The functional portion may be a probe. As used herein, the term "probe" refers to a fragment of DNA, RNA or DNA/RNA chimera of variable length (e.g. 3-1000 bases long), which is used to detect the presence of target nucleotide sequences that are complementary to the sequence in the probe. Typically, the probe hybridizes to single-stranded nucleic acid whose base sequence allows probe-target base pairing due to complementarity between the probe and target. Thus, the functional portion may be a DNA sequence, a RNA sequence or a DNA/RNA chimera sequence. As used herein, the term "complementary" refers to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence.

The functional portion may be a binding molecule. The term "binding molecule" refers to any molecule capable of binding to the linear DNA product described herein and/or that is capable of binding to a further molecule or target. The binding molecule may be a protein, a polypeptide, or a peptide. The binding molecule may be an antibody, such as a monoclonal antibody or a polyclonal antibody. The binding molecule may be an antibody fragment.

The functional portion may facilitate detection of the DNA product by binding to capture molecules (e.g. capture antibodies bound by protein-protein interactions). The functional portion may bind to a cell target, for example, a cell receptor.

The functional portion may be a label. The 'label' can be any chemical entity which enable the detection of the double-stranded nucleic acid molecule via, physical, chemical and/or biological means. The label may be a chromophore, a fluorophore and/or a radioactive molecule.

The functional portion may be a targeting sequence. The targeting sequence may be a fragment of DNA or RNA of variable length, which is used to target the DNA product to a specific location in a cell. The targeting sequence may be used to increased transfection efficiency of non-viral gene delivery by virtue of enhanced nuclear import of the partially closed linear DNA product. For example, the targeting sequence may be a DNA nuclear targeting sequences (i.e. a recognition sequence for endogenous DNA-binding proteins), such as SV40 enhancer sequence (preferably downstream from the cassette).

To facilitate detection and/or quantification of the DNA product, the functional portion may comprise a fluorophore, a radioactive compound or a barcode.

A signal corresponding to the presence, absence and/or level of the partially closed linear DNA product may be measured using a barcode. The barcode may comprise at least one binding moiety linked to a barcoded portion, wherein the barcoded portion comprises at least one nucleotide (i.e. wherein the barcoded portion comprises a nucleotide sequence at least one nucleotide in length), and wherein the binding moiety is capable of binding to the 3' overhang, the 5' overhang or the blunt end of the partially closed linear DNA product. The binding moiety is capable of binding to 3' and/or 5' end of the partially closed linear DNA product. The signal may be measured by determining the presence, absence and/or level of the barcoded portion of the barcode (e.g. by sequencing or PCR). The barcoded portion may comprise at least 2, at least 3, at least 4, at least 5, at least 6, at least 7, at least 8, at least 9, or at least 10 nucleotides. The barcode may comprise at least 2 binding moieties (e.g. a first binding moiety and a second binding moiety). For example, the first binding moiety linked to the first barcoded portion may bind to the 3' end of the partially closed linear DNA product and/or the second binding moiety linked to the second barcoded portion may bind to the 5' end of the partially closed linear DNA product.

A signal corresponding to the presence, absence and/or level of the partially closed linear DNA product may be measured using a fluorophore (i.e. a fluorescently-labelled molecule), which is attached or bound to the 3' overhang, the 5' overhang or the blunt end of the partially closed linear DNA product. The signal may be measured by flow cytometry and/or fluorescence-activated cell sorting.

The functional portion may also facilitate DNA sequencing. For example, the functional portion may be a sequencing adapter. The term "sequencing adapter" is intended to encompass one or more nucleic acid domains that include at least a portion of a nucleic acid sequence (or complement thereof) utilized by a sequencing platform of interest, such as a sequencing platform provided by Illumina@(e.g. the HiSeq™, MiSeq™ and/or Genome Analyzer™ sequencing systems), Oxford Nanopore™ Technologies (e.g. the MinION sequencing system), Ion Torrent™ (e.g. the Ion PGM™ and/or Ion Proton™ sequencing systems), Pacific Biosciences (e.g. the PACBIO RS II sequencing system); Life Technologies™ (e.g. a SOLiD sequencing system), Roche (e.g. the 454 GS FLX+ and/or GS Junior sequencing systems), or any other sequencing platform of interest.

An example of the method is provided with reference to FIG. 17, which illustrates the workflow to obtain the partially closed linear DNA product by digestion and ligation of adaptor molecules in a single step, starting from amplified DNA obtained through rolling circle amplification of a circular DNA template generated through the action of Cre recombinase on substrates containing two LoxP sequences flanking the DNA of interest in the same direction.

The method is further described with reference to FIG. 18, which illustrates the sequences driving adaptor molecules ligation after BsaI digestion of an amplified double-stranded DNA molecule in each cycle of the process. BsaI digestion produces 4-nucleotide protruding ends at 5' (upstream TCCC 5' and downstream TTTT 5') at each sides of the expression cassette. Self-complementary adaptor molecules (SEQ ID NO: 4 containing a 4-nucleotide protruding end at 5' (GGGA 5') is then ligated at the upstream side of the expression cassette. Downstream adaptors are formed by hybridization of complementary oligonucleotides (SEQ ID NO:s 13 and 14) containing phosphorothioate internucleotide linkages (marked as asterisks) and forming a 4-nucleotide protruding end at 5' (AAAA 5'). Complementary adaptor molecules are ligated at each side of the expression cassette, resulting in partially closed linear DNA product which has enhanced resistance to exonuclease, since phosphorothioate internucleotide linkages at one sides of the expression cassette prevent exonucleolytic degradation of the partially closed linear DNA product.

4. Methods for Transcription and Protein Expression

The invention provides a method for in vitro transcription of a linear DNA product (e.g. a closed linear DNA product or a partially closed linear DNA product), wherein the method comprises contacting the linear DNA product (e.g. a closed linear DNA product or a partially closed linear DNA product), produced by the methods described herein, with a polymerase and producing a transcription product encoded by the linear DNA product (e.g. the closed linear DNA product or a partially closed linear DNA product).

The invention provides a method for in vitro transcription of a linear DNA product (e.g. a closed linear DNA product or a partially closed linear DNA product), wherein the method comprises:

(a) producing a linear DNA product (e.g. a closed linear DNA product or a partially closed linear DNA product) by any of the methods described herein;
(b) contacting the linear DNA product (e.g. the closed linear DNA product or a partially closed linear DNA product), with a polymerase; and
(c) producing a transcription product encoded by the linear DNA product (e.g. the closed linear DNA product or a partially closed linear DNA product).

The invention provides a method for in vitro transcription of a linear DNA product, wherein the method comprises:

(a) contacting a double-stranded DNA molecule with an endonuclease, a ligase and first and second adaptor molecules to form a single contiguous aqueous volume; and
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region; and
(c) contacting the linear DNA product with a polymerase; and
(d) producing a transcription product encoded by the linear DNA product.

The method may use adaptor molecules which generate a closed linear DNA product, such as adaptor molecules described herein. A method for in vitro transcription of a closed linear DNA product may comprise:

(a) contacting a double-stranded DNA molecule with an endonuclease, a ligase and first and second adaptor molecules to form a single contiguous aqueous volume;
(b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(c) contacting the closed linear DNA product with a polymerase; and
(d) producing a transcription product encoded by the closed linear DNA product.

The method may use adaptor molecules which comprise protected nucleotides, such as the adaptor molecules described herein. A method for in vitro transcription of a linear DNA product may comprise:

(a) contacting a double-stranded DNA molecule with an endonuclease, a ligase and first and second adaptor molecules to form a single contiguous aqueous volume;
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides (i.e. protected nucleotides);
(c) contacting the linear DNA product with a polymerase; and
(d) producing a transcription product encoded by the linear DNA product.

The method may use adaptor molecules which comprise protected nucleotides and adaptor molecules which comprise a hairpin or a stem loop, such as the adaptor molecules described herein.

A method for in vitro transcription of a partially closed linear DNA product may comprise:

(a) contacting a double-stranded DNA molecule with an endonuclease, a ligase and first and second adaptor molecules to form a single contiguous aqueous volume;
(b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule;
(c) contacting the partially closed linear DNA product with a polymerase; and
(d) producing a transcription product encoded by the partially closed linear DNA product.

The invention provides a method for producing a protein, wherein the method comprises introducing the linear DNA product (e.g. the closed linear DNA product or the partially closed linear DNA product), produced by the methods described herein, into a cell (e.g. a prokaryotic cell or a eukaryotic cell) or a cell-free expression system to generate a protein encoded by the linear DNA product (e.g. the closed linear DNA product or the partially closed linear DNA product).

The invention provides a method for producing a protein, wherein the method comprises:

(a) producing a linear DNA product (e.g. a closed linear DNA product or partially closed linear DNA product) by any of the methods described herein; and
(b) introducing the linear DNA product (e.g. the closed linear DNA product or partially closed linear DNA product) into a cell (e.g. a prokaryotic cell or a eukaryotic cell) or a cell-free expression system to generate a protein encoded by the linear DNA product (e.g. the closed linear DNA product or partially closed linear DNA product).

The invention provides a method for producing a protein comprising:

(a) contacting a double-stranded DNA molecule with an endonuclease, a ligase and first and second adaptor molecules to form a single contiguous aqueous volume; and
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region; and
(c) introducing the linear DNA product into a cell (e.g. a prokaryotic cell or a eukaryotic cell) or a cell-free expression system to generate a protein encoded by the linear DNA product.

The method may use adaptor molecules which generate a closed linear DNA product, such as adaptor molecules described herein. A method for producing a protein may comprise:

(a) contacting a double-stranded DNA molecule with an endonuclease, a ligase and first and second adaptor molecules to form a single contiguous aqueous volume;
(b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule; and
(c) introducing the closed linear DNA product into a cell (e.g. a prokaryotic cell or a eukaryotic cell) or a cell-free expression system to generate a protein encoded by the closed linear DNA product.

The method may use adaptor molecules which comprise protected nucleotides, such as the adaptor molecules described herein. A method for producing a protein may comprise:

(a) contacting a double-stranded DNA molecule with an endonuclease, a ligase and first and second adaptor molecules to form a single contiguous aqueous volume;
(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides (i.e. protected nucleotides); and (c) introducing the linear DNA product into a cell (e.g. a prokaryotic cell or a eukaryotic cell) or a cell-free expression system to generate a protein encoded by the linear DNA product.

The method may use adaptor molecules which generate a partially closed linear DNA product, such as adaptor molecules described herein. A method for producing a protein may comprise:

(a) contacting a double-stranded DNA molecule with an endonuclease, a ligase and first and second adaptor molecules to form a single contiguous aqueous volume;

(b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule; and (c) introducing the partially closed linear DNA product into a cell (e.g. a prokaryotic cell or a eukaryotic cell) or a cell-free expression system to generate a protein encoded by the partially closed linear DNA product.

The cell-free expression system may originate from (or be derived from) a prokaryotic cell or eukaryotic cell. For example, the cell-free expression system may originate from (or be derived from) rabbit reticulocytes, wheat germ or *Escherichia coli.*

The cell may be a prokaryotic cell or a eukaryotic cell. The cell may be an animal cell, such as mammal cell (e.g. a human cell), a fungal cell, a cell of a micro-organism (e.g. a prokaryotic cell or a eukaryotic cell), or a plant cell. Preferably, the cell is a human cell.

The linear DNA product or the closed linear DNA product may comprise a cassette. The desired protein might be encoded by the cassette.

The step of introducing the linear DNA product into a cell may be performed in vivo or in vitro.

The nuclease-resistant nucleotides (i.e. protected nucleotides) may be any protected nucleotides described herein.

5. Methods for Cell Transfection and Cell Transfection Compositions

The invention provides a method for cell transfection of a linear DNA product (e.g. a closed linear DNA product or a partially closed linear DNA product), produced by any of the methods described herein, into a cell.

The invention provides a method for cell transfection of a linear DNA product (e.g. a closed linear DNA product or a partially closed linear DNA product) into a cell, wherein the method comprises:

(a) producing a linear DNA product (e.g. a closed linear DNA product or a partially closed linear DNA product) by any of the methods described herein;

(b) contacting a cell with the linear DNA product (e.g. the closed linear DNA product or a partially closed linear DNA product); and (c) transfecting the linear DNA product (e.g. the closed linear DNA product or a partially closed linear DNA product) into the cytosol of the cell.

The invention provides a method for cell transfection of a linear DNA into a cell, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region;

(c) contacting the linear DNA product with the cell; and (d) transfecting the linear DNA product into the cytosol of the cell.

The method may use adaptor molecules which generate a closed linear DNA product, such as adaptor molecules described herein. A method for cell transfection of a closed linear DNA product into a cell may comprise:

(a) contacting a double-stranded DNA molecule with an endonuclease, a ligase and first and second adaptor molecules to form a single contiguous aqueous volume;

(b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(c) contacting the closed linear DNA product with the cell; and (d) transfecting the closed linear DNA product into the cytosol of the cell.

The method may use adaptor molecules which comprise protected nucleotides, such as the adaptor molecules described herein. A method for cell transfection of a linear DNA product into a cell may comprise:

(a) contacting a double-stranded DNA molecule with an endonuclease, a ligase and first and second adaptor molecules to form a single contiguous aqueous volume;

(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides (i.e. protected nucleotides);

(c) contacting the linear DNA product with the cell; and (d) transfecting the linear DNA product into the cytosol of the cell.

The method may use adaptor molecules which comprise protected nucleotides, such as the adaptor molecules described herein. A method for cell transfection of a partially closed linear DNA product into a cell may comprise:

(a) contacting a double-stranded DNA molecule with an endonuclease, a ligase and first and second adaptor molecules to form a single contiguous aqueous volume;
(b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule;
(c) contacting the partially closed linear DNA product with the cell; and
(d) transfecting the partially closed linear DNA product into the cytosol of the cell.

The invention provides a cell transfection composition comprising a linear DNA product (e.g. a closed linear DNA product) produced by (or obtainable by) the methods described herein.

The cell transfection composition may or may not comprise a carrier e.g. an agent or a formulation. Preferably, the carrier promotes accumulation of the linear DNA product at a target site and/or protects the linear DNA product from undesirable interactions with biological milieu components and/or protects the linear DNA product from metabolism and/or degradation.

The invention further provides a cell transfection method comprising contacting (in vitro) a cell to be transfected with a linear DNA product (e.g. a closed linear DNA product) produced by the methods of the invention, and wherein the linear DNA product (e.g. the closed linear DNA product) is transfected into the cytosol of the cell.

The cell or cells to be transfected may be provided in a cell culture medium (e.g. in a Petri dish, culture vessel or well, etc). The linear DNA product (e.g. the closed linear DNA product) may be added directly to the cell culture medium or the cells may be added to a solution, such as saline, a buffered solution or a cell culture medium, comprising the linear DNA product (e.g. the closed linear DNA product).

The carrier may be a viral carrier or a non-viral carrier. Viral carriers include a lentiviral vector, an adenoviral vector, a retroviral vector, or an adeno associate viral vector for delivery of the linear DNA product. Non-viral carriers (or vectors) include complexing the linear DNA product with a cationic agent such as a cationic cell penetrating peptide (CPP); a DNA-binding cationic component, such as a polylysine chain; a cationic polymer or dendrimer e.g. polyethylenimine (PEI), poly-D,L-lactide-co-glycolide (PLGA), and a block copolymer of PEG and polylysine, and/or a cationic lipid (e.g. lipofectamine).

The carrier may be a small molecule (e.g., cholesterol, bile acid, and/or lipid), polymer, protein (e.g. an antibody), and/or aptamer (e.g. RNA) that is conjugated to the linear DNA product. The carrier may be a nanoparticulate formulation used to encapsulate the linear DNA product (e.g. the closed linear DNA product).

The carrier may be a modification of the linear DNA product with a targeting ligand (e.g. an antibody), a peptide, a small molecule (e.g. folic acid and/or biotin), or a polymer present in extracellular matrix (e.g. hyaluronic acid and/or chondroitin sulphate), or a hydrophobic modification of the double-stranded nucleic acid molecule (e.g. using cholesterol and/or α-tocopherol).

The cell transfection composition may or may not comprise an agent selected from a photosensitizing agent and/or a radical initiator e.g. a photoinitiator. Preferably, this agent improves the function of the linear DNA product at a target site and/or protects the linear DNA product from metabolism and/or degradation.

The invention further provides a cell obtainable by the methods of the invention. Thus, the cell may comprise a linear DNA product (e.g. the closed linear DNA product) produced by the methods of the invention.

The invention further provides a cell transfected with a linear DNA product (e.g. the closed linear DNA product) produced by the methods of the invention.

The cell may be an animal cell, such as mammal cell (e.g. a human cell), a fungal cell, a cell of a micro-organism (e.g. a prokaryotic cell or a eukaryotic cell), or a plant cell. Preferably, the cell is a human cell.

The step of contacting the cell with a linear DNA product (e.g. the closed linear DNA product) may be performed in vivo. For example the linear DNA product (e.g. the closed linear DNA product) may be administered to an organism (e.g. a subject) in need thereof. The organism (e.g. the subject) may be an animal, such as mammal (e.g. a human), a fungus, a micro-organism, or a plant.

Any or all of the linear DNA products (e.g. the closed linear DNA products) described herein may be delivered to a cell via delivery particles such as liposomes, nanoparticles, exosomes, macrovesicles, viral or non-viral vectors. Any or all of the linear DNA products (e.g. the closed linear DNA products) described herein may be delivered to a cell using a gene-gun. Any or all of the linear DNA products (e.g. the closed linear DNA products) described herein may be delivered to a cell by electroporation. Any or all of the linear DNA products (e.g. the closed linear DNA products) described herein may be delivered to a cell by hydrodynamic needle. The linear DNA products (e.g. the closed linear DNA products) described herein may be delivered to a cell without a carrier.

The nanoparticle is preferably a self-assembled nanoparticle. The nanoparticle may be a nanoparticle which is produced by a process in which pre-existing components (e.g. a lipid component, a DNA product described herein) form an organized structure as a consequence of specific, local interactions among the components themselves, without external direction.

The DNA product and the lipid component may reversibly interact to form a self-assembled nanoparticle. The DNA product and the lipid component may reversibly interact in the self-assembled nanoparticle through intermolecular forces. The DNA product and the lipid component may reversibly interact in the self-assembled nanoparticle through non-covalent interactions. The DNA product and the lipid component may reversibly interact in the self-assembled nanoparticle through hydrogen bonds, van der Waals, hydrophobic, and/or electrostatic interactions. The DNA product and the lipid component may not be conjugated or linked by forces other than inter-molecular forces in the self-assembled nanoparticle.

6. Pharmaceutical Compositions and Methods for Producing Pharmaceutical Compositions The invention provides a pharmaceutical composition comprising a linear DNA product (e.g. a closed linear DNA product) described herein, and a pharmaceutically acceptable carrier or excipient.

The invention provides a pharmaceutical composition comprising a linear DNA product (e.g. a closed linear DNA product) produced by (or obtainable by) the methods described herein, and a pharmaceutically acceptable carrier or excipient.

The invention provides a method for producing a pharmaceutical composition comprising the linear DNA product, wherein the method comprises performing the method described herein and formulating the resulting linear DNA product with a pharmaceutically acceptable carrier or excipient.

The invention provides a method for producing a pharmaceutical composition, wherein the method comprises:

(a) producing a linear DNA product (e.g. a closed linear DNA product) by any of the methods described herein;

(b) formulating the linear DNA product (e.g. the closed linear DNA product) with a pharmaceutically acceptable carrier or excipient.

The invention provides a method for producing a pharmaceutical composition, wherein the method comprises:

(a) contacting a double-stranded DNA molecule with an endonuclease, a ligase and first and second adaptor molecules to form a single contiguous aqueous volume; and (b) incubating the single contiguous aqueous volume to generate a linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region; and (c) formulating the linear DNA product with a pharmaceutically acceptable carrier or excipient The method may use adaptor molecules which generate a closed linear DNA product, such as adaptor molecules described herein. A method for producing a pharmaceutical composition may comprise:

(a) contacting a double-stranded DNA molecule with an endonuclease, a ligase and first and second adaptor molecules to form a single contiguous aqueous volume;

(b) incubating the single contiguous aqueous volume to generate a closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule; and (c) formulating the closed linear DNA product with a pharmaceutically acceptable carrier or excipient.

The method may use adaptor molecules which comprise protected nucleotides, such as the adaptor molecules described herein. A method for producing a pharmaceutical composition may comprise:

(a) contacting a double-stranded DNA molecule with an endonuclease, a ligase and first and second adaptor molecules to form a single contiguous aqueous volume;

(b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides (i.e. protected nucleotides);

(c) formulating the linear DNA product with a pharmaceutically acceptable carrier or excipient.

The method may use adaptor molecules which generate a partially closed linear DNA product, such as adaptor molecules described herein. A method for producing a pharmaceutical composition may comprise:

(a) contacting a double-stranded DNA molecule with an endonuclease, a ligase and first and second adaptor molecules to form a single contiguous aqueous volume;

(b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule; and (c) formulating the partially closed linear DNA product with a pharmaceutically acceptable carrier or excipient.

The pharmaceutical composition may be formulated as pills, tablets or capsules combined with one or more pharmaceutically acceptable solid carriers or as a solution in one or more pharmaceutically acceptable solvents, or as an emulsion, suspension or dispersion in one or more pharmaceutically acceptable solvents or carriers. The formulation may also include other pharmaceutically acceptable excipients such as stabilizers, anti-oxidants, binders, colouring agents or emulsifying or taste-modifying agents and extended release formulations.

The pharmaceutical composition may be administered orally, topically, parenterally or transdermally or by inhalation. The pharmaceutical composition may be administered by injection or intravenous infusion using suitable sterile solutions. Topical dosage forms may be creams, ointments, patches, or similar vehicles suitable for transdermal and topical dosage forms.

The pharmaceutical composition may be dissolved or suspended in a liquid vehicle or formulated as a granule (a small particle or grain), a pellet (a small sterile solid mass consisting of a highly purified composition, with or without excipients, made by the formation of granules, or by compression and moulding), or a pellet coated extended release (a solid dosage form in which the composition itself is in the form of granules to which varying amounts of coating have been applied, and which releases the composition in such a manner to allow a reduction in dosing frequency as compared to that composition presented as a conventional dosage form).

Other forms of pharmaceutical compositions include pills (a small, round solid dosage form containing the composition intended for oral administration), powder (an intimate mixture of dry, finely divided composition with one or more pharmaceutically acceptable additives that may be intended for internal or external use), elixir (a clear, pleasantly flavoured, sweetened hydroalcoholic liquid containing dissolved composition; it is intended for oral use), chewing gum (a sweetened and flavoured insoluble plastic material of various shapes which when chewed, releases the composition into the oral cavity), syrup (an oral solution containing the composition and high concentrations of sucrose or other sugars; the term has also been used to include any other liquid dosage form prepared in a sweet and viscid vehicle, including oral suspensions), tablet (a solid dosage form containing the composition with or without suitable diluents), tablet chewable (a solid dosage form containing the composition with or without suitable diluents that is intended to be chewed, producing a pleasant tasting residue in the oral cavity that is easily swallowed and does not leave a bitter or unpleasant after-taste), tablet coated or tablet delayed release, tablet dispersible, tablet effervescent, tablet extended release, tablet film coated, or tablet film coated extended release where the tablet is formulated in such manner as to make the contained composition available over an extended period of time following ingestion.

In other forms of pharmaceutical compositions, a tablet for solution, tablet for suspension, tablet multilayer, tablet multilayer extended release may be provided, where the tablet is formulated in such manner as to allow at least a reduction in dosing frequency as compared to that composition presented as a conventional dosage form. A tablet orally disintegrating, tablet orally disintegrating delayed release, tablet soluble, tablet sugar coated, osmotic, and the like are also suitable.

The oral dosage form pharmaceutical composition may contain, in addition to the composition, one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer.

As used herein, injectable and infusion dosage forms include, but are not limited to, a liposomal injectable, which either consists of or forms liposomes (a lipid bilayer vesicle usually composed of phospholipids which is used to encapsulate the composition); an injection, which includes a sterile preparation intended for parenteral use; an emulsion injection, which includes an emulsion consisting of a sterile, pyrogen-free preparation intended to be administered parenterally; or a lipid complex injection.

For example, the linear DNA product (e.g. closed linear DNA product) can be administered by intratympanic injection (e.g. into the middle ear) and/or injections into the outer, middle, and/or inner ear. Such methods are routinely used in the art, for example, for the administration of steroids and antibiotics into human ears. Injection can be, for example, through the round window of the ear or through the cochlear capsule.

Other forms of pharmaceutical composition include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate the composition, either within a lipid bilayer or in an aqueous space) to be formed upon reconstitution; or a powder lyophilized for solution injection, wherein lyophilization ("freeze drying") is a process which involves the removal of water from products in the frozen state at extremely low pressures.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate the composition, either within a lipid bilayer or in an aqueous space) are formed. A suspension sonicated injection comprises a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

In another mode of administration, the pharmaceutical composition can be administered in situ, via a catheter or pump. A catheter or pump can, for example, direct the composition into the target location.

The parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. Formulations suitable for parenteral administration conveniently comprise a sterile oily or aqueous preparation of the composition which is preferably isotonic with the blood of the recipient but this is not essential.

As used herein, inhalation dosage forms include, but are not limited to, an aerosol (a product that is packaged under pressure and contains the composition which is released upon activation of an appropriate valve system intended for topical application to the skin as well as local application into the nose (nasal aerosols), mouth (lingual and sublingual aerosols), or lungs (inhalation aerosols)). A foam aerosol is a dosage form containing the composition, surfactants, aqueous or nonaqueous liquids, and propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. A metered aerosol is a pressurized dosage form consisting of metered dose valves which allow for the delivery of a uniform quantity of spray upon each activation. A powder aerosol is a product that is packaged under pressure and contains the composition, in the form of a powder that is released upon activation of an appropriate valve system. An aerosol spray is an aerosol product which utilizes a compressed gas as the propellant to provide the force necessary to expel the product as a wet spray and being applicable to solutions of the composition in aqueous solvent(s).

A transdermal dosage form may include, but is not limited to, a patch (a drug delivery system that often contains an adhesive backing that is usually applied to an external site on the body, whereby the ingredients (including the composition) either passively diffuse from, or are actively transported from, some portion of the patch, and whereby depending upon the patch, the ingredients (including the composition are either delivered to the outer surface of the body or into the body. Various types of transdermal patches such as matrix, reservoir and others are known in the art.

A topical dosage form may include various dosage forms known in the art such as lotions (an emulsion, liquid dosage form, whereby this dosage form is generally for external application to the skin), lotion augmented (a lotion dosage form that enhances composition delivery, whereby augmentation does not refer to the strength of the composition in the dosage form), gels (a semisolid dosage form that contains a gelling composition to provide stiffness to a solution or a colloidal dispersion, whereby the gel may contain suspended particles) and ointments (a semisolid dosage form, usually containing less than 20% water and volatiles and greater than 50% hydrocarbons, waxes, or polyols as the vehicle, whereby this dosage form is generally for external application to the skin or mucous membranes). Further embodiments include ointment augmented (an ointment dosage form that enhances composition delivery, whereby augmentation does not refer to the strength of the composition in the dosage form), creams (an emulsion, semisolid dosage form, usually containing greater than 20% water and volatiles and/or less than 50% hydrocarbons, waxes, or polyols may also be used as the vehicle, whereby this dosage form is generally for external application to the skin or mucous membranes) and cream augmented (a cream dosage form that enhances composition delivery, whereby augmentation does not refer to the strength of the composition in the dosage form). As used herein, an "emulsion" refers to a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable (e.g. cream, lotion, ointment). Further embodiments include suspensions (a liquid dosage form that contains solid particles dispersed in a liquid vehicle), suspension extended release, pastes (a semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), and powders.

The topical dosage form composition contains the composition and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer.

7. Linear DNA Products

The invention provides a linear DNA product (e.g. a closed linear DNA product) as described herein.

The invention provides a closed linear DNA product comprising a linear double-stranded region, wherein the linear double-stranded region comprises a linear portion of a double-stranded DNA molecule, and wherein the linear double-stranded region is closed at a first end by a first adaptor molecule and closed at a second end by the second adaptor molecule.

The invention provides a closed linear DNA product comprising a linear portion of a double-stranded DNA molecule, wherein the linear portion of the double-stranded DNA molecule is closed at a first end by a first adaptor molecule and closed at a second end by a second adaptor molecule.

The invention provides a linear DNA product comprising a linear double-stranded region, wherein the linear double-stranded region comprises a linear portion of a double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides.

The invention provides a linear DNA product comprising a linear portion of a double-stranded DNA molecule, wherein a first adaptor molecule is ligated to a first end of the linear portion of the double-stranded DNA molecule and the second adaptor molecule is ligated to a second end of the linear portion of the double-stranded DNA molecule, and wherein the first and second adaptor molecules are nucleic acid molecules that comprise one or more nuclease-resistant nucleotides.

The invention provides a partially closed linear DNA product comprising a linear portion of a double-stranded DNA molecule, wherein a first adaptor molecule is ligated to a first end of the linear portion of the double-stranded DNA molecule and the second adaptor molecule is ligated to a second end of the linear portion of the double-stranded DNA molecule, and wherein the first adaptor molecule is a nucleic acid molecule that comprise one or more nuclease-resistant nucleotides, and wherein the linear portion of the double-stranded DNA molecule is closed at the second end by the second adaptor molecule. Thus, the invention provides a partially closed linear DNA product which is closed (or covalently closed) at a second end and open at a first end. The partially closed linear DNA product comprises one or more nuclease-resistant nucleotides in the open-end region and/or at the first end. The open-end region may be at the 3' end or 5' end of the molecule.

The open-end region refers to at least 5, at least 10, at least 15, or at least 20 base pairs located closest to the open end of the DNA product. The partially closed linear DNA product may comprise one or more nuclease-resistant nucleotides in a sense and/or an antisense strand. Thus, for example, one or more nucleotides of the 20 base pairs located closest to the open end of the partially closed linear DNA product may be a nuclease-resistant nucleotide. Preferably, the partially closed linear DNA product comprises at least 5 nuclease-resistant nucleotides in the open-end region.

The partially closed linear DNA product may comprise a double-stranded DNA portion that is closed at a first end and open at a second end. The partially closed linear DNA product may comprise a double-stranded DNA portion that is closed at a first end by a single-stranded portion (i.e. it may comprise a first hairpin at the first end) and open at a second end. The partially closed linear DNA product may comprise one or more nuclease-resistant nucleotides in an open-end region adjacent to the second end. The open-end region adjacent to the second end may be at the 3' end or 5' end of the molecule. The open-end region adjacent to the second end may comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50 nucleotides located at the second end of the partially closed linear DNA product. This is to say that the open-end region adjacent to the second end may comprise any nucleotide between and including the end nucleotide of the second end and a nucleotide at location 2, 3, 4, 5, 6, 7, 8, 9, 10, 11, 12, 13, 14, 15, 16, 17, 18, 19, 20, 25, 30, 35, 40, 45, or 50 counting from the end nucleotide of the second end.

The open-end region adjacent to the second end may comprise a sense strand and an antisense strand. The open-end region adjacent to the second end may comprise one or more nuclease-resistant nucleotides in the sense strand or the antisense strand. The open-end region adjacent to the second end may comprise one or more nuclease-resistant nucleotides in both the sense and antisense strand. The open-end region adjacent to the second end may comprise two or more, three or more, four or more, or five or more nuclease-resistant nucleotides in both the sense and antisense strand. Preferably, the open-end region adjacent to the second end comprises five nuclease-resistant nucleotides in both the sense and antisense strand.

The partially closed linear DNA product may comprise a hairpin-loop at the 5' end or the 3' end. The partially closed linear DNA product may comprise a first adaptor molecule at a first end and a second adaptor molecule at a second end. The first adaptor molecule may comprise a hairpin and a second adaptor may comprise one or more protected nucleotides (i.e. nucleotides resistant to nuclease (e.g. exonuclease) digestion). The hairpin may confer resistance to nuclease (e.g. exonuclease) digestion. The presence of protected nucleotides may confer resistance to nuclease (e.g. exonuclease) digestion. The partially closed linear DNA product may be a DNA molecule having a double-stranded portion closed at a first end by ligation of a first adaptor (e.g. hairpin adaptor) to the first end and comprising at a second end a double stranded linear adaptor comprising protected nucleotides (i.e. nucleotides resistant to nuclease (e.g. exonuclease) digestion).

The partially closed linear DNA product may comprise (i) a cassette, wherein the cassette comprises a sense strand and an antisense strand; and (ii) one or more nuclease-resistant nucleotides in an open-end region of the partially closed linear DNA product, wherein the open-end region is 5' of the sense strand of the cassette. The partially closed linear DNA product may comprise (i) a cassette, wherein the cassette comprises a sense strand and an antisense strand; and (ii) one or more nuclease-resistant nucleotides in an open-end region of the partially closed linear DNA product, wherein the open-end region is 5' of the antisense strand of the cassette. The partially closed linear DNA product may comprise (i) a cassette, wherein the cassette comprises a sense strand and an antisense strand; and (ii) one or more nuclease-resistant nucleotides in an open-end region of the partially closed linear DNA product, wherein the open-end region is 3' of the sense strand of the cassette. The partially closed linear DNA product may comprise (i) a cassette, wherein the cassette comprises a sense strand and an antisense strand; and (ii) one or more nuclease-resistant nucleotides in an open-end region of the partially closed linear DNA product, wherein the open-end region is 3' of the antisense strand of the cassette.

The partially closed linear DNA product may comprise (i) a cassette, wherein the cassette comprises a sense strand and an antisense strand; (ii) one or more nuclease-resistant nucleotides in an open-end region of the partially closed linear DNA product, wherein the open-end region is 5' of the sense strand of the cassette; and (iii) one or more nuclease-resistant nucleotides in an open-end region of the partially closed linear DNA product, wherein the open-end region is 3' of the antisense strand of the cassette.

The partially closed linear DNA product may comprise (i) a cassette, wherein the cassette comprises a sense strand and an antisense strand; (ii) one or more nuclease-resistant nucleotides in an open-end region of the partially closed linear DNA, wherein the open-end region is 3' of the sense strand of the cassette; and (iii) one or more nuclease-resistant nucleotides in an open-end region of the partially closed linear DNA product, wherein the open-end region is 5' of the antisense strand of the cassette.

The closed linear DNA product, linear DNA product or partially closed linear DNA product may comprise a cassette, optionally a single cassette. The linear portion of a double-stranded DNA molecule (of a closed linear DNA product, linear DNA product or partially closed linear DNA product) may comprise a cassette, optionally a single cassette. Accordingly, the cassette (or single cassette) is located between the first and second adaptor molecules.

The term "single cassette" as used herein is intended to encompass a molecules that do not comprise or consist of a plurality of cassettes. That is to say that the closed linear DNA product, linear DNA product, or partially closed linear DNA product, comprises only a single cassette, which may comprise a single coding sequence of a gene of interest. The single cassette may not comprise or consist of a plurality of tandem repeat sequences, and/or concatemeric DNA. The term "single cassette" as used herein is intended to encompass a single copy of the DNA sequence of interest, for example, a single copy of the coding sequence. Thus, the "single cassette" may not encompass a cassette that comprises or consist of multiple copies of the same DNA sequence linked in series. The single cassette may comprise a collection of genes of interest. For example, the single cassette may comprise the sequence for at least two, three, four, or five genes of interest. The genes of interest may not be the same in a single cassette.

The invention provides a linear DNA product (e.g. a closed linear DNA product or a partially closed linear DNA product) obtainable by any of the methods described herein.

8. Uses and Applications

The invention provides a use of a linear DNA product (e.g. a closed linear DNA product) as described herein in the production of viral or non-viral delivery system.

The invention provides a use of a linear DNA product (e.g. a closed linear DNA product) in the production of viral or non-viral delivery system, wherein the linear DNA product (e.g. the closed linear DNA product) is produced by performing the method described herein.

The invention provides a viral or non-viral delivery system comprising a linear DNA product (e.g. a closed linear DNA product) as described herein. The invention provides a viral or non-viral delivery system comprising a linear DNA product (e.g. a closed linear DNA product), wherein the linear DNA product (e.g. the closed linear DNA product) is produced by performing the method described herein.

Viral Vectors

Methods of producing viral vectors, such as AAV vectors, are known in the art. The most widely used method involves the co-transfection of HEK293 by three bacterial plasmids. The first plasmid encodes the Rep and Cap element, the second plasmid is a helper plasmid, while the third plasmid encodes the genetic payload of interest with inverted terminal repeats (ITRs). There are several issues surrounding the use of plasmids for viral preparation (e.g. AAV), namely: 1) the production of the plasmids is time consuming and costly, 2) there is a difficulty in the propagation of ITR sequences in *E. coli;* 3) the incorporation of the plasmid backbone into the viral capsid (e.g. AAV capsid) might be challenging (e.g. issues with antibiotic resistance markers). Methods of producing viral vectors may be using other cell lines. For example, a cell line suitable for production of viral vectors may be a Vero cell, or any other stable cell line. Together these represent the main bottleneck in viral vector production (e.g. AAV production). Thus, the methods described herein provide a linear DNA product (e.g. a closed linear DNA product) suitable for use in production of viral vectors. The linear DNA product (e.g. the closed linear DNA product) overcomes the above issues with plasmid vectors.

The invention provides a method of producing a viral vector, the method comprising introducing the linear DNA product (e.g. a closed linear DNA product) produced by the methods described herein into a cell under conditions such that the viral vector is produced. The linear DNA product (e.g. the closed linear DNA product) may encode at least one element required for the production of the viral vector. For example, the linear DNA product (e.g. the closed linear DNA product) may encode Rep and/or Cap elements. The linear DNA product (e.g. the closed linear DNA product) may encode the helper plasmid elements. The linear DNA product (e.g. the closed linear DNA product) may encode Rep, Cap and helper plasmid elements. The linear DNA product (e.g. the closed linear DNA product) may encode a transgene. The method may be an in vivo or in vitro method. The cell may be an animal cell, preferably mammal cell, such as human cell (e.g. HEK293T, HEK293, CAP, CAP-T, or CHO). The cell may be a cell cultured in vitro in a tissue culture cell line.

Preferably, the vector is an AAV vector or lentivirus vector.

The invention also provides a method of delivering the viral vector (e.g. the closed linear DNA product) to a cell, comprising contacting the viral vector produced by the methods described herein with the cell. The cell may be an animal cell, preferably mammal cell, such as human cell.

The invention also provides a cell obtainable by the methods described herein.

Non-Viral Vectors

Methods of producing non-viral vectors, are known in the art. Use of non-viral vectors over viral vectors has several advantages, including the opportunity of repeat dosing due to their non-immunogenicity, an unlimited packaging capacity, and low associated toxicity. Most methods for producing non-viral vectors use plasmid DNA. Thus, the linear DNA product (e.g. a closed linear DNA product) produced by the methods described herein is suitable for use in production of non-viral vectors. The linear DNA product (e.g. the closed linear DNA product) produced by the methods of the invention overcomes the issues of using plasmid vectors in non-viral vector preparation. For example, the linear DNA product (e.g. the closed linear DNA product), unlike plasmid DNA, does not comprise a bacterial backbone, allowing more transgene copies per mg of DNA. In addition, the linear DNA product (e.g. the closed linear DNA product) does not comprise antibiotic resistant genes and bacterial contaminants. Moreover, the linear DNA product (e.g. the closed linear DNA product) provides a prolonged transgene expression (due to the presence of exonuclease-resistant nucleotides), and a more cost-effective process of non-viral vector production.

The invention provides a method of delivering the non-viral vector to a cell, comprising contacting the non-viral vector comprising the linear DNA product (e.g. a closed linear DNA product) with the cell. The cell may be an animal cell, preferably mammal cell, such as human cell.

The invention also provides a cell obtainable by the methods described herein.

General Therapeutic and Diagnostic Uses

The linear DNA product (e.g. a closed linear DNA product) produced by the methods described herein is particularly suitable for use in therapy. The invention provides a linear DNA product (e.g. a closed linear DNA product) as described herein for use in therapy. The invention provides a linear DNA product (e.g. a closed linear DNA product) obtainable by the method described herein for use in therapy. The linear DNA product (e.g. the closed linear DNA product) may encode a sequence of a therapeutic protein, a part of a vaccine, or an element of a genetic engineering mechanism, which is used to treat a disease or infection in a subject.

The invention further provides the linear DNA product (e.g. a closed linear DNA product) as described herein for use as a medicament. The invention further provides the linear DNA product (e.g. a closed linear DNA product) obtainable by the methods described herein for use as a medicament. The invention also provides the use of a linear DNA product (e.g. a closed linear DNA product) as described herein for the manufacture of a medicament for treating a disease. The invention also provides the use of a linear DNA product (e.g. a closed linear DNA product) obtainable by the methods described herein for the manufacture of a medicament for treating a disease.

The linear DNA product (e.g. the closed linear DNA product) may encode a sequence of a therapeutic protein, a part of a vaccine, or an element of a genetic engineering mechanism, which is used to treat a disease or infection in a subject.

The invention further provides the linear DNA product produced by the methods described herein for use in treating a disease.

The invention also provides a method of treating a disease in a subject comprising administering to the subject a linear DNA product (e.g. a closed linear DNA product) described herein. The invention also provides a method of treating a disease in a subject comprising administering to the subject the linear DNA product (e.g. a closed linear DNA product) obtainable by the methods described herein. Preferably, the amount of the linear DNA product administered to the subject is a therapeutic active amount.

The linear DNA product (e.g. the closed linear DNA product) described herein may be used to treat any disease or disorder. For example, the linear DNA product (e.g. the closed linear DNA product) may be used to treat one or more of the diseases and/or disorders selected from genetic disorders (e.g. monogenic disorders), cancer, HIV, other viral infections (e.g. infection caused by coronavirus (e.g. COVID-19), hepatitis A, hepatitis B, herpes simplex virus type 2, influenza, measles and/or respiratory syncytial virus), neurodegenerative diseases (e.g. Parkinson's disease and/or polyglutamine diseases such as Huntington's disease), ocular diseases (e.g. macular degeneration) and liver failure. Preferably, the linear DNA product (e.g. the closed linear DNA product) is used to treat a genetic disorder. More preferably still, the linear DNA product (e.g. the closed linear DNA product) is used to treat a monogenic disorder. For example, the linear DNA product (e.g. the closed linear DNA product), may be used to treat sickle cell anaemia, cystic fibrosis, Huntington disease, and Duchenne's Muscular Dystrophy, Haemophilia A, α1-antitrypsin deficiency, primary ciliary dyskinesia, or respiratory distress syndrome of prematurity.

A subject treated with the linear DNA product (e.g. a closed linear DNA product) may receive the linear DNA product (e.g. a closed linear DNA product) in the form of any of the pharmaceutical compositions described herein.

A subject treated with the linear DNA product (e.g. a closed linear DNA product) may receive the linear DNA product (e.g. the closed linear DNA product) in combination with other forms of treatment for the disorder concerned, including treatment with drugs generally used for the treatment of the disorder. The drugs may be administered in one or several dosage units. The skilled person (e.g. a medical practitioner) is well able to determine an appropriate dosage regimen for the subject according to the subject's specific circumstances.

As used herein, "administering" means introducing the linear DNA product into the subject's body as described in more detail above (see "Methods for producing a pharmaceutical composition"). Examples include but are not limited to oral, topical, buccal, sublingual, pulmonary, transdermal, transmucosal, as well as subcutaneous, intraperitoneal, intravenous, and intramuscular injection or in the form of liquid or solid doses via the alimentary canal.

As used herein, the phrase "a therapeutically active amount" means an amount of the linear DNA product that, when administered to a subject for treating a disease, is sufficient to effect such treatment of the disease. A "therapeutically active amount" will vary depending, for instance, on factors such as the specific product used, the severity of subject's disease, the age and relative health of the subject and the route and form of administration. Determining the relevant therapeutically active amount for a specific subject based on such factors is routine for the person skilled in the art (e.g. an attending medical practitioner). Treatment of a disease as described herein should be understood to mean an improvement in one of more of the symptoms of a disease.

The invention also provides the use of the linear DNA product (e.g. a closed linear DNA product) as described herein in a method of diagnosing a disease and/or a disorder. The invention also provides the use of the linear DNA product (e.g. the closed linear DNA product) obtainable by the methods described herein in a method of diagnosing a disease and/or a disorder.

The invention provides the use of the linear DNA product (e.g. the closed linear DNA product) in the "in vitro" diagnosis of a disease. The invention provides the use of the linear DNA product (e.g. the closed linear DNA product) obtainable by the methods described herein in the "in vitro" diagnosis of a disease.

The invention also provides the linear DNA product (e.g. the closed linear DNA product) for use in a method of diagnosis "in vivo" of a disease.

The method may be used to diagnose any disease and/or disorder. For example, the diseases and/or disorders may be selected from genetic disorders (e.g. monogenic disorders), cancer, HIV, other viral infections (e.g. infection caused by coronavirus (e.g. COVID-19), hepatitis A, hepatitis B, herpes simplex virus type 2, influenza, measles and/or respiratory syncytial virus), neurodegenerative diseases (e.g. Parkinson's disease and/or polyglutamine diseases such as Huntington's disease), ocular diseases (e.g. macular degeneration) and liver failure. Preferably, the linear DNA product is used to diagnose a genetic disorder. More preferably still, the linear DNA product is used to diagnose a monogenic disorder. For example, the linear DNA product may be used to diagnose sickle cell anaemia, cystic fibrosis, Huntington disease, and Duchenne's Muscular Dystrophy, Haemophilia A, α1-antitrypsin deficiency, primary ciliary dyskinesia, or respiratory distress syndrome of prematurity.

The diagnostic and treatment methods described herein may be in vitro methods or in vivo methods.

The method of diagnosis may rely on the detection and/or quantification of the linear DNA product (e.g. closed linear DNA product).

To facilitate detection and/or quantification of the linear DNA product, the linear DNA product (e.g. the closed linear DNA product) may be attached or bound to a functional portion. The functional portion may be any functional portion described herein. For example the functional portion may be a probe. The functional portion may comprise a fluorophore, a radioactive compound or a barcode. The functional portion may be a protein, for example, an antibody.

The diagnosis may rely on the detection of a signal corresponding to the presence, absence and/or level of the linear DNA product. For example, the signal may be measured by flow cytometry and/or fluorescence-activated cell sorting of a linear DNA product attached to a fluorescent probe.

The linear DNA product (e.g. the closed linear DNA product) may be detected by being bound to a capture moiety, for example in a lateral flow assay. In this example, the functional portion is a protein, for example, an antibody specific for the capture moiety. The capture of the antibody attached to the linear DNA product may produce a visual signal (e.g. a band of a different colour).

The invention also provides a method that combines diagnosis of a disease with a treatment of the disease.

Cell Therapy

The products produced by the methods of the invention may be substantially less contaminated than plasmid DNA. In addition, the products produced by the methods of the invention are very simple in nature (e.g. no bacterial backbone), which means that they are typically easy to work with. The pure and simple nature of the products described herein makes them particularly suitable for use in cell therapy. For example, a cell comprising the linear DNA product (e.g. the closed linear DNA product) may be injected or otherwise transplanted into a patient to cause a desired effect. The cell (or cells) may be capable of fighting cancer cells, for example, via cell-mediated immunity in the course of immunotherapy. The cell (or cells) may be grafted to regenerate diseased tissues.

The invention provides the linear DNA product (e.g. the closed linear DNA product) described herein for use in cell therapy. The invention provides the linear DNA product (e.g. the closed linear DNA product) obtainable by the methods described herein for use in cell therapy.

The invention provides the linear DNA product (e.g. the closed linear DNA product) described herein for use in cell therapy. The invention provides the linear DNA product (e.g.

the closed linear DNA product) obtainable by the methods described herein for use in cell therapy.

Preferably, cell therapy is ex-vivo cell therapy. The cell may be an animal cell, preferably mammal cell, such as human cell.

The invention also provides a cell obtainable by any methods described herein. For example, the cell may be suitable for use in cell therapy.

Vaccines

The linear DNA products (e.g. the closed linear DNA products) produced by the methods described herein are particularly suitable for use in vaccine production. A vaccine may comprise a linear DNA product (e.g. a closed linear DNA product) described herein. A vaccine may comprise a linear DNA product (e.g. a closed linear DNA product) obtainable by the methods described herein. Alternatively, the linear DNA product (e.g. the closed linear DNA product) may be used to produce a vaccine, preferably an mRNA-based vaccine. For example, vaccines such as the BioNTech and Moderna mRNA vaccines against COVID-19.

Thus, the invention provides the use of the linear DNA product (e.g. the closed linear DNA product) described herein in the production of a vaccine. The invention also provides the use of the linear DNA product (e.g. the closed linear DNA product) obtainable by the methods described herein in the production of a vaccine.

The linear DNA product (e.g. the closed linear DNA product) may encode an antigen, which may cause an immune response in a subject. The subject may be human. Preferably, the antigen is encoded on the cassette.

CAR-T Cells

The invention provides the use of a linear DNA product (e.g. the closed linear DNA product) described herein in the production of a CAR-T cell. The invention provides the use of the linear DNA product (e.g. the closed linear DNA product) obtainable by the methods described herein in the production of a CAR-T cell.

The invention provides a method for producing a genetically engineered CAR-T cell comprising: (a) introducing the linear DNA product (e.g. a closed linear DNA product) described herein into a T cell; and (b) expressing a gene of interest encoding by the linear DNA product (e.g. the closed linear DNA product). Preferably, the gene of interest is a tumour-specific CAR.

The invention provides a method for producing a genetically engineered CAR-T cell comprising: (a) introducing the linear DNA product (e.g. a closed linear DNA product) obtainable by the methods described herein into a T cell; and (b) expressing a gene of interest encoding by the linear DNA product (e.g. the closed linear DNA product). Preferably, the gene of interest is a tumour-specific CAR.

The method may further comprise, before step (a), a step of removing mononuclear cells from a patient. Preferably, the step of removing is performed using leukapheresis. Preferably the mononuclear cells are T cells. The method may further comprise, after step (b), a step of returning the genetically engineered cells to the patient.

The invention also provides an engineered T cell obtainable by any methods described herein. The engineered T cell may be suitable for use in CAR T-cell therapy.

CRISPR Delivery

The products produced by the methods described herein are particularly suitable for use in delivery of CRISPR machinery to cells, for example in cell therapy or in vivo therapy.

Various different cargos and delivery vehicles are used commonly for delivery of CRISPR machinery, including physical delivery methods (e.g. microinjection; electroporation), viral delivery methods (e.g. adeno-associated virus (AAV); full-sized adenovirus and lentivirus), and non-viral delivery methods (e.g. liposomes; polyplexes; gold particles).

The linear DNA product (e.g. the closed linear DNA product) may comprise a gene sequence encoding any component of the CRIPSR machinery. The linear DNA product (e.g. the closed linear DNA product) may encode all components of the CRIPSR machinery.

The linear DNA product (e.g. the closed linear DNA product) may comprise (or encode) a repair template (or editing template). The repair template (or editing template) may be for editing genomes, for example, using the CRISPR-Cas system. The repair template (or editing template) may comprise or consist of a homology region (e.g. homology arm) which is homologous to the desired DNA region (i.e. target molecule). The repair template (or editing template) may be for use in CRISPR-Cas mediated homology directed repair (HDR). The repair template (or editing template) may be used to repair a target molecule having a strand break (e.g. a single stranded break or a double stranded break). The strand break may be created by a nuclease of the CRISPR system (e.g. Cas9, Cpf1, or MAD7). The repair template (or editing template) may introduce at least one mutation (e.g. an insertion, deletion, and/or substitution) in the desired DNA region (i.e. target molecule). The repair template (or editing template) may be at least 10, 20, 30, 40, 50, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, or 10000 base pairs long. The linear DNA product (e.g. the closed linear DNA product) encoding the repair template may be delivered to a cell by a nanoparticle, a non-viral vector or a viral vector, or without the aid of any carrier. The linear DNA product (e.g. the closed linear DNA product) encoding the repair template may be delivered to a cell by electroporation. The linear DNA product (e.g. the closed linear DNA product) encoding the repair template may be delivered to a cell by hydrodynamic needle.

The linear DNA product (e.g. the closed linear DNA product) may comprise (or further comprise) a gene sequence encoding a nuclease protein of a CRISPR system (e.g. Cas9, Cpf1, or MAD7), and/or a guide RNA. The linear DNA product (e.g. the closed linear DNA product) may comprise (or further comprise) a gene sequence encoding a nuclease protein of a CRISPR system (e.g. Cas9, Cpf1, or MAD7). The linear DNA product (e.g. the closed linear DNA product) may comprise (or further comprise) a gene sequence encoding a guide RNA. The linear DNA product (e.g. the closed linear DNA product) may comprise (or further comprise) a gene sequence encoding a nuclease protein of a CRISPR system (e.g. Cas9, Cpf1, or MAD7) and a guide RNA. The linear DNA product (e.g. the closed linear DNA product) may comprise (or further comprise) a gene sequence encoding a genomic target to be modified (e.g. a spacer). The linear DNA product (e.g. the closed linear DNA product) may be ligated to a vector. The vector may comprise a sequence of some of the components of the CRIPSR system. The vector may comprise a sequence of guide RNA or a sequence of a part of the guide RNA. If the vector comprises a sequence of a part of the guide RNA, the linear DNA product (e.g. the closed linear DNA product) may comprise the missing sequence part of the guide RNA, so that upon ligation, the ligated vector comprises a full sequence of a guide RNA. The nuclease of the CRISPR system and guide RNA may be encoded on a single vector or on two different vectors. The linear DNA product (e.g. the closed linear DNA product) may encode the nuclease of the CRISPR system and guide RNA. One linear DNA product (e.g. one closed linear DNA product) may encode the nuclease of the CRISPR system, and the other linear DNA product (e.g. the other closed linear DNA product) may encode guide RNA.

The linear DNA product (e.g. the closed linear DNA product) may be for use in CRISPR-Cas mediated repair by recombination, homology-directed repair, or non-homologous end joining.

If the nuclease of the CRISPR system and the guide RNA are encoded by a different linear DNA product (e.g. a different closed linear DNA product), they may be part of a different or the same delivery mechanism. For example, the linear DNA product (e.g. the closed linear DNA product) encoding the nuclease of the CRISPR system may be delivered to a cell by a first nanoparticle, non-viral vector or viral vector, whereas the linear DNA product (e.g. the closed linear DNA product) encoding the guide RNA may be delivered to a cell by a second nanoparticle, a non-viral vector, or viral vector. For example, the linear DNA product (e.g. the closed linear DNA product) encoding the nuclease of the CRISPR system and the linear DNA product (e.g. the closed linear DNA product) encoding the guide RNA may be delivered to a cell by the same nanoparticle, non-viral vector or viral vector.

If the nuclease of the CRISPR system and the guide RNA are encoded by the same linear DNA product (e.g. the closed linear DNA product) (or by a vector that comprises the linear DNA product (e.g. the closed linear DNA product)) they may be part of the same delivery mechanism. For example, the linear DNA product (e.g. the closed linear DNA product), or the vector, encoding the nuclease of the CRISPR system and the guide RNA may be delivered to a cell by a nanoparticle, a non-viral vector or a viral vector.

The linear DNA product (e.g. the closed linear DNA product) encoding the nuclease of the CRISPR system and the linear DNA product (e.g. the closed linear DNA product) encoding the guide RNA may be delivered to a cell by electroporation. The linear DNA product (e.g. the closed linear DNA product) encoding the nuclease of the CRISPR system and the linear DNA product (e.g. the closed linear DNA product) encoding the guide RNA may be delivered to a cell by hydrodynamic needle.

Thus, the invention provides the linear DNA product (e.g. the closed linear DNA product) described herein for use in CRISPR system delivery to a cell. The invention provides a method of delivering the CRISPR system to a cell, comprising contacting the linear DNA product (e.g. the closed linear DNA product) described herein with a cell. The invention also provides the linear DNA product (e.g. the closed linear DNA product) obtainable by the methods described herein for use in CRISPR system delivery to a cell. The invention provides a method of delivering the CRISPR system to a cell, comprising contacting the linear DNA product (e.g. the closed linear DNA product) obtainable by the methods described herein with a cell.

The cell may be an animal cell, preferably mammal cell, such as human cell.

The invention also provides a cell obtainable by the methods described herein. The cell is particularly suitable for use in cell therapy and/or in vivo therapy.

The linear DNA product produced by the methods described herein may be used in transcription, to generate RNA, preferably mRNA, in vitro or in vivo.

9. Kits

The invention provides a kit comprising components required to carry out the method described herein. The kit comprises at least:

(a) first and second adaptor molecules;
(b) an endonuclease; and
(c) a ligase.

The kit may additionally comprise a DNA polymerase, at least one buffer and/or a nuclease.

The first adaptor molecule and/or the second adaptor molecule may comprise a sequence of SEQ ID NO: 1 or a portion thereof. The first adaptor molecule and/or the second adaptor molecule may comprise at least 13, at least 14, at least 15, at least 16, at least 17, at least 18, or at least 19 contiguous nucleotides of SEQ ID NO: 1. The first and second adapter molecules may comprise an identical nucleic acid sequence. The first and second adapter molecules may comprise a different nucleic acid sequence. The first adaptor molecule may comprise one or more protected nucleotides and the second adaptor molecule may comprise a hairpin or a stem loop region.

The first and second adaptor molecule may be provided in a kit together or separately.

The first adaptor molecule and/or the second adaptor molecule may comprise one or more locked nucleic acids (LNAs).

The first adaptor molecule and/or the second adaptor molecule may comprise one or more protected nucleotides (i.e. nuclease-resistant nucleotides), such as phosphorothioated nucleotides.

The endonuclease may be a restriction enzyme endonuclease. The endonuclease may be a Type IIS restriction enzyme. The endonuclease may be any enzyme that recognizes a DNA sequence and cleaves outside of the recognition sequence. For example, the endonuclease may be a BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BslFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, BtsI-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction enzyme.

The ligase may be a DNA ligase, such as a T4 DNA ligase, T7 DNA ligase, mammalian DNA ligase I, III and IV; Taq DNA ligase, Tth DNA ligase, or *E. coli* DNA ligase.

The nuclease may be an exonuclease e.g. exonuclease I, exonuclease III and/or exonuclease VIII.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

BRIEF DESCRIPTION OF THE DRAWINGS

FIG. 8 summarizes ligation yields obtained from two independent assays for each DNA molecule (i.e. Construct A, Construct B and Construct C, see FIG. 5).

TABLE 1

Figure 1:
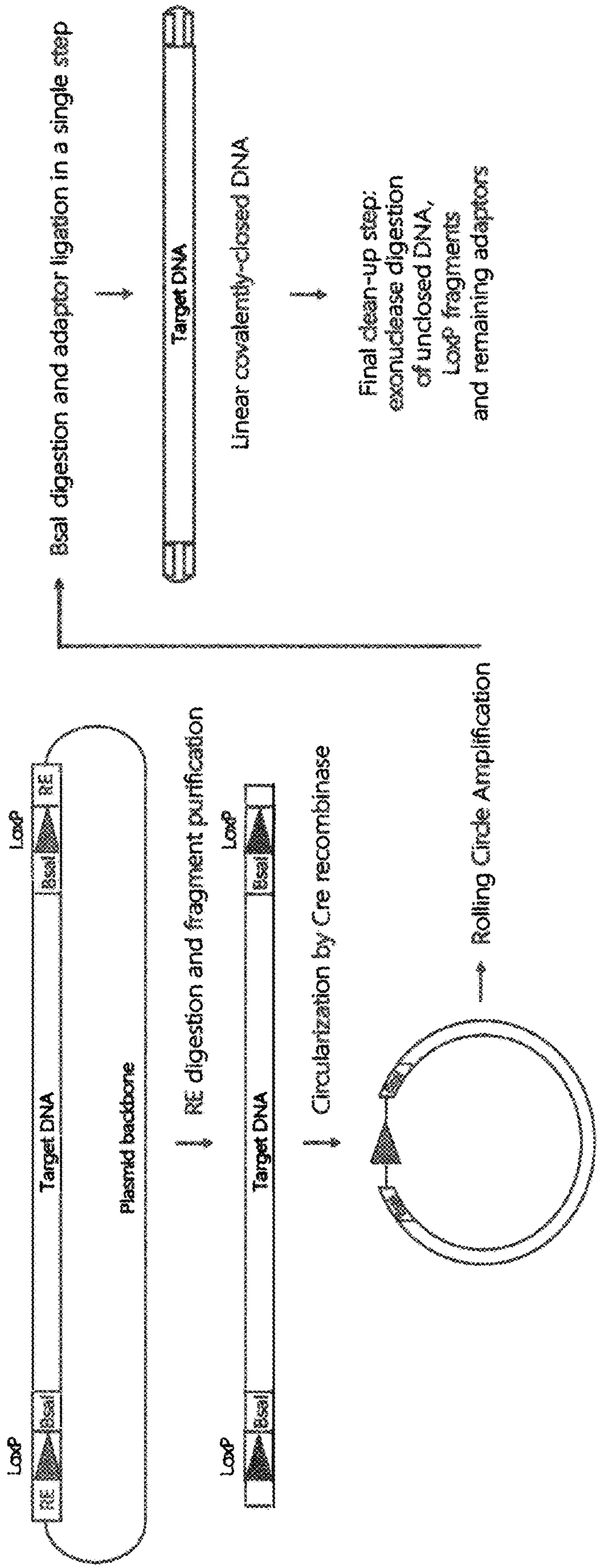
FIG. 1 illustrates the workflow to obtain closed linear DNA product by digestion and ligation of adaptor molecules in a single step, starting from amplified DNA obtained through rolling circle amplification (RCA) of a circular DNA template generated through the action of Cre recombinase on substrates containing two LoxP sequences (SEQ ID NO: 3) flanking the DNA of interest in the same direction.

Sequences discussed in the application.

| SEQ ID NO | Sequence |
|---|---|
| SEQ ID NO: 1 | AGGGCTAACATTTGTTGGCC |
| SEQ ID NO: 2 | GGCCAACAAATGTTAG |
| SEQ ID NO: 3 | ATAACTTCGTATAATGTATG CTATACGAAG TTAT |
| SEQ ID NO: 4 | AGGGCTAACATTTGTTGGCC ACTCAGGCCA ACAAATGTTAG |
| SEQ ID NO: 5 | GGCCAACAAATGTTAG |
| SEQ ID NO: 6 | AGGGCTAACATTTGTTGGCC |
| SEQ ID NO: 7 | TGATGCGGTTTTGGCAGTACATCAATGGGCGTGGATAGCGGTTTGACTC<br>ACGGGGATTTCCAAGTCTCCACCCCATTGACGTCAATGGGAGTTTGTTTT<br>GGCACCAAAATCAACGGGACTTTCCAAAATGTCGTAACAACTCCGCCCCA<br>TTGACGCAAATGGGGGGTAGGCGTGTACGGTGGGAGGTCTATATAAGCA<br>GAGCT |
| SEQ ID NO: 8 | CGTTACATAACTTACGGTAAATGGCCCGCCTGGCTGACCGCCCAACGAC<br>CCCCGCCCATTGACGTCAATAATGACGTATGTTCCCATAGTAACGCCAAT<br>AGGGACTTTCCATTGACGTCAATGGGTGGAGTATTTACGGTAAACTGCCC<br>ACTTGGCAGTACATCAAGTGTATCATATGCCAAGTACGCCCCCTATTGAC |

TABLE 1-continued

| Sequences discussed in the application. | |
|---|---|
| SEQ ID NO | Sequence |
| | GTCAATGACGGTAAATGGCCCGCCTGGCATTATGCCCAGTACATGACCTT ATGGGACTTTCCTACTTGGCAGTACATCTACGTATTAGTCATCGCTATTAC CATG |
| SEQ ID NO: 9 | ATGGTCAGCAAGGGCGAGGAACTGTTCACCGGGGTGGTGCCCATCCTG GTCGAGCTGGACGGCGACGTAAACGGCCACAAGTTCAGCGTGTCCGGC GAGGGCGAGGGCGATGCCACCTACGGCAAGCTGACCCTGAAGTTCATCT GTACCACCGGCAAGCTGCCCGTGCCCTGGCCCACCCTCGTGACCACCC TGACCTACGGCGTGCAATGCTTCAGCCGCTACCCCGACCACATGAAGCA GCACGACTTCTTCAAGTCCGCCATGCCCGAAGGCTACGTCCAGGAGCGC ACCATCTTCTTCAAGGACGACGGCAACTACAAGACCCGCGCCGAGGTGA AGTTCGAGGGCGACACCCTGGTGAACCGCATCGAGCTGAAGGGCATCG ACTTCAAGGAGGACGGCAACATCCTGGGGCACAAGCTGGAGTACAACTA CAACAGCCACAACGTCTATATCATGGCCGACAAGCAGAAGAACGGCATC AAGGTGAACTTCAAGATCCGCCACAACATCGAGGACGGCAGCGTGCAAC TCGCCGACCACTACCAGCAGAACACCCCCATCGGCGACGGCCCCGTGC TGCTGCCCGACAACCACTACCTGAGCACCCAGTCCGCCCTGAGCAAAGA CCCCAACGAGAAGCGCGATCACATGGTCCTGCTGGAGTTCGTGACCGCC GCCGGGATCACTCTCGGCATGGACGAGCTGTACAAGTAG |
| SEQ ID NO: 10 | TAAGATACATTGATGAGTTTGGACAAACCACAACTAGAATGCAGTGAAAA AAATGCTTTATTTGTGAAATTTGTGATGCTATTGCTTTATTTGTAAC- CATTA TAAGCTGCAATAAACAAGTT |
| SEQ ID NO: 11 | TGCAGGCAGCTGCGCGCTCGCTCGCTCACTGAGGCCGCCCGGGCAAAG CCCGGGCGTCGGGCGACCTTTGGTCGCCCGGCCTCAGTGAGCGAGCGA GCGCGCAGAGAGGGAGTGGCCAACTCCATCACTAGGGGTTCCT |
| SEQ ID NO: 12 | ATGGAAGACGCCAAAAACATAAAGAAAGGCCCGGCGCCATTCTATCCGC TGGAAGATGGAACCGCTGGAGAGCAACTGCATAAGGCTATGAAGAGATA CGCCCTGGTTCCTGGAACAATTGCTTTTACAGATGCACATATCGAGGTGG ACATCACTTACGCTGAGTACTTCGAAATGTCCGTTCGGTTGGCAGAAGCT ATGAAACGATATGGGCTGAATACAAATCACAGAATCGTCGTATGCAGTGA AAACTCTCTTCAATTCTTTATGCCGGTGTTGGGCGCGTTATTTATCGGAGT TGCAGTTGCGCCCGCGAACGACATTTATAATGAACGTGAATTGCTCAACA GTATGGGCATTTCGCAGCCTACCGTGGTGTTCGTTTCCAAAAAGGGGTT GCAAAAAATTTTGAACGTGCAAAAAAAGCTCCCAATCATCCAAAAAATTAT TATCATGGATTCTAAAACGGATTACCAGGGATTTCAGTCGATGTACACGT TCGTCACATCTCATCTACCTCCCGGTTTTAATGAATACGATTTTGTGCCAG AGTCCTTCGATAGGGACAAGACAATTGCACTGATCATGAACTCCTCTGGA TCTACTGGTCTGCCTAAAGGTGTCGCTCTGCCTCATAGAACTGCCTGCGT GAGATTCTCGCATGCCAGAGATCCTATTTTTGGCAATCAAATCATTCCGG ATACTGCGATTTTAAGTGTTGTTCCATTCCATCACGGTTTTGGAATGTTTA CTACACTCGGATATTTGATATGTGGATTTCGAGTCGTCTTAATGTATAGAT TTGAAGAAGAGCTGTTTCTGAGGAGCCTTCAGGATTACAAGATTCAAAGT GCGCTGCTGGTGCCAACCCTATTCTCCTTCTTCGCCAAAAGCACTCTGAT TGACAAATACGATTTATCTAATTTACACGAAATTGCTTCTGGTGGCGCTCC CCTCTCTAAGGAAGTCGGGGAAGCGGTTGCCAAGAGGTTCCATCTGCCA GGTATCAGGCAAGGATATGGGCTCACTGAGACTACATCAGCTATTCTGAT TACACCCGAGGGGGATGATAAACCGGGCGCGGTCGGTAAAGTTGTTCCA TTTTTTGAAGCGAAGGTTGTGGATCTGGATACCGGGAAAACGCTGGGCG TTAATCAAAGAGGCGAACTGTGTGTGAGAGGTCCTATGATTATGTCCGGT TATGTAAACAATCCGGAAGCGACCAACGCCTTGATTGACAAGGATGGATG GCTACATTCTGGAGACATAGCTTACTGGGACGAAGACGAACACTTCTTCA TCGTTGACCGCCTGAAGTCTCTGATTAAGTACAAAGGCTATCAGGTGGCT CCCGCTGAATTGGAATCCATCTTGCTCCAACACCCCAACATCTTCGACGC AGGTGTCGCAGGTCTTCCCGACGATGACGCCGGTGAACTTCCCGCCGC CGTTGTTGTTTTGGAGCACGGAAAGACGATGACGGAAAAAGAGATCGTG GATTACGTCGCCAGTCAAGTAACAACCGCGAAAAAGTTGCGCGGAGGAG TTGTGTTTGTGGACGAAGTACCGAAAGGTCTTACCGGAAAACTCGACGCA AGAAAAATCAGAGAGATCCTCATAAAGGCCAAGAAGGGCGGAAAGATCG CCGTGTAA |
| SEQ ID NO: 13 | AAAAAAAAAAAAAAAAA |
| SEQ ID NO: 14 | TTTTTTTTTTTTT |
| SEQ ID NO: 15 | NAGGGCTAACATTTGTTGGCCACTCAGGCCAACAAATGTTAGCCCTN |
| SEQ ID NO: 16 | AAAAAAAAAAAAAAAAAA |
| SEQ ID NO: 17 | TTTTTTTTTTTTTTTTTT |
| SEQ ID NO: 18 | GGTCTCGCCCTN |

TABLE 1-continued

Sequences discussed in the application.

| SEQ ID NO | Sequence |
|---|---|
| SEQ ID NO: 19 | NAGGGCGAGACC |
| SEQ ID NO: 20 | AAAAACGAGACC |
| SEQ ID NO: 21 | GGTCTCGTTTTT |
| SEQ ID NO: 22 | GGCCAACAAATGTTAGCCCTN |
| SEQ ID NO: 23 | NAGGGCTAACATTTGTTGGCC |
| SEQ ID NO: 24 | ATGGAAGATGCCAAAAACATTAAGAAGGGCCCAGCGCCATTCTACCCACT<br>CGAAGACGGGACCGCCGGCGAGCAGCTGCACAAAGCCATGAAGCGCTA<br>CGCCCTGGTGCCCGGCACCATCGCCTTTACCGACGCACATATCGAGGTG<br>GACATTACCTACGCCGAATACTTCGAGATGAGCGTTCGGCTGGCAGAAG<br>CTATGAAGCGCTATGGGCTGAATACAAACCATCGGATCGTGGTGTGCAG<br>CGAGAATAGCTTGCAGTTCTTCATGCCCGTGTTGGGTGCCCTGTTCATCG<br>GTGTGGCTGTGGCCCCAGCTAACGACATCTACAACGAGCGCGAGCTGCT<br>GAACAGCATGGGCATCAGCCAGCCCACCGTCGTATTCGTGAGCAAGAAA<br>GGGCTGCAAAAGATCCTCAACGTGCAAAAGAAGCTACCGATCATACAAAA<br>GATCATCATCATGGATAGCAAGACCGACTACCAGGGCTTCCAAAGCATGT<br>ACACCTTCGTGACTTCCCATTTGCCACCCGGCTTCAACGAGTACGACTTC<br>GTGCCCGAGAGCTTCGACCGGGACAAAACCATCGCCCTGATCATGAACA<br>GTAGTGGCAGTACCGGATTGCCCAAGGGCGTAGCCCTACCGCACCGCA<br>CCGCTTGTGTCCGATTCAGTCATGCCCGCGACCCCATCTTCGGCAACCA<br>GATCATCCCCGACACCGCTATCCTCAGCGTGGTGCCATTTCACCACGGC<br>TTCGGCATGTTCACCACGCTGGGCTACTTGATCTGCGGCTTTCGGGTCG<br>TGCTCATGTACCGCTTCGAGGAGGAGCTATTCTTGCGCAGCTTGCAAGA<br>CTATAAGATTCAATCTGCCCTGCTGGTGCCCACACTATTTAGCTTCTTCG<br>CTAAGAGCACTCTCATCGACAAGTACGACCTAAGCAACTTGCACGAGATC<br>GCCAGCGGCGGGGCGCCGCTCAGCAAGGAGGTAGGTGAGGCCGTGGC<br>CAAACGCTTCCACCTACCAGGCATCCGACAGGGCTACGGCCTGACAGAA<br>ACAACCAGCGCCATTCTGATCACCCCCGAAGGGGACGACAAGCCTGGC<br>GCAGTAGGCAAGGTGGTGCCCTTCTTCGAGGCTAAGGTGGTGGACTTGG<br>ACACCGGTAAGACACTGGGTGTGAACCAGCGCGGCGAGCTGTGCGTCC<br>GTGGCCCCATGATCATGAGCGGCTACGTTAACAACCCCGAGGCTACAAA<br>CGCTCTCATCGACAAGGACGGCTGGCTGCACAGCGGCGACATCGCCTA<br>CTGGGACGAGGACGAGCACTTCTTCATCGTGGACCGGCTGAAGTCCCTG<br>ATCAAATACAAGGGCTACCAGGTAGCCCCAGCCGAACTGGAGAGCATCC<br>TGCTGCAACACCCCAACATCTTCGACGCCGGGGTCGCCGGCCTGCCCG<br>ACGACGATGCCGGCGAGCTGCCCGCCGCAGTCGTCGTGCTGGAACACG<br>GTAAAACCATGACCGAGAAGGAGATCGTGGACTATGTGGCCAGCCAGGT<br>TACAACCGCCAAGAAGCTGCGCGGTGGTGTTGTGTTCGTGGACGAGGTG<br>CCTAAAGGACTGACCGGCAAGTTGGACGCCCGCAAGATCCGCGAGATTC<br>TCATTAAGGCCAAGAAGGGCGGCAAGATCGCCGTGTAA |
| SEQ ID NO: 25 | ATGGTGAGCAAGGGCGAGGAGCTGTTCACCGGGGTGGTGCCCATCCTG<br>GTCGAGCTGGACGGCGACGTAAACGGCCACAAGTTCAGCGTGTCCGGC<br>GAGGGCGAGGGCGATGCCACCTACGGCAAGCTGACCCTGAAGTTCATCT<br>GCACCACCGGCAAGCTGCCCGTGCCCTGGCCCACCCTCGTGACCACCC<br>TGACCTACGGCGTGCAGTGCTTCAGCCGCTACCCCGACCACATGAAGCA<br>GCACGACTTCTTCAAGTCCGCCATGCCCGAAGGCTACGTCCAGGAGCGC<br>ACCATCTTCTTCAAGGACGACGGCAACTACAAGACCCGCGCCGAGGTGA<br>AGTTCGAGGGCGACACCCTGGTGAACCGCATCGAGCTGAAGGGCATCG<br>ACTTCAAGGAGGACGGCAACATCCTGGGGCACAAGCTGGAGTACAACTA<br>CAACAGCCACAACGTCTATATCATGGCCGACAAGCAGAAGAACGGCATC<br>AAGGTGAACTTCAAGATCCGCCACAACATCGAGGACGGCAGCGTGCAGC<br>TCGCCGACCACTACCAGCAGAACACCCCCATCGGCGACGGCCCCGTGC<br>TGCTGCCCGACAACCACTACCTGAGCACCCAGTCCGCCCTGAGCAAAGA<br>CCCCAACGAGAAGCGCGATCACATGGTCCTGCTGGAGTTCGTGACCGCC<br>GCCGGGATCACTCTCGGCATGGACGAGCTGTACAAGTAA |

CLAUSES

1. A method for producing a linear deoxyribonucleic acid (DNA) product, wherein the method comprises:

(a) contacting a double-stranded DNA molecule with an endonuclease and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region.

2. The method of clause 1, wherein the appending is performed by ligation and/or hybridization.

3. A method for producing a closed linear deoxyribonucleic acid (DNA) product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

4. A method for producing a closed linear deoxyribonucleic acid (DNA) product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the closed linear DNA product, wherein the closed linear DNA product comprises a linear portion of the double-stranded DNA molecule, and wherein the linear portion of the double-stranded DNA molecule is closed at a first end by the first adaptor molecule and closed at a second end by the second adaptor molecule.

5. The method of clause 3 or clause 4, wherein the linear portion of the double-stranded DNA molecule is closed at the first end and the second end by ligation of the first and second adaptor molecules.

6. The method of any one of clauses 3-5, wherein the first closed end and the second closed end are resistant to nuclease digestion.

7. The method of clause 6, wherein the nuclease digestion is exonuclease digestion, optionally exonuclease III digestion and/or exonuclease I digestion.

8. The method of any one of clauses 3-7, wherein the closed linear DNA product is a covalently closed linear DNA product.

9. The method of any one of clauses 3-8, wherein the closed linear DNA product is partially double-stranded and/or partially single-stranded.

10. The method of any one of clauses 3-9, wherein the closed linear DNA product comprises at least 500, at least 1000, at least 2000, at least 3000, at least 4000, at least 5000, at least 6000, at least 7000, at least 8000, at least 9000, at least 10,000, at least 11,000, at least 12,000, at least 13,000, at least 14,000, or at least 15,000 nucleotides in length.

11. The method of any one of clauses 1-10, wherein the double-stranded DNA molecule is circular or branched.

12. The method of any one of clauses 1-11, wherein the double-stranded DNA molecule comprises a cassette, optionally wherein the cassette comprises a coding sequence.

13. The method of any one of clauses 1-12, wherein the double-stranded DNA molecule comprises a spacer, optionally wherein the spacer is at least 10, at least 20, at least 30, at least 40, at least 50, at least 60, at least 70, at least 80, at least 90, at least 100, at least 125, at least 150, at least 175, or at least 200 base pairs long.

14. The method of any one of clauses 3-13, wherein the closed DNA product comprises a homopolymeric sequence, such as a polyA, poly C, polyT or polyG sequence.

15. The method of any one of clauses 3-14, wherein the closed DNA product comprises an inverted terminal repeat sequence.

16. The method of any one of clauses 1-15, wherein the double-stranded DNA molecule comprises one or more endonuclease target sequences, optionally wherein the one or more endonuclease target sequences are Type IIS endonuclease target sequences, such as BbsI, BsaI, BsmBI, BspQI, BtgZI, Esp3I, and/or SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI target sequences.

17. The method of any one of clauses 1-16, wherein the double-stranded DNA molecule is a product of amplification, optionally rolling circle amplification.

18. The method of any one of clauses 1-17, wherein the endonuclease is a restriction enzyme endonuclease, optionally wherein the endonuclease is Type IIS restriction enzyme endonuclease, such as BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, Btsl-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqiI, TspDTI and/or TspGWI restriction enzyme endonuclease.

19. The method of any one of clauses 1-18, wherein the ligase is a DNA ligase, optionally wherein the DNA ligase is a T4 DNA ligase, T7 DNA ligase, mammalian DNA ligase I, III and IV; Taq DNA ligase, Tth DNA ligase, or *E. coli* DNA ligase.

20. The method of any one of clauses 1-19, wherein the first adaptor molecule and/or the second adaptor molecule is a synthetic adaptor molecule.

21. The method of any one of clauses 1-20, wherein the first adaptor molecule comprises a hairpin and/or the second adaptor molecule comprises a hairpin.

22. The method of any one of clauses 1-21, wherein the first adaptor molecule is a nucleic acid adaptor molecule.

23. The method of any one of clauses 1-22, wherein the second adaptor molecule is a nucleic acid adaptor molecule.

24. The method of any one of clauses 1-23, wherein the first adaptor molecule and/or the second adaptor molecule comprise a single-stranded portion, optionally wherein:

(a) the single-stranded portion forms a hairpin;

(b) the single-stranded portion comprises less than 10, 9, 8, 7, 6, 5, 4, 3, 2 nucleotides; and/or (c) the single-stranded portion comprises 5 nucleotides.

25. The method of any one of clauses 1-24, wherein the first adaptor molecule and/or the second adaptor molecule comprise a double-stranded portion, optionally wherein:

(a) the double-stranded portion comprises less than 50, 45, 40, 35, 30 base pairs; and/or (b) the double-stranded portion comprises at least 10, 11, 12, 13, 14, 15 base pairs.

26. The method of any one of clauses 1-25, wherein the first adaptor molecule and/or the second adaptor molecule comprise a 5' phosphate.

27. The method of any one of clauses 1-26, wherein the first adaptor molecule and/or the second adaptor molecule comprise a sequence of SEQ ID NO: 1.

28. The method of any one of clauses 1-26, wherein the first adaptor molecule and/or the second adaptor molecule comprise at least 13, at least 14, at least 15, at least 16, at least 17, at least 18, or at least 19 contiguous nucleotides of SEQ ID NO: 1.

29. The method of clause 25, wherein the double-stranded portion of the first adaptor molecule and/or the second adaptor molecule comprises a sequence of SEQ ID NO: 2.

30. The method of clause 25, wherein the double-stranded portion of the first adaptor molecule and/or the second adaptor molecule comprise at least 8, at least 9, at least 10, at least 11, at least 12, at least 13, at least 14 or at least 15 contiguous nucleotides of SEQ ID NO: 2.

31. The method of clause 24, wherein the single-stranded portion of the first adaptor molecule and/or the second adaptor molecule comprise a sequence of ACTCA.

32. The method of clause 24, wherein the single-stranded portion of the first adaptor molecule and/or the second adaptor molecule may comprise at least 1, at least 2, at least 3, at least 4 or at least 5 contiguous nucleotides of ACTCA.

33. The method of any one of clauses 1-32, wherein the first and second adapter molecules are different.

34. The method of any one of clauses 1-33, wherein the first adaptor molecule comprises a portion that is complementary to the first end of the linear double-stranded region.

35. The method of any one of clauses 1-34, wherein the second adaptor molecule comprises a portion that is complementary to the second end of the linear double-stranded region.

36. The method of any one of clauses 1-35, wherein the first adaptor molecule comprises a portion that anneals to the first end of the linear double-stranded region.

37. The method of any one of clauses 1-37, wherein the second adaptor molecule comprises a portion that anneals to the second end of the linear double-stranded region.

38. The method of any one of clauses 1-37, wherein the first adaptor molecule and/or the second adaptor molecule comprise an overhang.

39. The method of any one of clauses 1-38, wherein the first adaptor molecule and/or the second adaptor molecule comprise a functional portion, optionally wherein the functional portion is a binding molecule, a targeting sequence, or a probe.

40. The method of any one of clauses 1-39, wherein the first adaptor molecule and/or the second adaptor molecule comprise a nuclear localization sequence.

41. The method of any one of clauses 1-40, wherein the first adaptor molecule and/or the second adaptor molecule comprise a barcode.

42. The method of any one of clauses 1-41, wherein the first adaptor molecule and/or the second adaptor molecule comprise a fluorophore.

43. The method of any one of clauses 1-42, wherein the first adaptor molecule and/or the second adaptor molecule comprise a radioactive compound.

44. The method of any one of clauses 1-43, wherein the first adaptor molecule and/or the second adaptor molecule comprise a portion that facilitates sequencing, detection or quantification.

45. The method of any one of clauses 1-44, wherein the first adaptor molecule and/or the second adaptor molecule comprise an inverted terminal repeat sequence.

46. The method of any one of clauses 1-45, wherein the first adaptor molecule and/or the second adaptor molecule comprise an aptamer.

47. The method of any one of clauses 1-46, wherein the first adaptor molecule and/or the second adaptor molecule confer resistance to the nuclease digestion, optionally exonuclease digestion (e.g. exonuclease I and/or exonuclease III digestion).

48. The method of any one of clauses 1-47, wherein the first and second adaptor molecules are ligated to the linear double-stranded region.

49. The method of clause 48, wherein ligation is at least 5%, at least 10%, at least 15, at least 20%, at least 25%, at least 30%, at least 35%, at least 40, at least 45%, at least 50%, at least 55%, at least 60, at least 65, at least 70%, at least 75, at least 80%, at least 82%, at least 85%, at least 90%, or at least 95% efficient.

50. The method of any one of clauses 1-49, wherein the step of incubating the single contiguous aqueous volume comprises incubating at a first temperature and then incubating at a second temperature; optionally wherein:

(a) the first temperature is 1° C.-100° C., 4° C.-70° C., 10° C.-60° C., 16° C.-55° C., 20° C.-50° C., 25° C.-45° C., 30° C.-40° C., or 35° C.-39° C.; and/or (b) the second temperature is 1° C.-100° C., 4° C.-70° C., 8° C.-60° C., 10° C.-55° C., 23° C.-50° C., 14° C.-40° C., 14° C.-30° C., or 15° C.-18° C.

51. The method of clause 50, wherein the first temperature is 35° C.-39° C. and the second temperature is 15° C.-18° C.

52. The method of clause 50 or 51, wherein the first temperature is 37° C. and the second temperature is 16° C.

53. The method of any one of clauses 1-52, wherein the step of incubating the single contiguous aqueous volume comprises cycling between the first temperature and the second temperature, optionally wherein the step of incubating the single contiguous aqueous volume comprises cycling between the first temperature and the second temperature at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 80, at least 90, or at least 100 times, preferably at least 20 times.

54. The method of any one of clauses 1-52, wherein the step of incubating the single contiguous aqueous volume comprises incubating at a constant temperature.

55. The method of clause 54, wherein the constant temperature is about 30° C. or about 37° C.

56. The method of any one of clauses 1-55, wherein the method further comprises, before step (a) (i.e. the step of contacting the double-stranded DNA molecule with the endonuclease, the ligase and the first and second adaptor molecules), a step of amplification of a DNA template molecule to produce the double-stranded DNA molecule, optionally wherein amplification is rolling circle amplification.

57. The method of any one of clauses 1-56, wherein the method further comprises, after step (b) (i.e. the step of incubating the single contiguous aqueous volume), a step of purification of the linear DNA product or closed linear DNA product.

58. The method of any one of clauses 1-57, wherein the method further comprises, after step (b) (i.e. the step of incubating the single contiguous aqueous volume), a step of nuclease digestion, optionally wherein the nuclease digestion is exonuclease digestion, such as exonuclease I and/or exonuclease III digestion.

59. The method of clause 58, wherein the step of nuclease digestion takes places before or after the step of purification 60. A method for producing a linear deoxyribonucleic acid (DNA) product, wherein the method comprises:

(a) contacting a double-stranded DNA molecule with an endonuclease and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first and second adaptor molecules are nucleic acid molecules that comprise one or more nuclease-resistant nucleotides.

61. The method of clause 60, wherein step (a) comprises contacting the double-stranded DNA molecule with an endonuclease, a ligase and first and second adaptor molecules to form a single contiguous aqueous volume.

62. The method of clauses 60 or 61, wherein the first adaptor molecule is ligated to a first end of the linear double-stranded region and the second adaptor molecule is ligated to a second end of the linear double-stranded region.

63. The method of any one of clauses 60-62, wherein the linear DNA product is resistant to nuclease digestion, optionally wherein the nuclease digestion is exonuclease digestion, such as exonuclease III digestion and/or exonuclease I digestion.

64. The method of any one of clauses 60-63, wherein the nuclease-resistant nucleotides are phosphorothioated nucleotides.

65. A method for producing a closed linear deoxyribonucleic acid (DNA) product, the method comprises:

(a) rolling circle amplification of a DNA template molecule comprising at least one endonuclease target sequence to generate a double-stranded DNA molecule;

(b) contacting the double-stranded DNA molecule with an endonuclease, a ligase and first and second adaptor molecules to form a single contiguous aqueous volume; and (c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

66. A method for producing a partially closed deoxyribonucleic acid (DNA) product, wherein the method comprises:

(a) contacting a double-stranded DNA molecule with an endonuclease and first and second adaptor molecules to form a single contiguous aqueous volume; and (b) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is appended to a first end of the linear double-stranded region and the second adaptor molecule is appended to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule.

67. The method of clause 66, wherein step (a) comprises contacting the double-stranded DNA molecule with an endonuclease, a ligase and first and second adaptor molecules to form a single contiguous aqueous volume.

68. The method of clauses 66 or 67, wherein the first adaptor molecule is ligated to a first end of the linear double-stranded region and the second adaptor molecule is ligated to a second end of the linear double-stranded region.

69. The method of any one of clauses 66-68, wherein the linear DNA product is resistant to nuclease digestion, optionally wherein the nuclease digestion is exonuclease digestion, such as exonuclease III digestion and/or exonuclease I digestion.

70. The method of any one of clauses 66-69, wherein the nuclease-resistant nucleotides are phosphorothioated nucleotides.

71. A method for producing a partially closed deoxyribonucleic acid (DNA) product, the method comprises:

(a) rolling circle amplification of a DNA template molecule comprising at least one endonuclease target sequence to generate a double-stranded DNA molecule;

(b) contacting the double-stranded DNA molecule with an endonuclease, a ligase and first and second adaptor molecules to form a single contiguous aqueous volume; and (c) incubating the single contiguous aqueous volume to generate the partially closed linear DNA product, wherein the partially closed linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first adaptor molecule is a nucleic acid molecule that comprise one or more nuclease-resistant nucleotides, and wherein the linear double-stranded region is closed at the second end by the second adaptor molecule.

71. A method for in vitro transcription of a closed linear deoxyribonucleic acid (DNA) product, the method comprises:

(a) contacting a double-stranded DNA molecule with an endonuclease, a ligase and first and second adaptor molecules to form a single contiguous aqueous volume;

(b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(c) contacting the closed linear DNA product with a polymerase; and (d) producing a transcription product.

72. A method for protein expression, the method comprises:

(a) contacting a double-stranded DNA molecule with an endonuclease, a ligase and first and second adaptor molecules to form a single contiguous aqueous volume;

(b) incubating the single contiguous aqueous volume to generate a closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule; and (c) introducing the closed linear DNA product into a prokaryotic cell or a eukaryotic cell or a cell-free protein expression system to generate a desired RNA or protein.

73. A method for cell transfection of a closed linear deoxyribonucleic acid (DNA) product into a cell, the method comprises:

(a) contacting a double-stranded DNA molecule with an endonuclease, a ligase and first and second adaptor molecules to form a single contiguous aqueous volume;

(b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule;

(c) contacting the closed linear DNA product with the cell; and (d) transfecting the closed linear DNA product into the cytosol of the cell.

73. A method for producing a pharmaceutical composition comprising the closed linear DNA product, the method comprising performing the method of any of one of clauses 3-59 and formulating the resulting closed linear DNA product with a pharmaceutically acceptable carrier or excipient.

74. A method for producing a pharmaceutical composition comprising the linear DNA product, the method comprising performing the method of any of one of clauses 60-64 and formulating the resulting linear DNA product with a pharmaceutically acceptable carrier or excipient.

75. A method for producing a pharmaceutical composition comprising the partially closed linear DNA product, the method comprising performing the method of any of one of clauses 66-71 and formulating the resulting linear DNA product with a pharmaceutically acceptable carrier or excipient.

76. Use of a closed linear DNA product in the manufacture of a medicament for treatment of a human or animal body by therapy, wherein the manufacture comprises performing the method of any one of clauses 3-59.

77. Use of a linear DNA product in the manufacture of a medicament for treatment of a human or animal body by therapy, wherein the manufacture comprises performing the method of any one of clauses 60-64.

78. Use of a partially closed linear DNA product in the manufacture of a medicament for treatment of a human or animal body by therapy, wherein the manufacture comprises performing the method of any one of clauses 66-71.

79. Use of a closed linear DNA product in the production of viral or non-viral delivery system, wherein the closed linear DNA product is produced by performing the method of any one of clauses 3-59.

80. Use of a linear DNA product in the production of viral or non-viral delivery system, wherein the linear DNA product is produced by performing the method of any one of clauses 60-64.

81. Use of a partially closed linear DNA product in the production of viral or non-viral delivery system, wherein the partially closed linear DNA product is produced by performing the method of any one of clauses 66-71.

82. A closed linear DNA product obtainable by the method of any one of clauses 3-59.

83. A linear DNA product obtainable by the method of any one of clauses 60-64.

84. A partially closed linear DNA product obtainable by the method of any one of clauses 66-71.

85. A closed linear DNA product obtainable by the method of any one of clauses 3-59 for use in therapy.

86. A linear DNA product obtainable by the method of any one of clauses 60-64 for use in therapy.

87. A partially closed linear DNA product obtainable by the method of any one of clauses 66-71 for use in therapy.

88. A kit comprising:

(a) first and second adaptor molecules;

(b) an endonuclease; and (c) a ligase.

89. A kit comprising:

(a) a first adaptor molecule;

(b) a second adaptor molecule;

(c) an endonuclease; and (d) a ligase.

90. A method for producing a closed linear deoxyribonucleic acid (DNA) product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

91. The method of clause 90, wherein the closed linear DNA product comprises a spacer, optionally wherein the spacer is at least 20 base pairs long.

92. The method of clause 90 or 91, wherein the endonuclease is a Type IIS restriction endonuclease, optionally wherein the endonuclease is BbsI, BsaI, BsmBI, BspQI, BtgZI, Esp3I, SapI, AarI, Acc36I, AclWI, AcuI, AjuI, AloI, Alw26I, AlwI, ArsI, AsuHPI, BaeI, BarI, BbvI, BccI, BceAI, BcgI, BciVI, BcoDI, BfuAI, BfuI, BmrI, BmsI, BmuI, BpiI, BpmI, BpuEI, BsaXI, Bse1I, Bse3DI, BseGI, BseMI, BseMII, BseNI, BseRI, BseXI, BsgI, BsIFI, BsmAI, BsmFI, BsmI, Bso31I, BspCNI, BspMI, BspPI, BspQI, BspTNI, BsrDI, BsrI, Bst6I, BstF5I, BstMAI, BstV1I, BstV2I, BsuI, BtgZI, BtsCI, BtsI-v2, BtsMutI, BveI, CseI, CspCI, Eam1104I, EarI, EciI, Eco31I, Eco57I, Esp3I, FaqI, FauI, FokI, GsuI, HgaI, HphI, HpyAV, LguI, LmnI, Lsp1109I, LweI, MboII, MlyI, MmeI, MnlI, Mva1269I, NmeAIII, PaqCI, PciSI, PctI, PleI, PpsI, PsrI, SchI, SfaNI, TaqII, TspDTI and/or TspGWI restriction endonuclease.

93. The method of any one of clauses 90-92, wherein the first adaptor molecule and/or the second adaptor molecule are nucleic acid adaptor molecules.

94. The method of any one of clauses 90-93, wherein the first adaptor molecule comprises a hairpin and/or the second adaptor molecule comprise a hairpin.

95. The method of any one of clauses 90-94, wherein the first adaptor molecule and/or the second adaptor molecule comprises a double-stranded region with an overhang.

96. The method of any one of clauses 90-95, wherein the method comprises the steps:

(a) amplifying a DNA template molecule comprising at least one endonuclease target sequence to generate the double-stranded DNA molecule, wherein the DNA template molecule is amplified by rolling circle amplification;

(b) contacting the double-stranded DNA molecule with an endonuclease, a ligase and first and second adaptor molecules to form a single contiguous aqueous volume; and (c) incubating the single contiguous aqueous volume to generate the closed linear DNA product, wherein the closed linear DNA product comprises a linear double-stranded region, wherein the linear double-stranded region comprises a linear portion of the double-stranded DNA molecule, and wherein the linear double-stranded region is closed at a first end by the first adaptor molecule and closed at a second end by the second adaptor molecule.

97. A method for producing a linear deoxyribonucleic acid (DNA) product, wherein the method comprises:

(a) contacting a double-stranded DNA molecule with an endonuclease, a ligase and first and second adaptor molecules to form a single contiguous aqueous volume; and (b) incubating the single contiguous aqueous volume to generate the linear DNA product, wherein the linear DNA product comprises a linear double-stranded region, wherein the linear double-stranded region comprises a linear portion of the double-stranded DNA molecule, and wherein the first adaptor molecule is ligated to a first end of the linear double-stranded region and the second adaptor molecule is ligated to a second end of the linear double-stranded region, and wherein the first and second adaptor molecules are nucleic acid molecules that comprise one or more nuclease-resistant nucleotides.

98. The method of clause 97, wherein the one or more nuclease-resistant nucleotides are one or more phosphorothioated nucleotides.

99. A method for in vitro transcription of a closed linear deoxyribonucleic acid (DNA) product, or a linear DNA product, wherein the method comprises:

(a) producing a closed linear DNA product according to the method of any one of clauses 90-96, or producing a linear DNA product according to the method of clause 97 or clause 98;

(b) contacting the closed linear DNA product, or the linear DNA product, with a polymerase; and (c) producing a transcription product encoded by the closed linear DNA product, or the linear DNA product.

100. A method for producing a protein, wherein the method comprises:

(a) producing a closed linear DNA product according to the method of any one of clauses 90-96, or producing a linear DNA product according to the method of clause 97 or clause 98;

(b) introducing the closed linear DNA product, or the linear DNA product, into a cell or a cell-free expression system to generate a protein encoded by the closed linear DNA product or the linear DNA product.

101. A method for cell transfection of a closed linear deoxyribonucleic acid (DNA) product, or a linear DNA product, into a cell, wherein the method comprises:

(a) producing a closed linear DNA product according to the method of any one of clauses 90-96, or producing a linear DNA product according to the method of clause 97 or clause 98;

(b) contacting a cell with the closed linear DNA product or the linear DNA product; and (c) transfecting the closed linear DNA product, or the linear DNA product, into the cytosol of the cell.

102. The method of clause 101, wherein the transfection of the closed linear DNA product, or the linear DNA product, into the cytosol of the cell is performed by electroporation.

103. Use of a closed linear DNA product, or a linear DNA product, in the production of viral or non-viral delivery system, wherein the closed linear DNA product is produced by performing the method of any one of clauses 90-96 and the linear DNA product is produced by the method of clause 97 or clause 98.

EXAMPLES

Example 1: Rolling Circle Amplification of Cre-Derived Circular DNA

Cre recombinase from the P1 bacteriophage is a Type I topoisomerase. The enzyme catalyzes the site-specific recombination of DNA between loxP sites (SEQ ID NO: 3). LoxP recognition site (34 bp) consists of two 13 bp inverted repeats which flank an 8 bp spacer region, which confers directionality. The products of Cre-mediated recombination are dependent upon the location and relative orientation of the loxP sites. Two DNA species containing single loxP sites were fused. DNA found between two loxP sites oriented in the same direction was excised as a circular loop of DNA, while DNA between opposing loxP sites was inverted with respect to external sequences. Cre recombinase requires no additional cofactors or accessory proteins for its function.

Cre reaction conditions: reaction volume 50 μl, DNA of interest purified from agarose gel electrophoresis after restriction enzyme digestion (100 ng), Cre recombinase (NEB, 4 units), incubation time and temperature: 30 min at 37° C. and 20 min at 80° C. Next, to remove remaining non-circular DNA molecules before the amplification step, *E. coli* exonuclease I (NEB, 20 units) and III (NEB, 100 units) were added and the reaction was incubated 30 min at 37° C. and 20 min at 80° C.

Rolling circle amplification (RCA) is a faithful and isothermal DNA amplification method based on Phi29 DNA polymerase (Phi29DNApol). Phi29DNApol is the monomeric enzyme responsible for the replication of the linear double stranded DNA of bacteriophage phi29 from *Bacillus subtilis* (Blanco and Salas, 1984). It is an extremely processive polymerase (up to more than 70 kb per binding event) with a strong strand displacement capacity (Blanco et al, 1989). The enzyme displays 3'->5' proofreading exonuclease activity (Garmendia et al, 1992), resulting in an extremely high fidelity of synthesis (Esteban et al, 1993). These special features make this enzyme the perfect choice for isothermal DNA amplification.

RCA can be initiated by random synthetic primers (Dean et al, 2001) or a DNA primase like TthPrimPol (Picher et al, 2016) that synthesizes the primers for Phi29DNApol during the amplification reaction.

Figure 2:
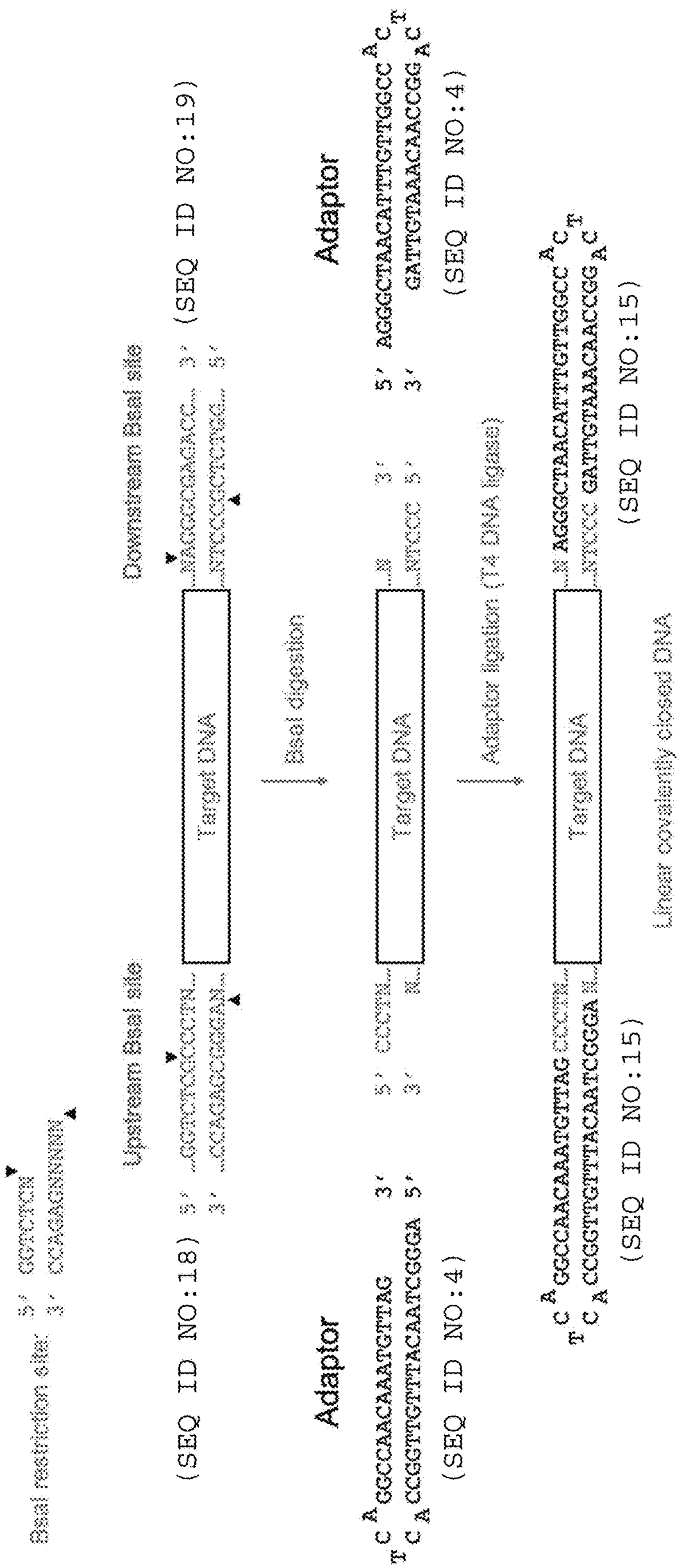
FIG. 2 illustrates the sequences driving adaptor molecules ligation after BsaI digestion of an amplified double-stranded DNA molecule in each cycle of the process. BsaI digestion produces 4-nucleotide protruding ends at 5' (TCCC 5') at both sides of the expression cassette. Self-complementary adaptor molecules (SEQ ID NO: 4 containing a 4-nucleotide protruding end at 5' (GGGA 5') is then ligated at both sides of the expression cassette, resulting in covalently closed linear DNA product.
Figure 3:
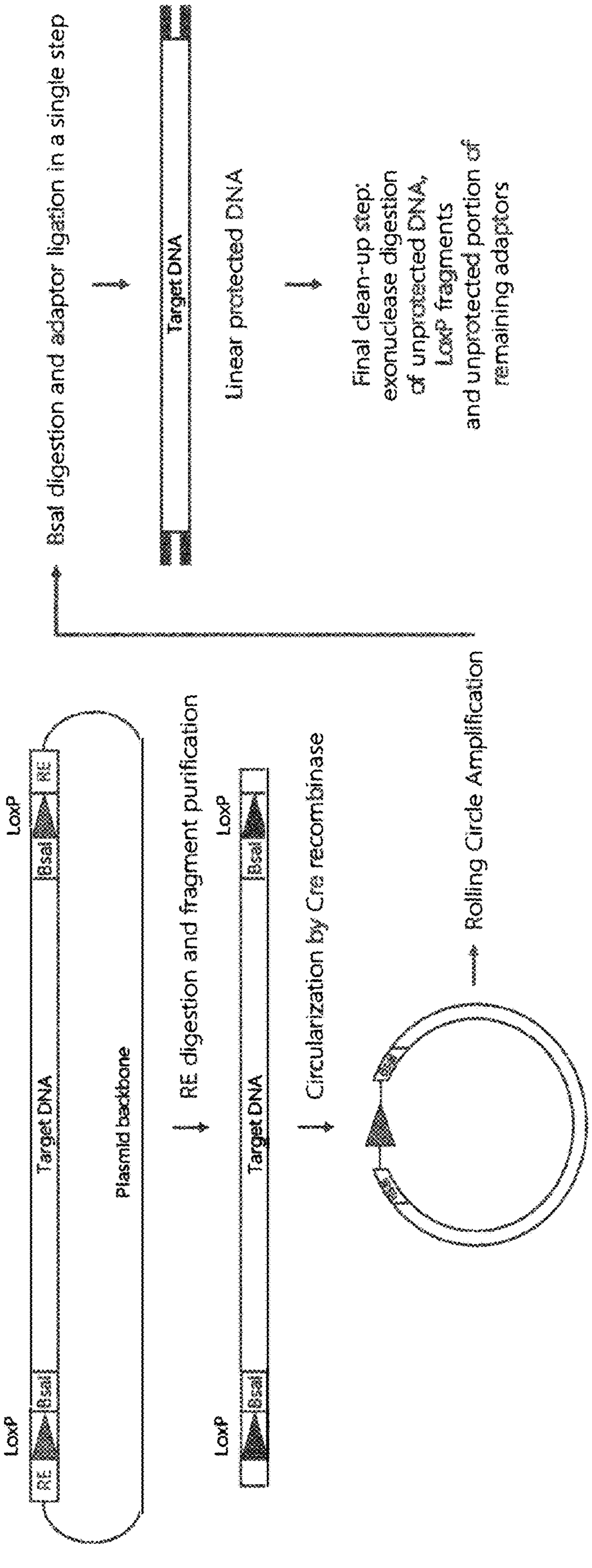
FIG. 3 illustrates the workflow to obtain a linear DNA product comprising protected nucleotides by digestion and ligation of adaptor molecules in a single step, starting from amplified double-stranded DNA molecule obtained through rolling circle amplification (RCA) of a circular DNA template generated through the action of Cre recombinase on substrates containing two LoxP sequences (SEQ ID NO: 3) flanking the DNA of interest in the same direction.
Figure 4:
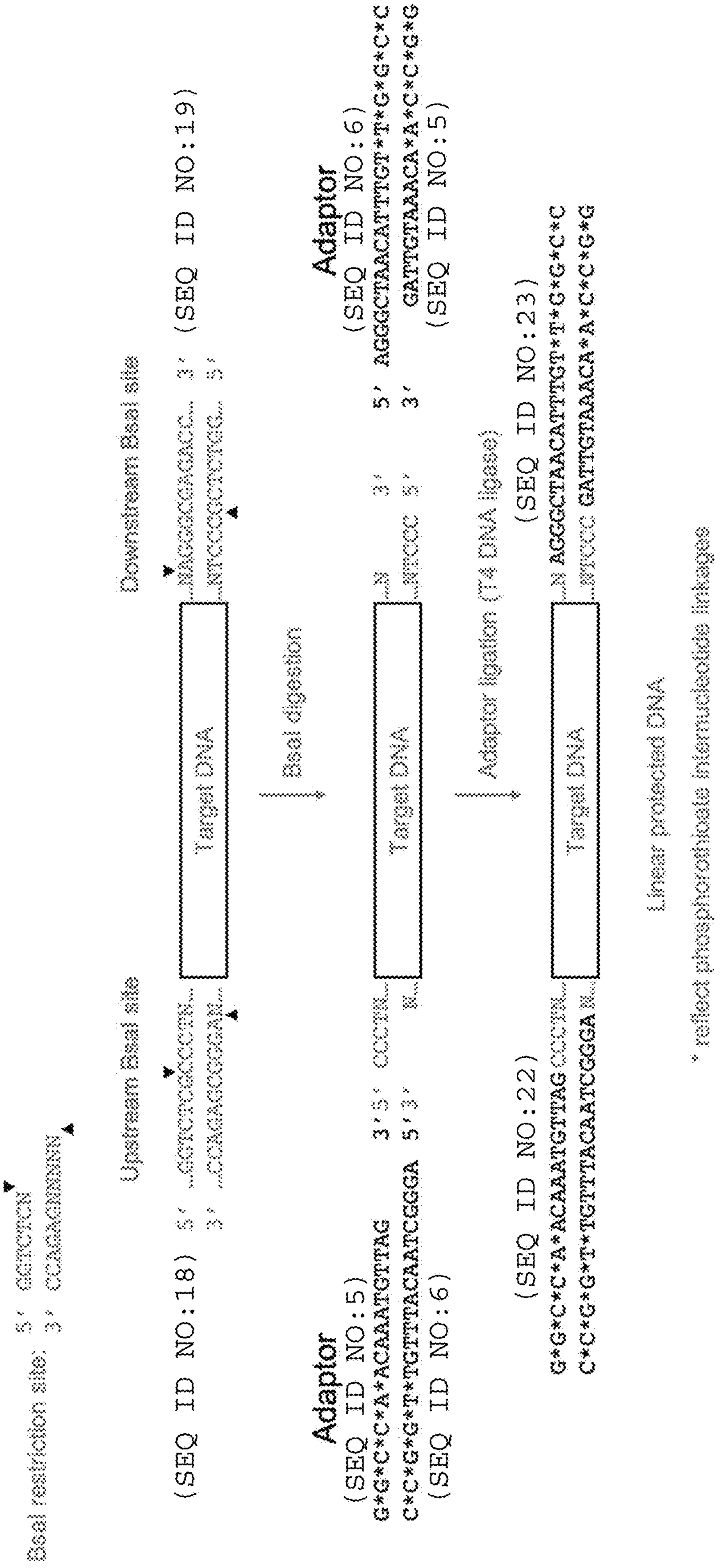
FIG. 4 illustrate the sequences driving adaptor molecules ligation after BsaI digestion of an amplified double-stranded DNA molecule in each cycle of the process. BsaI digestion produces 4-nucleotide protruding ends at 5' (TCCC 5') at both sides of the expression cassette. Adaptors are formed by hybridization of complementary oligonucleotides (SEQ ID NO: 5 and 6) containing phosphorothioate internucleotide linkages (marked as asterisks) and forming a 4-nucleotide protruding end at 5' (GGGA 5'). Adaptor molecules are ligated at both sides of the expression cassette, resulting in linear DNA product which has enhanced resistance to exonuclease, since phosphorothioate internucleotide linkages at both sides and both strands of the expression cassette prevent exonucleolytic degradation of the linear DNA product.
Figure 5:
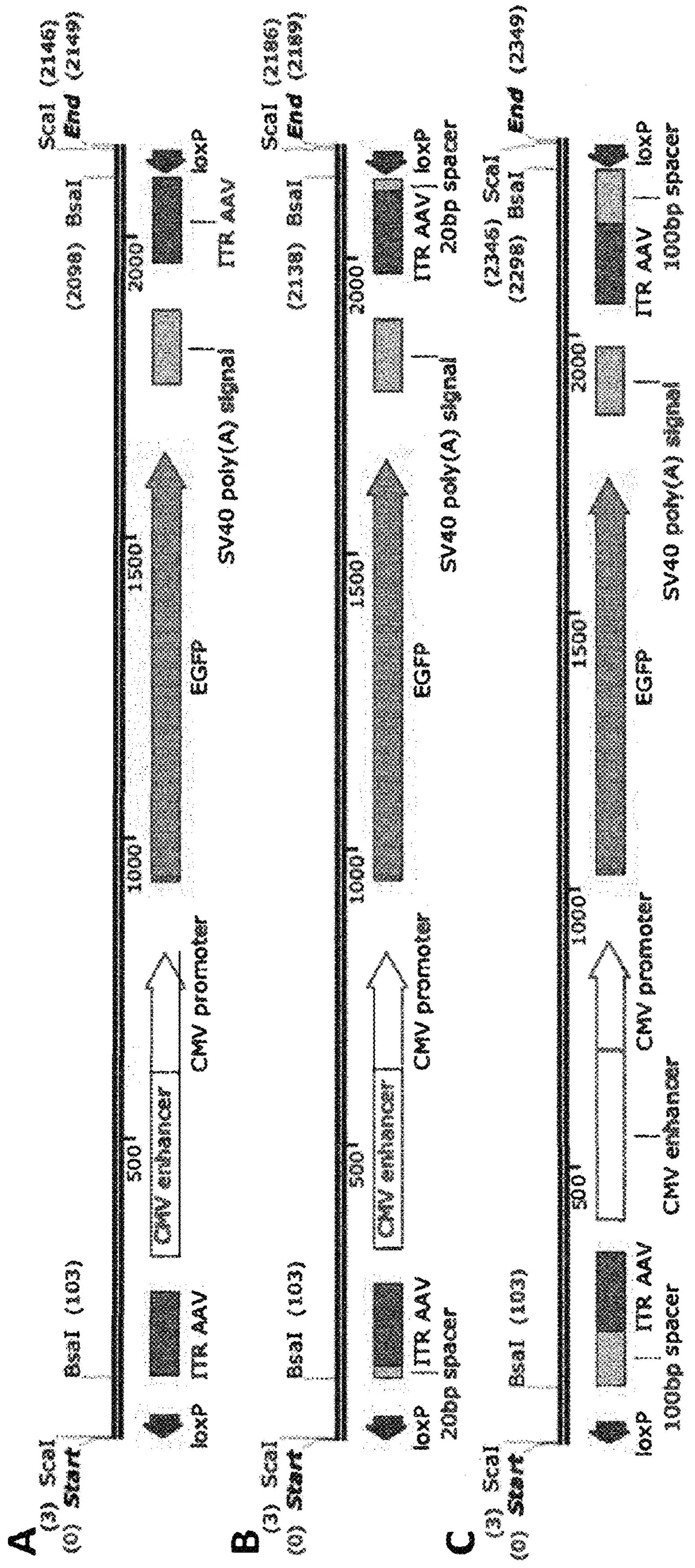
FIG. 5 illustrates the sequence elements of three constructs (A, B and C). The mammalian expression cassettes are formed by CMV promoter (SEQ ID NO: 7) and enhancer (SEQ ID NO: 8), eGFP reporter gene (SEQ ID NO: 9) and SV40 polyA signal (SEQ ID NO: 10). Cassettes are flanked by two LoxP sequences (SEQ ID NO: 3) having the same orientation and two inverted terminal repeats (ITRs, SEQ ID NO: 11), required for adeno-associated virus (AAV) replication and encapsidation of the DNA into viral particles. The difference between the three cassettes is the absence (A) or presence of DNA sequences (B: 20 bp; C: 100 bp) between the ITRs and the BsaI restriction sites at both ends of the cassette.
Figure 6:
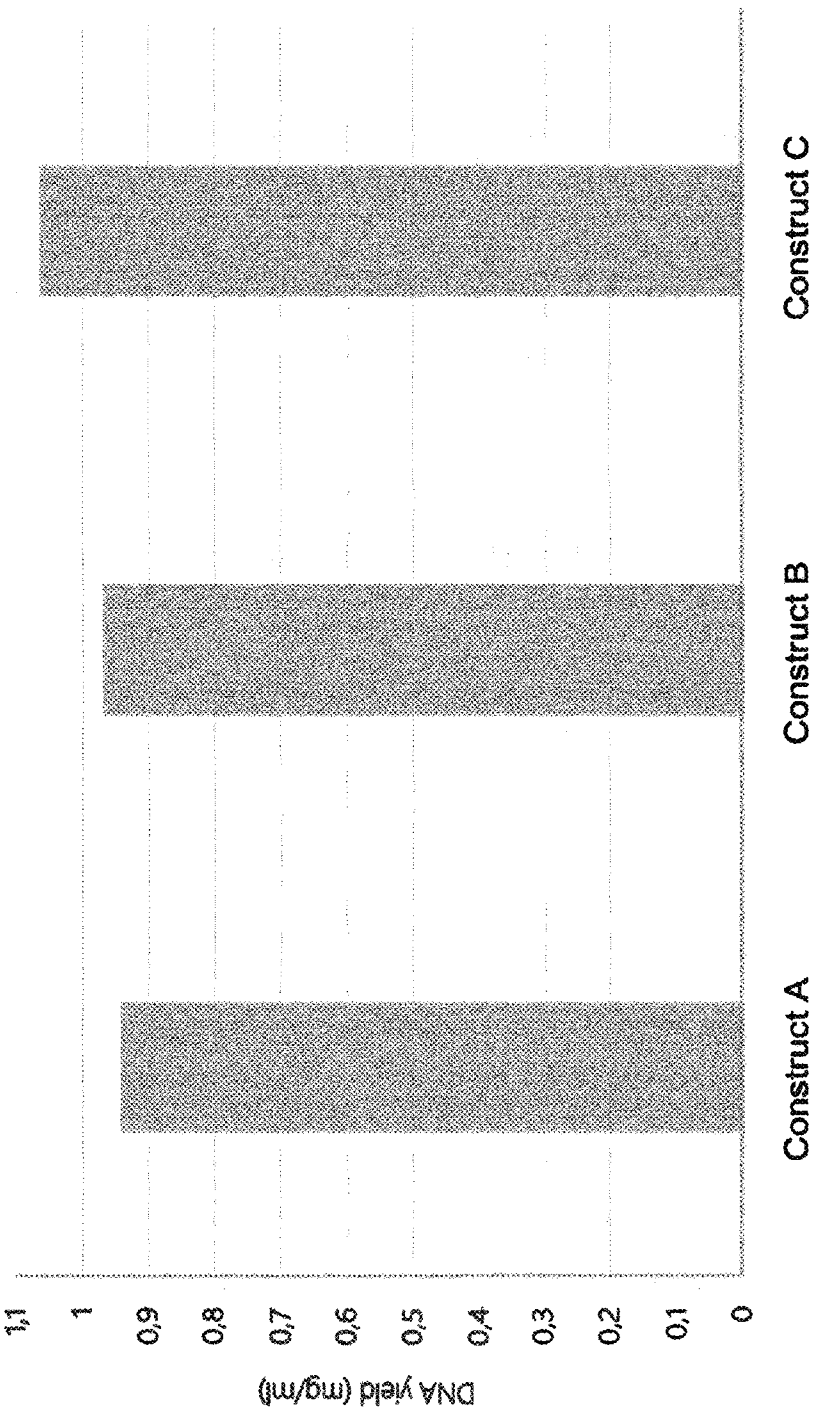
FIG. 6 illustrates Picogreen quantification of the amplification yields of Construct A, Construct B, and Construct C (see FIG. 5), obtained from Cre-derived circular DNA molecules.

Shown in FIG. 6 are the amplification yields of Construct A, Construct B, and Construct C (see FIG. 5), obtained from Cre-derived circular DNA molecules obtained following the procedure schemed in FIG. 2.

Before the amplification, circularized DNA samples were first denatured by adding 1 volume of buffer D (400 mM KOH, 10 mM EDTA) and incubating 3 min at room temperature. Samples were then neutralized by adding 1 volume of buffer N (400 mM HCl, 600 mM Tris-HCl pH 7.5). Rolling circle amplification conditions: 10 ml reaction volume, 1 ml TruePrime WGA reaction buffer 10× (4basebio), 500 µl denatured DNA sample, 1 ml TthPrimPol (1 µM), 160 µl QualiPhi Phi29DNApol (12.5 µM), 2.5 units PPase (Thermo) and 1 ml dNTPs (10 mM). Incubation time and temperature: 20 hours at 30° C. and 10 min at 65° C.

Amplified DNAs were incubated with Type II restriction enzyme BsaI, T4 DNA ligase and complementary adaptors to the 5' protruding ends generated by BsaI on the amplified DNA. Digestion and ligation reaction conditions: reaction volume 100 µl, 10 µl reaction buffer T4 DNA ligase 10× (NEB), 3 µg DNA, 60 units BsaI-HFv2 (NEB), 2000 units T4 DNA ligase (NEB), 480 ng DNA adaptor (1:20 molar excess), incubation time and temperature: 5 minutes at 37° C. and 5 minutes at 16° C. (60 cycles). Exonuclease clean-up reaction conditions: 15 units of *E. coli* exonuclease I (NEB) and 75 units of *E. coli* exonuclease III (NEB) are then added to remove remaining adaptors and open DNA molecules. Incubation time and temperature: 30 minutes at 37° C. and 20 minutes at 80° C.

Figure 7:
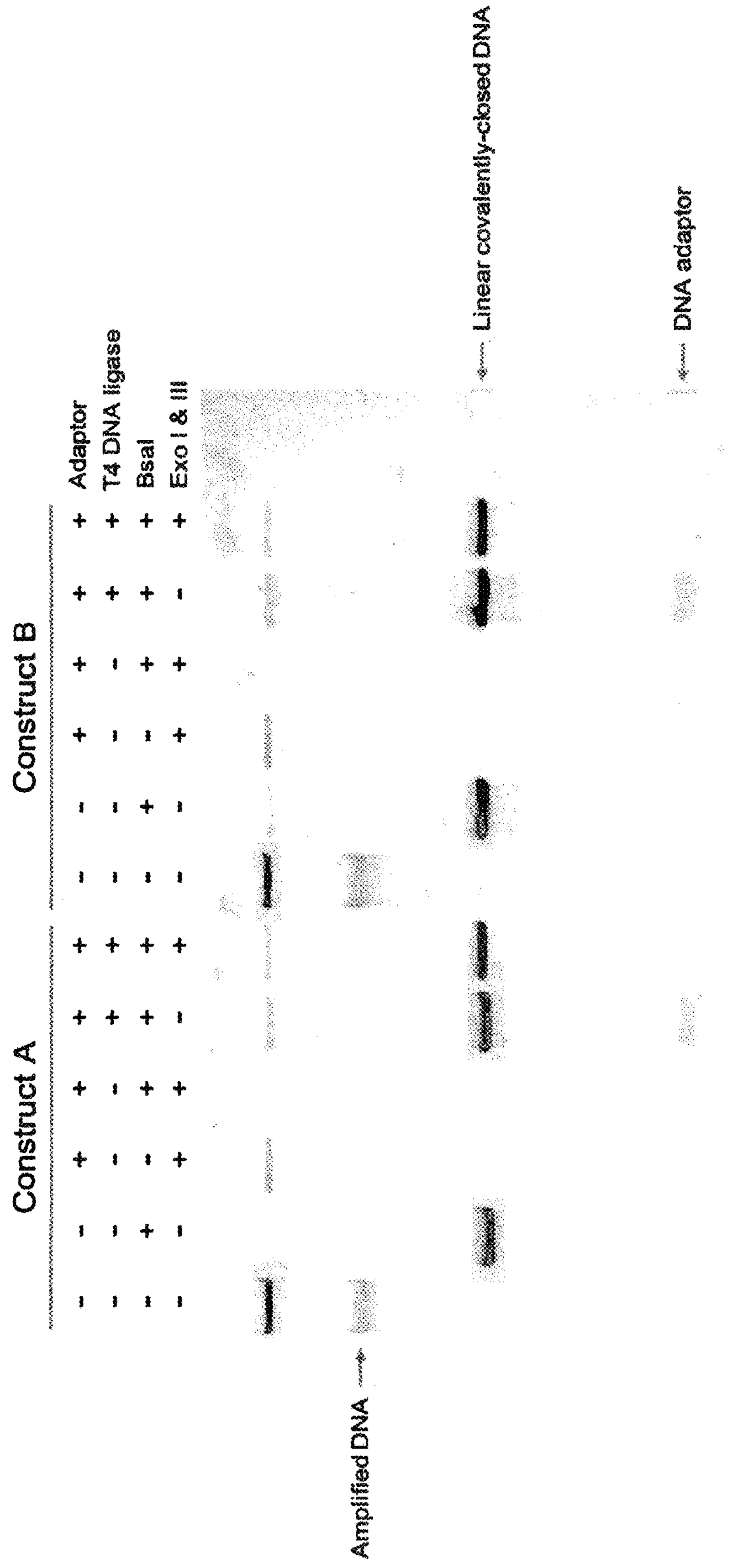
FIG. 7 depicts the analysis of the amplified DNAs (Construct A and Construct B, see FIG. 5) during the digestion and adaptor molecule ligation process by agarose gel electrophoresis (0.8%).

Shown in FIG. 7 is the agarose gel electrophoresis analysis of the amplified DNAs (lanes 1 and 7) digested with the restriction enzyme BsaI (lanes 2 and 8), releasing the unit size of the expression cassette (see FIG. 5). Amplified DNAs and adaptors are degraded by exonucleases I and III (lanes 3 and 9), as well as the amplified DNAs digested with BsaI (lanes 4 and 10), since none of them are covalently closed at both ends to prevent exonuclease degradation. The addition of T4 DNA ligase to the reaction (lanes 5 and 11) allowed the ligation of the adaptors to both ends of each expression cassette generated by BsaI digestion. Finally, exonuclease I and III degraded remaining open DNAs and adaptors, resulting in covalently closed linear DNA molecules (lanes 6 and 12) resistant to exonucleolytic degradation.

Ligation yields obtained from two independent assays for each DNA molecule are summarized in FIG. 8.

Example 2

Figure 9:
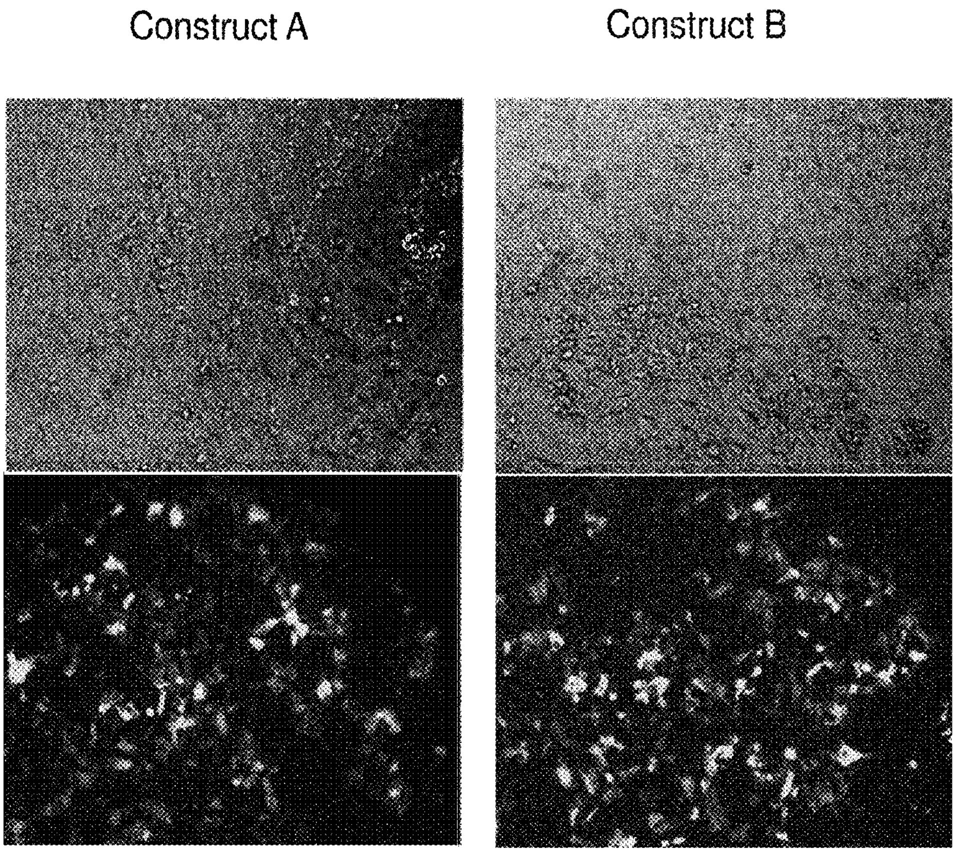
FIG. 9 shows HEK293 cells transfected with covalently closed linear DNA molecules encoding the eGFP reporter gene (i.e. Construct A and Construct B, see FIG. 5). Cells were transfected using JetOptimus, and GFP expression was analysed 48 h post-transfection.
Figure 10A:
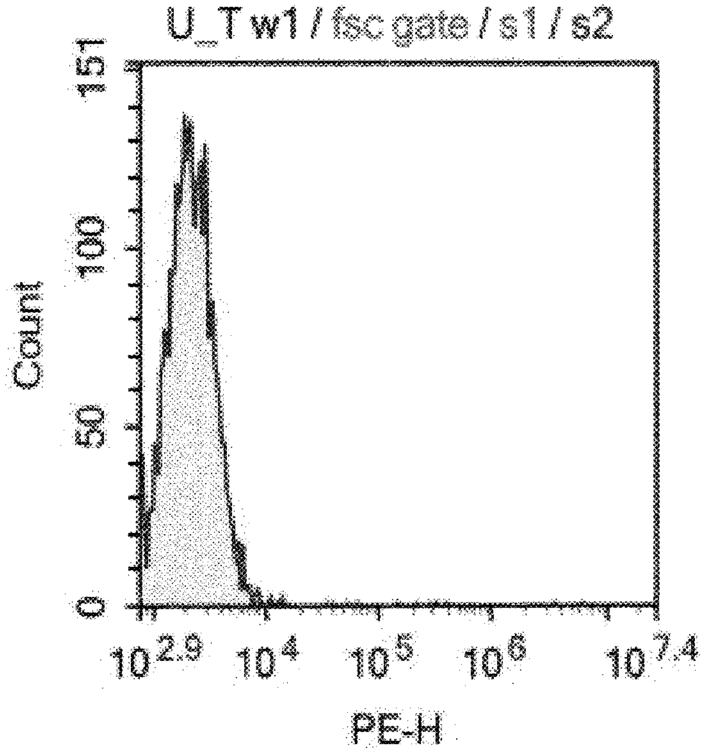
FIG. 10 shows flow cytometry analysis of HEK293 cells transfected with covalently closed linear DNA molecules encoding the eGFP reporter gene. Cells were transfected using Lipofectamine 2000, and GFP expression was analysed 48 h post-transfection. FIG. **10*a* shows a histogram and dot plot of a representative un-transfected sample with no GFP expression.
FIG. 10*b* shows the GFP expression arising from cells transfected with covalently closed linear DNA molecules encoding the eGFP reporter gene with ITRs (Construct A).
FIG. 10*c*** shows the GFP expression arising from cells transfected with covalently closed linear DNA molecules encoding the eGFP reporter gene with ITRs+20 bp spacer (Construct B).
Figure 10A:
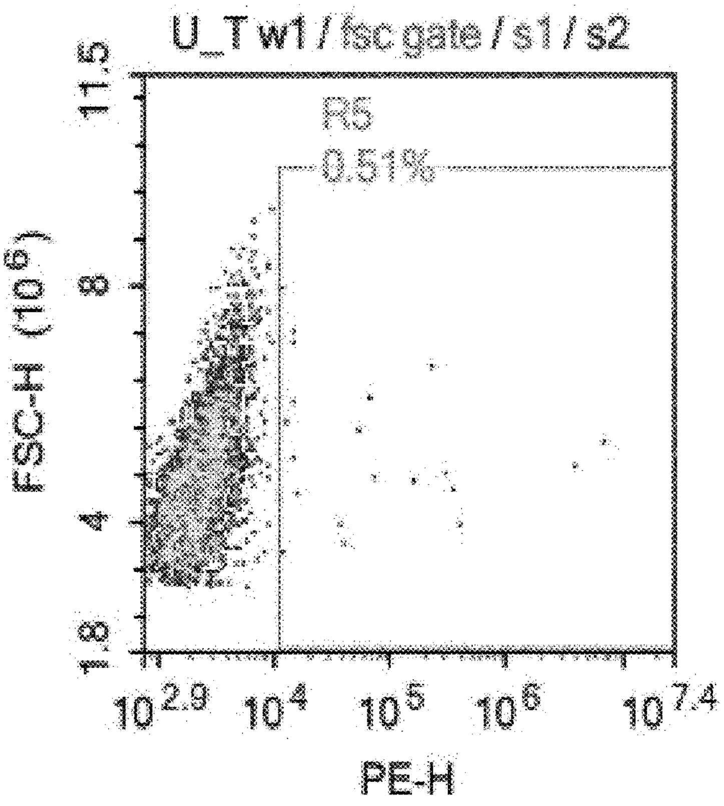
Figure 10B:
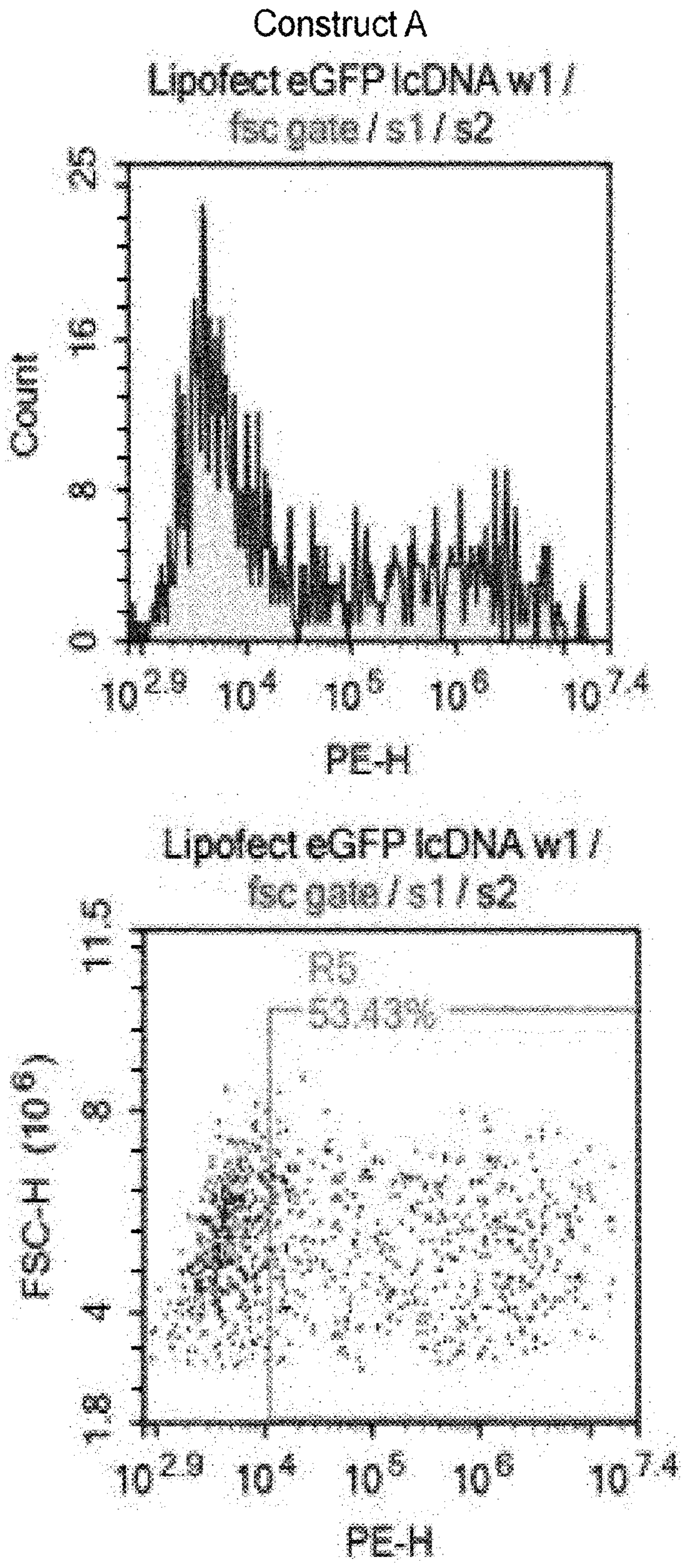
Figure 10C:
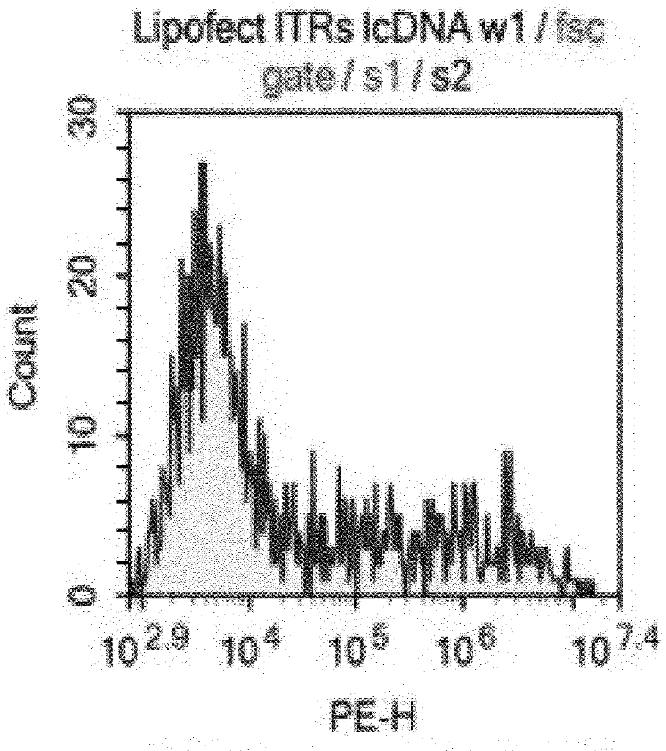
Figure 10C:
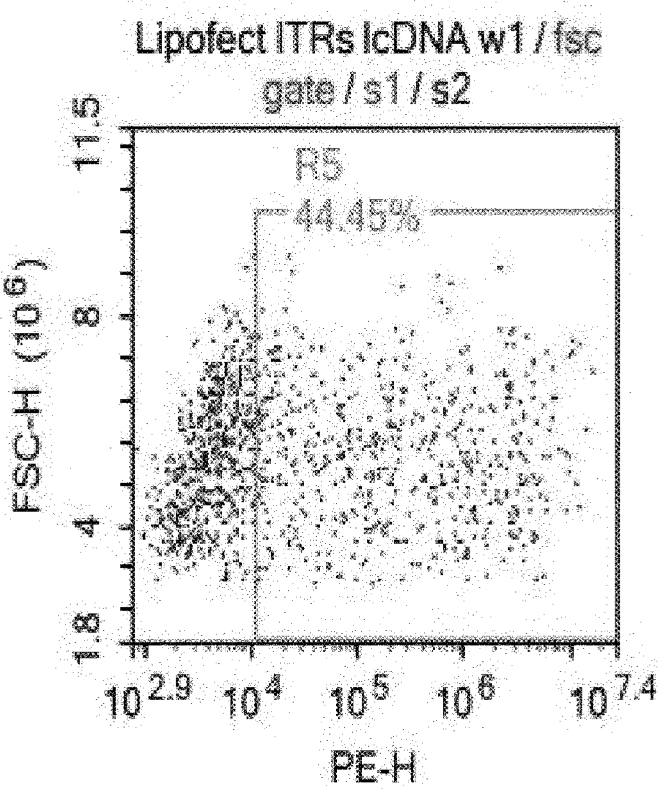

The closed linear DNA product encoding the eGFP reporter gene with ITRs, with and without a 20 bp spacer was transfected into HEK293 cells. Cells were transfected using JetOptimus, and GFP expression was analysed 48 h post-transfection. FIG. 9 shows brightfield and fluorescent microscopy images of cells expressing the GFP protein expressed from the closed linear DNA constructs A and B (see FIG. 5).

FIG. 10 shows flow cytometry analysis of HEK293 cells transfected with covalently closed linear DNA molecules encoding the eGFP reporter gene. Cells were transfected using Lipofectamine 2000, and GFP expression was analysed 48 h post-transfection. FIG. 10*a* shows a histogram and dot plot of a representative un-transfected sample with no GFP expression. FIG. 10*b* shows the GFP expression arising from cells transfected with covalently closed linear DNA molecules encoding the eGFP reporter gene with ITRs (Construct A, FIG. 5). Transfection efficiency was 54.43%. FIG. 10*c* shows the GFP expression arising from cells transfected with covalently closed linear DNA molecules encoding the eGFP reporter gene with ITRs and a 20 bp spacer (Construct B, FIG. 5). Transfection efficiency was 44.45%.

Figure 11:
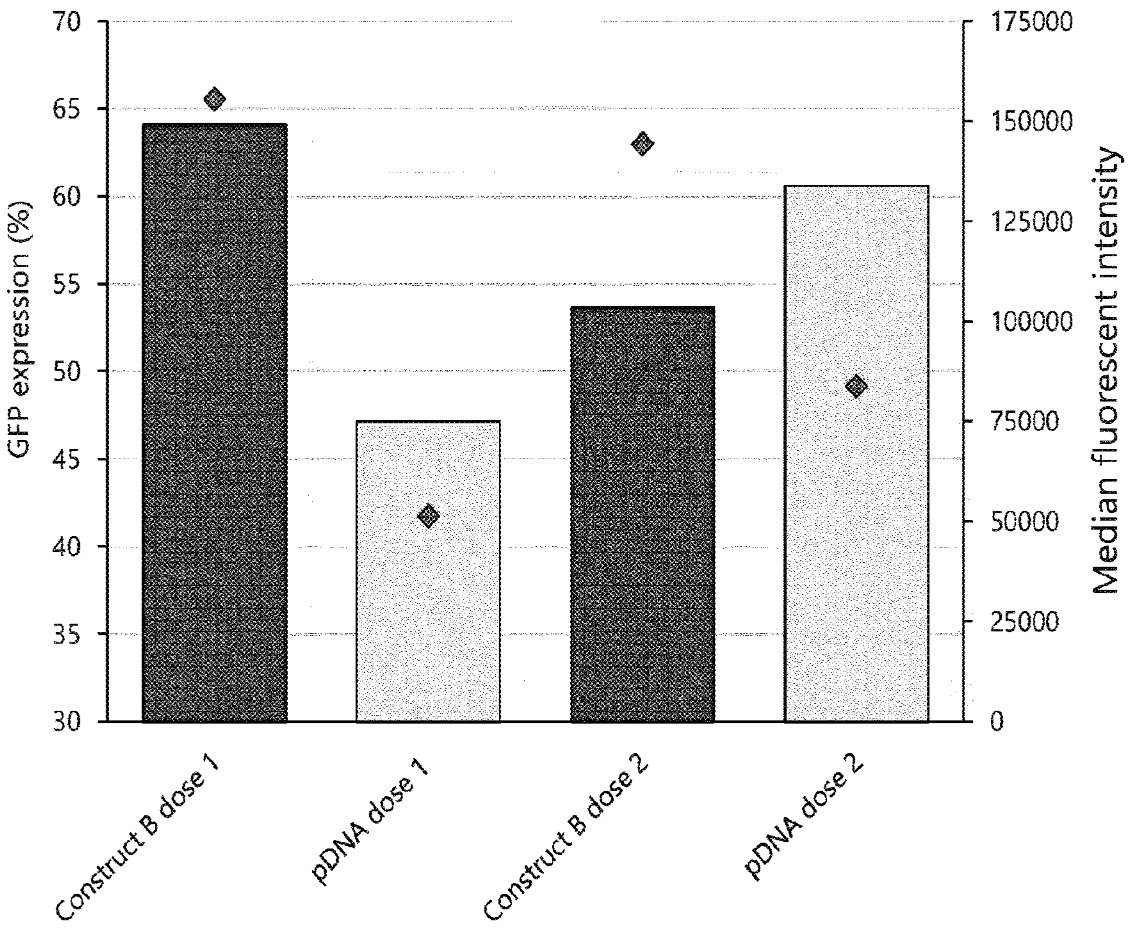
FIG. 11 shows GFP transfection efficiency and median fluorescent intensity of HEK293 suspension cells transfected with linear covalently closed DNA molecules (Construct B) vs pDNA constructs encoding GFP, using PeiPro. GFP expression was measured by flow cytometry 72 h post-transfection.

FIG. 11 shows GFP transfection efficiency and median fluorescent intensity of HEK293 suspension cells transfected with linear covalently closed DNA molecules (Construct B dose 1 and Construct B dose 2) vs pDNA constructs (pDNA dose 1 and pDNA dose 2) encoding GFP, using PeiPro, at a dose of 1 µg or 1.5 µg per ml. GFP expression was measured by flow cytometry 72 h post-transfection. Linear, covalently closed DNA molecules gave a transfection efficiency of 64% at a dose of 1 µg/ml, as compared to pDNA at 47%. Median fluorescent intensity (MFI) was 155,556, as compared to 51,345 for pDNA. At a dose of 1.5 µg/ml, linear, covalently closed DNA molecules gave a transfection efficiency of 53.7%, as compared to pDNA at 60.6%. MFI was 143,353.8, as compared to 83,856 for pDNA.

Figure 12:
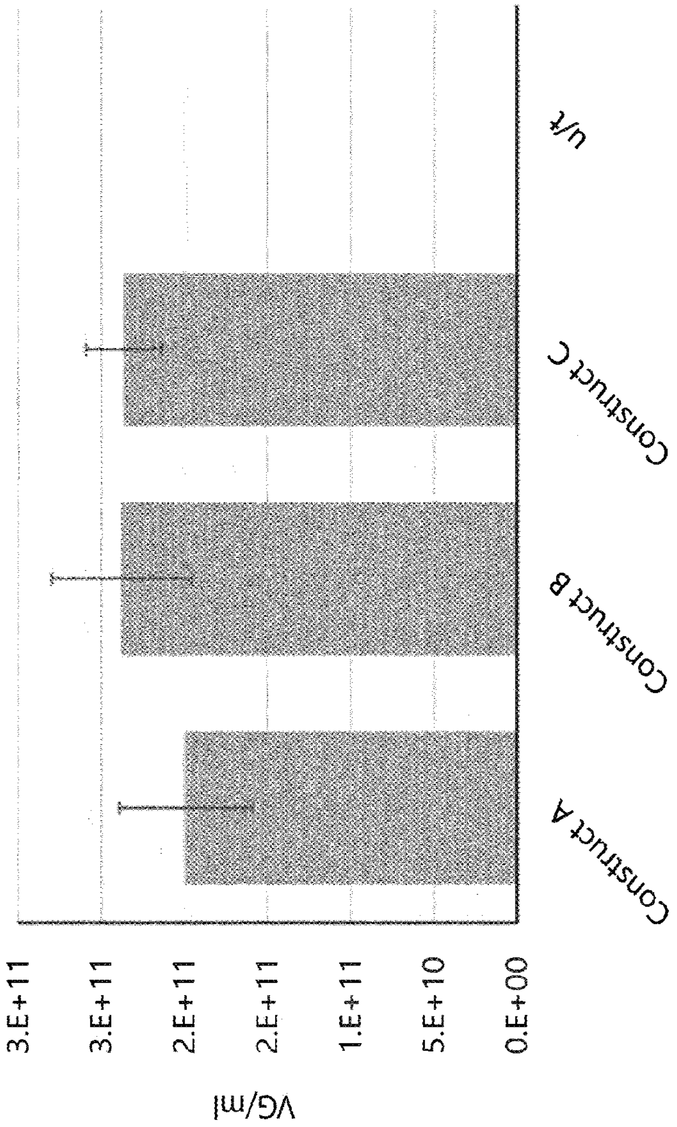
FIG. 12 shows the rAAV5 viral genome titre (VG/ml) of AAV particles produced using covalently closed DNA transgene constructs (Constructs A-C), as measured by qPCR. HEK293 suspension cells were transfected with linear covalently closed DNA transgene constructs, along with RepCap and Helper pDNA using PeiPro transfection reagent, and harvested 72 h post transfection.

FIG. 12 shows the rAAV5 viral genome titre (VG/ml) of AAV particles produced using linear covalently closed DNA transgene constructs (Constructs A, B and C, see FIG. 5), as measured by qPCR. HEK293 suspension cells were transfected with linear covalently closed DNA transgene constructs, along with RepCap and Helper pDNA using PeiPro transfection reagent, and harvested 72 h post transfection. Viral titres ranged from 1.78E+11 to 2.38E+11 across the linear covalently closed DNA transgene constructs.

Figure 13:
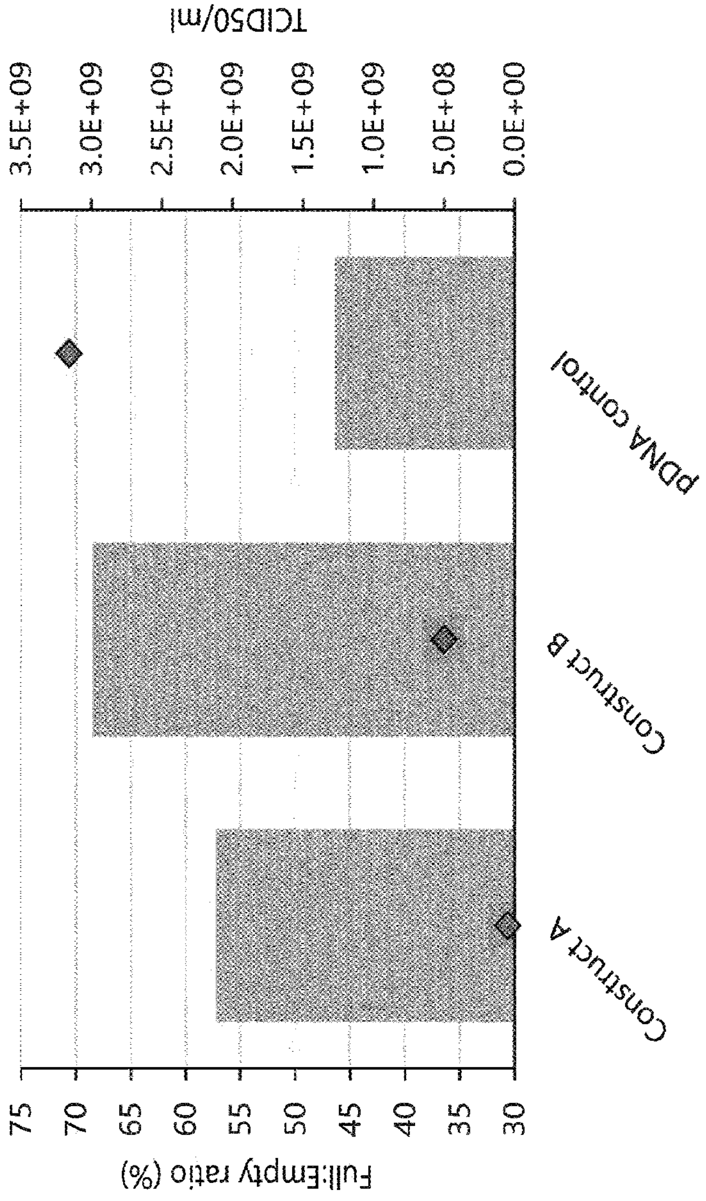
FIG. 13 shows the Full:Empty ratio of AAV particles produced with linear covalently closed DNA transgene constructs (Constructs A & B), as compared to a pDNA control (primary axis). TCID50/ml (Median Tissue Culture Infectious Dose) in HeLaRC32 cells co-dosed with Ad5 is expressed on the secondary axis.

FIG. 13 shows the Full:Empty ratio of AAV particles produced with linear covalently closed DNA transgene constructs (Construct A and Construct B, see FIG. 5), as compared to a pDNA control (primary axis). TCID50/ml (Median Tissue Culture Infectious Dose) in HeLaRC32 cells co-dosed with Ad5 is expressed on the secondary axis. The Full:Empty ratios of linear covalently closed DNA transgene constructs A and B were 57.1% and 68.38% respectively, as compared to the pDNA control, at 46.3%. This suggests that AAV particles produced with linear covalently closed DNA transgene constructs have a higher percentage of capsids that contain the full-length desired transgene, while a lower Full:Empty ratio suggests there are more empty capsids, which can inhibit transduction of the viral particles and therefore the efficacy of the AAV. These impurities may also increase the immunogenicity of the AAV product. The TCID50/ml values for linear covalently closed DNA transgene constructs A and B were 5.01 E+07 and 5.2E+08 respectively, as compared to the pDNA control, at 3.16E+09. This suggests that AAV particles produced with linear covalently closed DNA transgene constructs are more potent, and require a lower concentration to display a cytopathic effect (CPE) in the HeLaRC32 cells.

Figure 14:
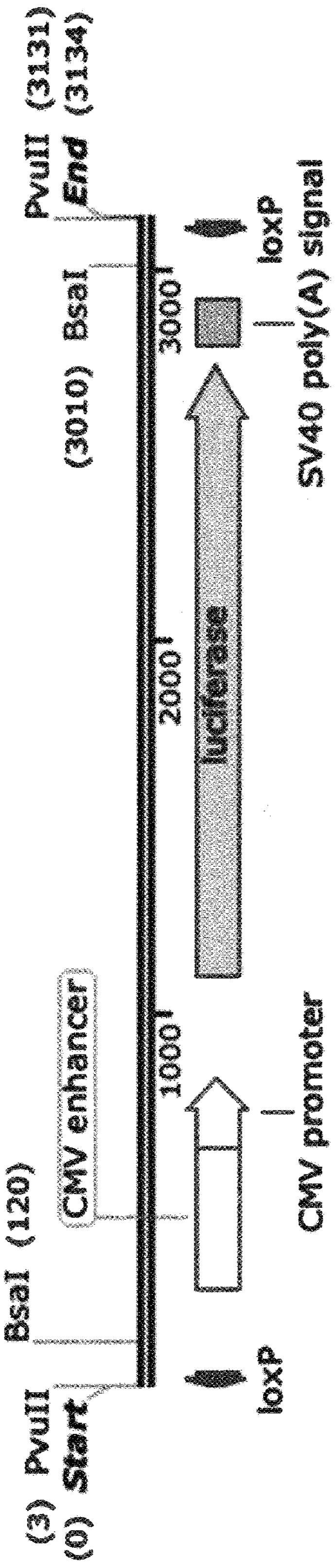
FIG. 14 summarizes the production of covalently closed linear DNA molecules encoding the luciferase reporter gene (SEQ ID NO: 12).
Figure 14:
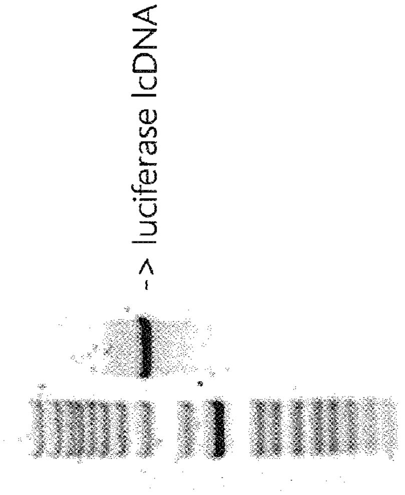

FIG. 14 summarizes the production of covalently closed linear DNA molecules encoding the luciferase reporter gene. A plasmid containing the expression cassette shown in FIG. 14 was subjected to the procedure depicted in FIG. 1. Cre reaction conditions: reaction volume 50 µl, DNA of interest purified from agarose gel electrophoresis after restriction enzyme digestion (100 ng), Cre recombinase (NEB, 4 units), incubation time and temperature: 30 min at 37° C. and 20 min at 80° C. Next, to remove remaining non-circular DNA molecules before the amplification step, *E. coli* exonuclease I (NEB, 20 units) and III (NEB, 100 units) were added and the reaction was incubated 30 min at 37° C. and 20 min at 80° C. Before the amplification, circularized DNA was first denatured by adding 1 volume of buffer D (400 mM KOH, 10 mM EDTA) and incubating 3 min at room temperature. The sample was then neutralized by adding 1 volume of buffer N (400 mM HCl, 600 mM Tris-HCl pH 7.5). Rolling circle amplification conditions: 10 ml reaction volume, 1 ml TruePrime WGA reaction buffer 10× (4basebio), 500 μl denatured DNA sample, 1 ml TthPrimPol (1 μM), 160 μl QualiPhi Phi29DNApol (12.5 μM), 2.5 units PPase (Thermo) and 1 ml dNTPs (10 mM). Incubation time and temperature: 20 hours at 30° C. and 10 min at 65° C. Amplified DNA was then incubated with Type II restriction enzyme BsaI, T4 DNA ligase and complementary adaptors (SEQ ID NO: 4) to the 5' protruding ends generated by BsaI on the amplified DNA. Digestion and ligation reaction conditions: reaction volume 100 μl, 10 μl reaction buffer T4 DNA ligase 10× (NEB), 3 μg DNA, 60 units BsaI-HFv2 (NEB), 2000 units T4 DNA ligase (NEB), 480 ng DNA adaptor (1:20 molar excess), incubation time and temperature: 5 minutes at 37° C. and 5 minutes at 16° C. (60 cycles). Exonuclease clean-up reaction conditions: 15 units of *E. coli* exonuclease I (NEB) and 75 units of *E. coli* exonuclease III (NEB) are then added to remove remaining adaptors and open DNA molecules. Incubation time and temperature: 30 minutes at 37° C. and 20 minutes at 80° C. Shown in FIG. 14 is the agarose gel electrophoresis analysis of the linear closed DNA produced. The table In FIG. 14 shows the efficiency of the linear closed DNA generation process.

Figure 15:
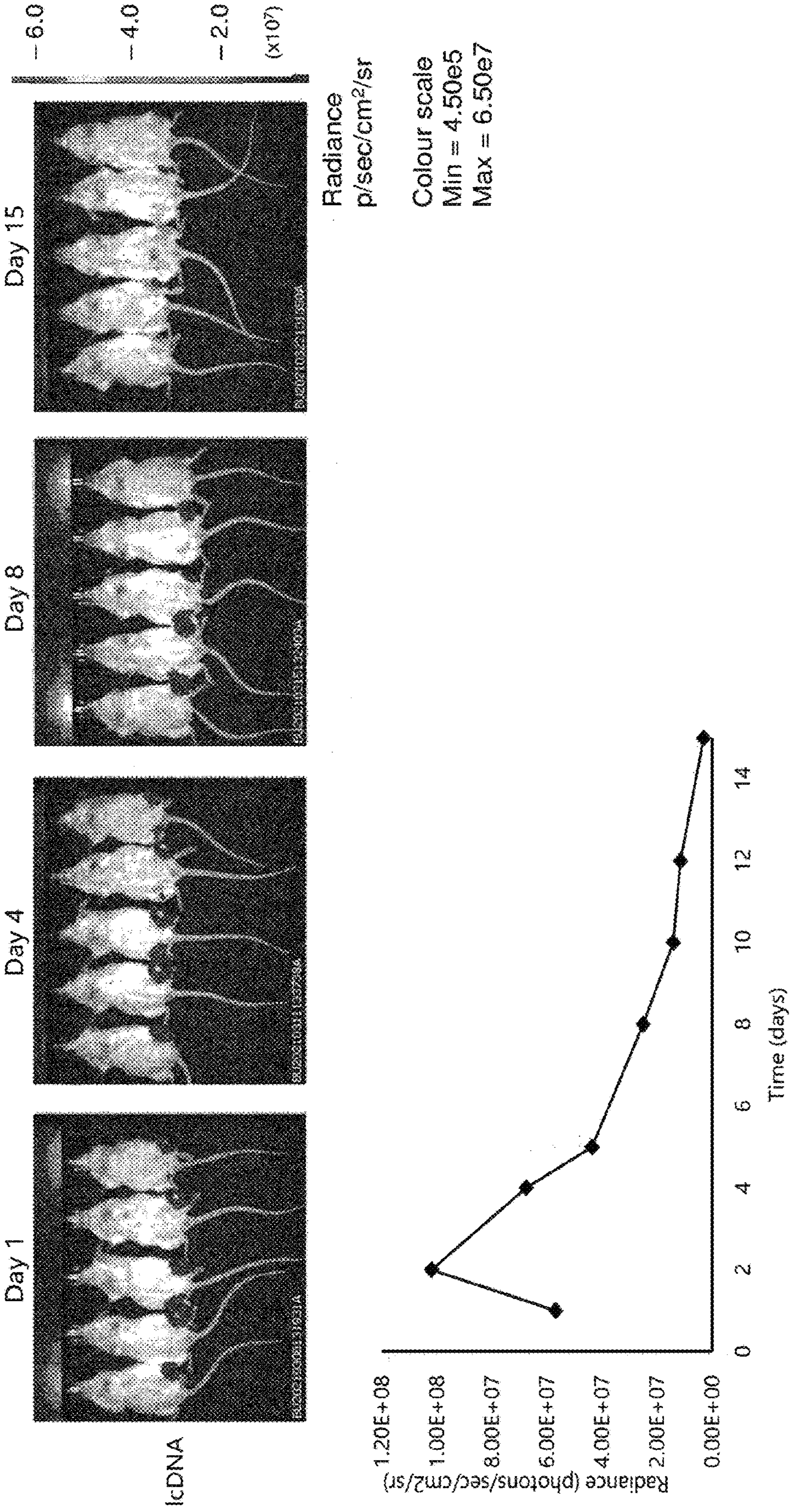
FIG. 15 shows luciferase expression in 6-week-old Swiss female mice. Mice received an Intramuscular injection of covalently closed linear DNA product (IcDNA) encoding the Luciferase transgene, followed by electroporation. On days 1-15 post intramuscular injection, mice received an intraperitoneal injection of D-luciferin (150 mg/kg in 100 ul of PBS) 10 minutes before observation. Optical bioluminescence was observed by IVIS Spectrum system under isoflurane anaesthesia.
Figure 16:
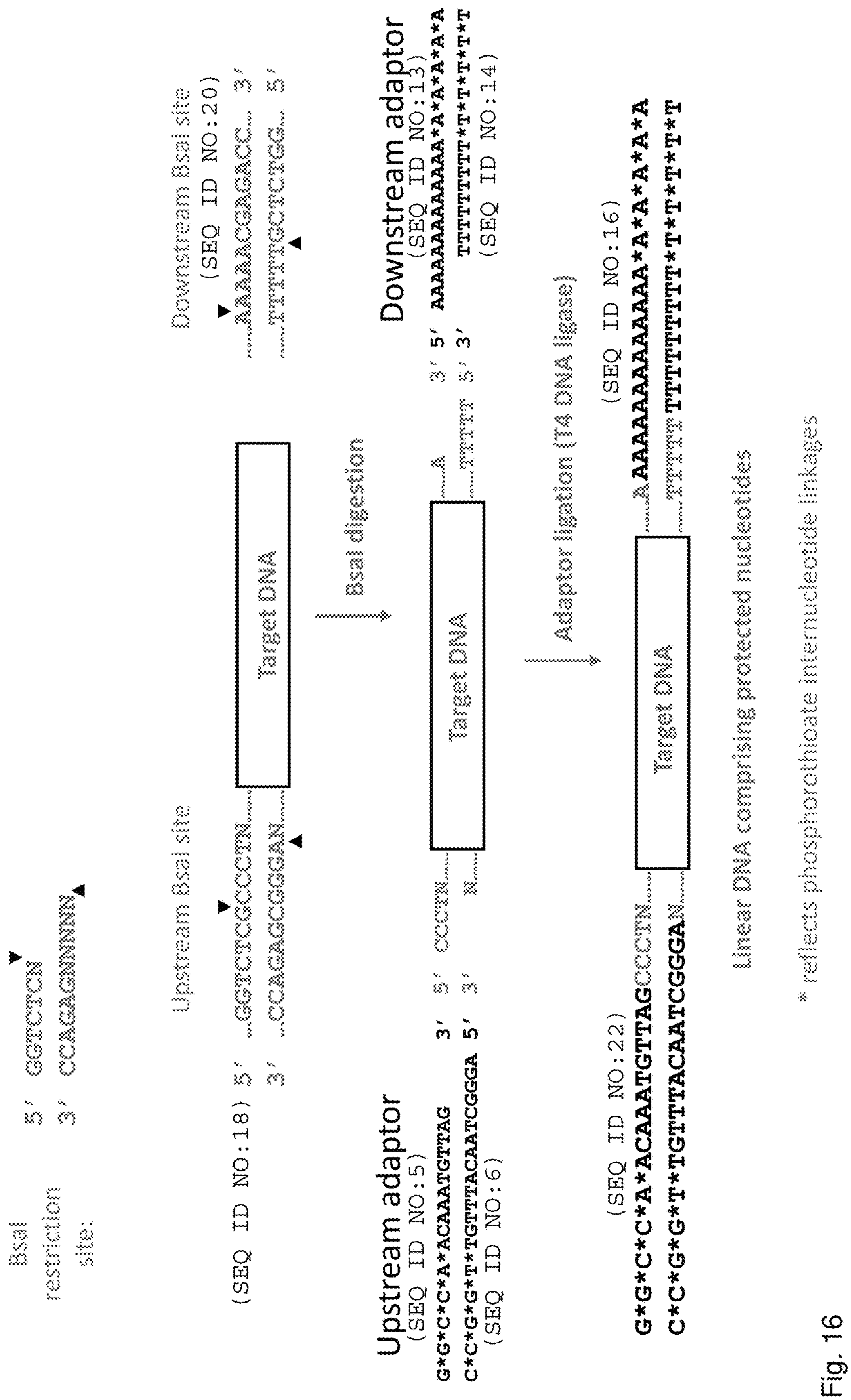
FIG. 16 illustrates the sequences driving adaptor molecules ligation after BsaI digestion of an amplified double-stranded DNA molecule in each cycle of the process. BsaI digestion produces 4-nucleotide protruding ends at 5' (upstream TCCC 5' and downstream TTTT 5') at each side of the expression cassette. Upstream adaptors are formed by hybridization of complementary oligonucleotides (SEQ ID NOs: 22 and 23) containing phosphorothioate internucleotide linkages (marked as asterisks) and forming a 4-nucleotide protruding end at 5' (GGGA 5'). Downstream adaptors are formed by hybridization of complementary oligonucleotides (SEQ ID NOs: 13 and 14) containing phosphorothioate internucleotide linkages (marked as asterisks) and forming a 4-nucleotide protruding end at 5' (AAAA 5'). Complementary adaptor molecules are ligated at each side of the expression cassette, resulting in linear DNA product which has enhanced resistance to exonuclease, since phosphorothioate internucleotide linkages at both sides and both strands of the expression cassette prevent exonucleolytic degradation of the linear DNA product.
Figure 17:
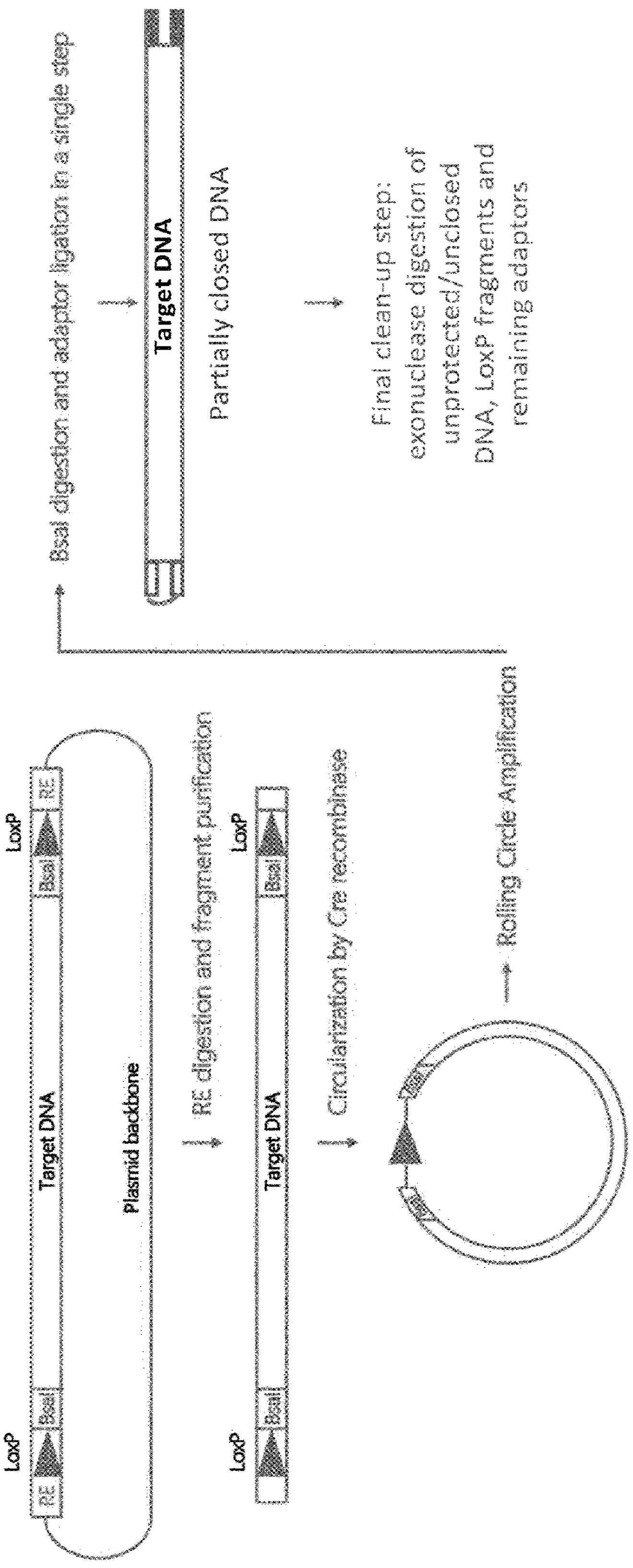
FIG. 17 illustrates the workflow to obtain a linear partially opened DNA product comprising protected nucleotides on one end by digestion and ligation of adaptor molecules in a single step, starting from amplified double-stranded DNA molecule obtained through rolling circle amplification (RCA) of a circular DNA template generated through the action of Cre recombinase on substrates containing two LoxP sequences (SEQ ID NO: 3) flanking the DNA of interest in the same direction.
Figure 18:
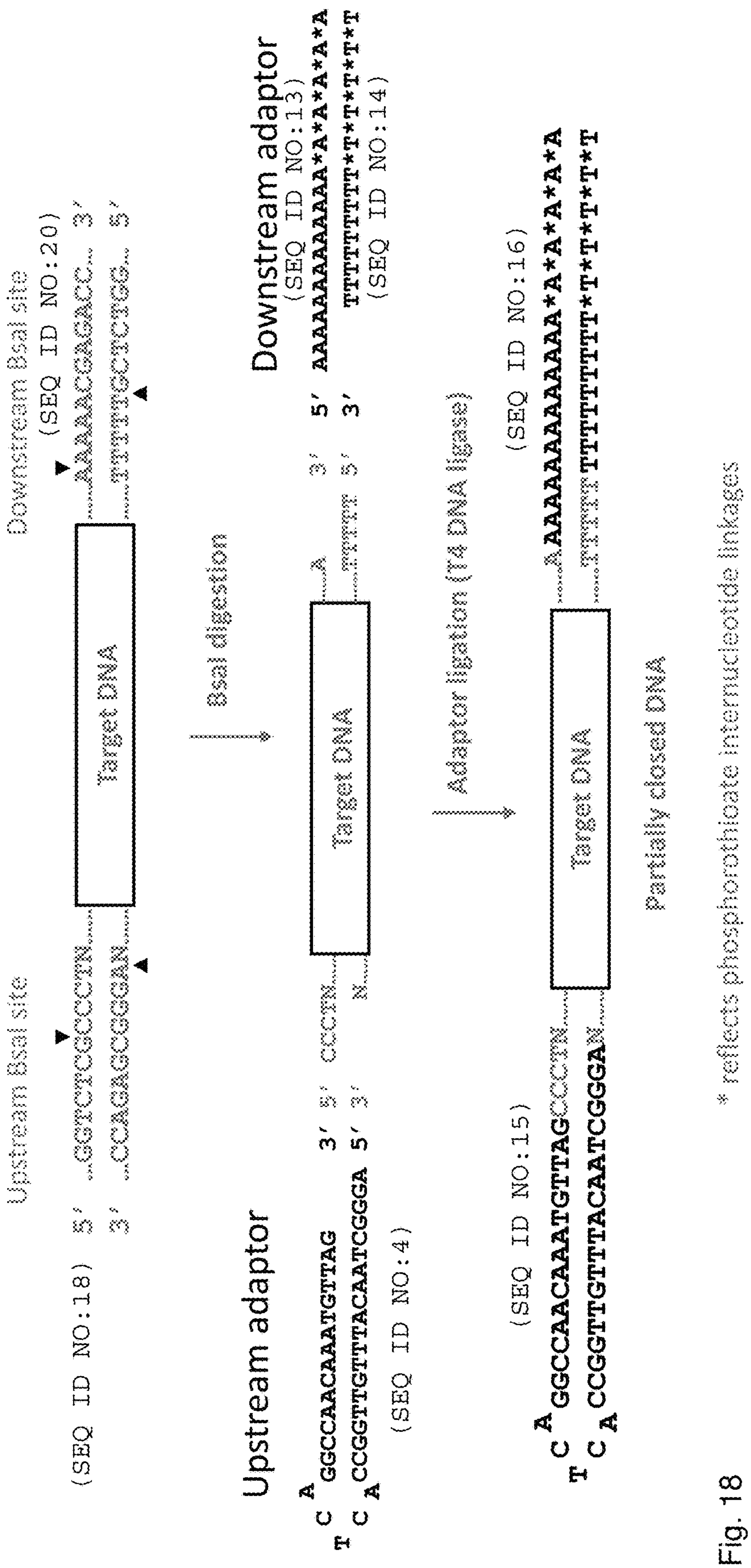
FIG. 18 illustrate the sequences driving adaptor molecules ligation after BsaI digestion of an amplified double-stranded DNA molecule in each cycle of the process. BsaI digestion produces 4-nucleotide protruding ends at 5' (upstream TCCC 5' and downstream TTTT 5') at each side of the expression cassette. Self-complementary adaptor molecules (SEQ ID NO: 4 containing a 4-nucleotide protruding end at 5' (GGGA 5') is then ligated at the upstream side of the expression cassette. Downstream adaptors are formed by hybridization of complementary oligonucleotides (SEQ ID NO: 13 and 14) containing phosphorothioate internucleotide linkages (marked as asterisks) and forming a 4-nucleotide protruding end at 5' (AAAA 5'). Complementary adaptor molecules are ligated at each side of the expression cassette, resulting in linear partially opened DNA product which has enhanced resistance to exonuclease, since phosphorothioate internucleotide linkages at one sides of the expression cassette prevent exonucleolytic degradation of the linear DNA product.

FIG. 15 shows luciferase expression in 6-week-old Swiss female mice. Mice received an Intramuscular injection of covalently closed linear DNA molecules encoding the Luciferase transgene, followed by electroporation. On days 1-15 post intramuscular injection, mice received an intraperitoneal injection of D-luciferine (150 mg/kg in 100 ul of PBS) 10 minutes before observation. Optical bioluminescence was observed by IVIS Spectrum system under isoflurane anaesthesia. Luciferase protein expression from the covalently closed linear DNA molecules encoding the luciferase transgene peaked at day 2, and gradually decreased over the course of 15 days.

Example 3

Figure 19:
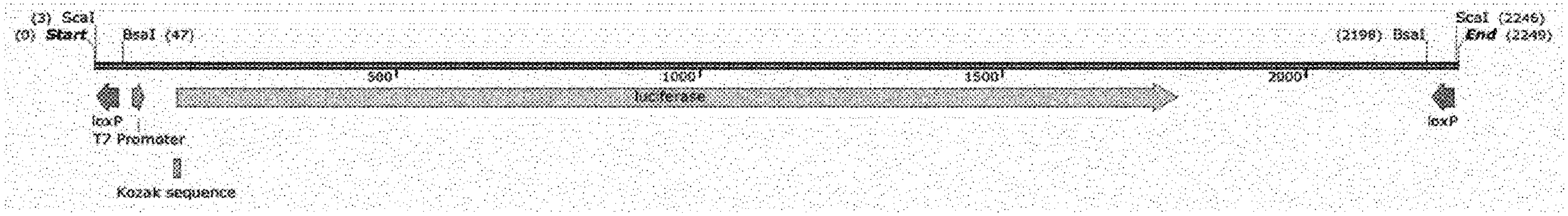
FIG. 19 summarizes the production of a partially closed linear DNA product (opDNA) and linear DNA product comprising protected nucleotides (oeDNA) encoding the luciferase reporter gene for IVT (SEQ ID NO: 24).
Figure 19:
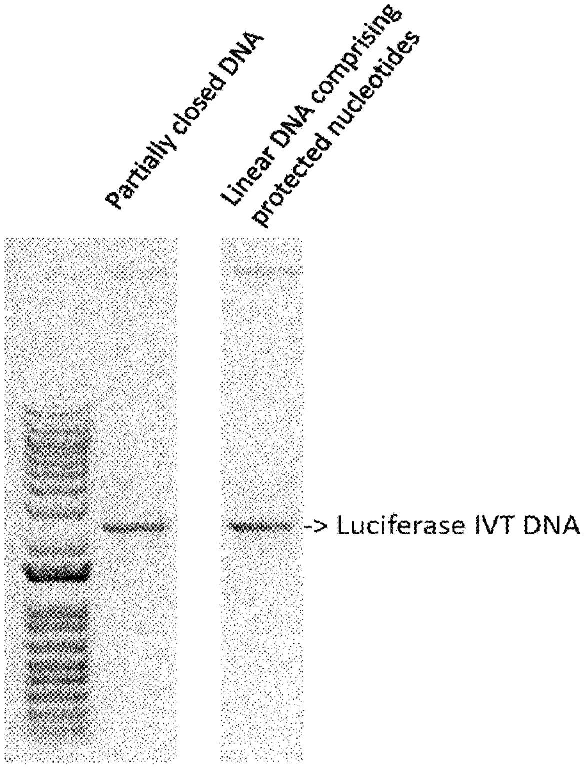
Figure 20:
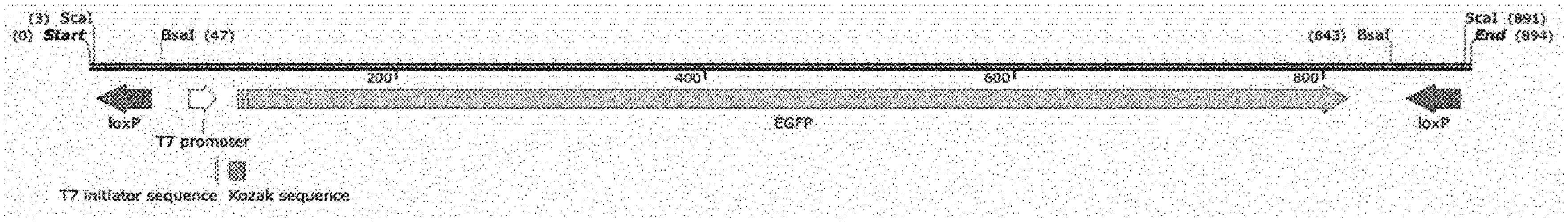
FIG. 20 summarizes the production of a partially closed linear DNA product (opDNA) and linear DNA product comprising protected nucleotides (oeDNA) encoding the GFP reporter gene for IVT (SEQ ID NO: 25).
Figure 20:
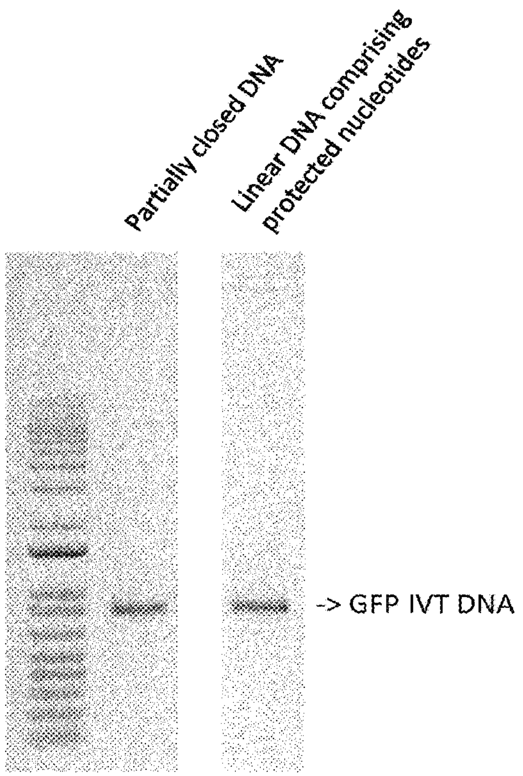

FIGS. 3, 16, 17 and 18 summarize the production of partially closed linear DNA product and linear DNA product comprising protected nucleotides. The two DNA products encode the GFP reporter gene for IVT (SEQ ID NO: 25). A plasmid containing the expression cassette shown in FIG. 20 was subjected to the procedure depicted in FIGS. 3, 16, 17 and 18 to generate partially closed linear DNA product and linear DNA product comprising protected nucleotides, respectively. Cre reaction conditions: reaction volume 1 ml, DNA of interest purified after restriction enzyme digestion (2 ng/μl), Cre recombinase (NEB, 0.08 units/μl), incubation time and temperature: 30 min at 37° C. and 20 min at 80° C. Next, to remove remaining non-circular DNA molecules before the amplification step, *E. coli* exonuclease I (NEB, 0.4 units/μl) and III (NEB, 2 units/μl) were added and the reaction was incubated 30 min at 37° C. and 20 min at 80° C. Before the amplification, circularized DNA was first denatured by adding 1 volume of buffer D (400 mM KOH, 10 mM EDTA) and incubating 3 min at room temperature. The sample was then neutralized by adding 1 volume of buffer N (400 mM HCl, 600 mM Tris-HCl pH 7.5). Rolling circle amplification conditions: 20 ml reaction volume, 2 ml TruePrime WGA reaction buffer 10× (4basebio), 3 ml denatured DNA sample, 2 ml TthPrimPol (1 μM), 320 μl QualiPhi Phi29DNApol (12.5 μM), 5 units PPase (Thermo) and 2 ml dNTPs (10 mM). Incubation time and temperature: 20 hours at 30° C. and 10 min at 65° C. Amplified DNA was then incubated with Type II restriction enzyme BsaI, T4 DNA ligase and complementary adaptors (either SEQ ID NOs: 4, 13 and 14 or SEQ ID NOs: 1, 2, 13 and 14) to the 5' protruding ends generated by BsaI on the amplified DNA. Digestion and ligation reaction conditions: reaction volume 20 ml, 2 ml reaction buffer T4 DNA ligase 10× (NEB), 120 ng/μl amplified DNA, 0.6 units/μl BsaI-HFv2 (NEB), 20 units/μl T4 DNA ligase (NEB), DNA adaptor (1:10 molar excess), incubation time and temperature: 23 hours at 30° C. Exonuclease clean-up reaction conditions: 0.15 units/μl of *E. coli* exonuclease I (NEB) and 0.75 units/μl of *E. coli* exonuclease III (NEB) are then added to remove remaining adaptors and open DNA molecules. Incubation time and temperature: 2 hours at 37° C. Shown in FIG. 19 is the agarose gel electrophoresis analysis of the partially closed linear DNA product and linear DNA product comprising protected nucleotides produced. The table In FIG. 20 shows the efficiency of the partially closed linear DNA product and linear DNA product comprising protected nucleotides generation process.

FIGS. 3, 16, 17 and 18 summarize the production of partially closed linear DNA product and linear DNA product comprising protected nucleotides encoding the luciferase reporter gene for IVT (SEQ ID NO: 24). A plasmid containing the expression cassette shown in FIG. 19 was subjected to the procedure depicted in FIGS. 3, 16, 17 and 18 to generate partially closed linear DNA product and linear DNA product comprising protected nucleotides. Cre reaction conditions: reaction volume 1 ml, DNA of interest purified after restriction enzyme digestion (2 ng/μl), Cre recombinase (NEB, 0.08 units/μl), incubation time and temperature: 30 min at 37° C. and 20 min at 80° C. Next, to remove remaining non-circular DNA molecules before the amplification step, *E. coli* exonuclease I (NEB, 0.4 units/μl) and III (NEB, 2 units/μl) were added and the reaction was incubated 30 min at 37° C. and 20 min at 80° C. Before the amplification, circularized DNA was first denatured by adding 1 volume of buffer D (400 mM KOH, 10 mM EDTA) and incubating 3 min at room temperature. The sample was then neutralized by adding 1 volume of buffer N (400 mM HCl, 600 mM Tris-HCl pH 7.5). Rolling circle amplification conditions: 20 ml reaction volume, 2 ml TruePrime WGA reaction buffer 10× (4basebio), 3 ml denatured DNA sample, 2 ml TthPrimPol (1 μM), 320 μl QualiPhi Phi29DNApol (12.5 μM), 5 units PPase (Thermo) and 2 ml dNTPs (10 mM). Incubation time and temperature: 20 hours at 30° C. and 10 min at 65° C. Amplified DNA was then incubated with Type II restriction enzyme BsaI, T4 DNA ligase and complementary adaptors (either SEQ ID NOs:4, 13 and 14 or SEQ ID NOs: 1, 2, 13, and 14) to the 5' protruding ends generated by BsaI on the amplified DNA. Digestion and ligation reaction conditions: reaction volume 20 ml, 2 ml reaction buffer T4 DNA ligase 10× (NEB), 120 ng/μl amplified DNA, 0.6 units/μl BsaI-HFv2 (NEB), 20 units/μl T4 DNA ligase (NEB), DNA adaptor (1:10 molar excess), incubation time and temperature: 23 hours at 30° C. Exonuclease clean-up reaction conditions: 0.15 units/μl of *E. coli* exonuclease I (NEB) and 0.75 units/μl of *E. coli* exonuclease III (NEB) are then added to remove remaining adaptors and open DNA molecules. Incubation time and temperature: 2 hours at 37° C. Shown in FIG. 19 is the agarose gel electrophoresis analysis of the partially closed linear DNA product and linear DNA product comprising protected nucleotides produced. The table In FIG. 19 shows the efficiency of the partially closed linear DNA product and linear DNA product comprising protected nucleotides generation process.

Figure 21:
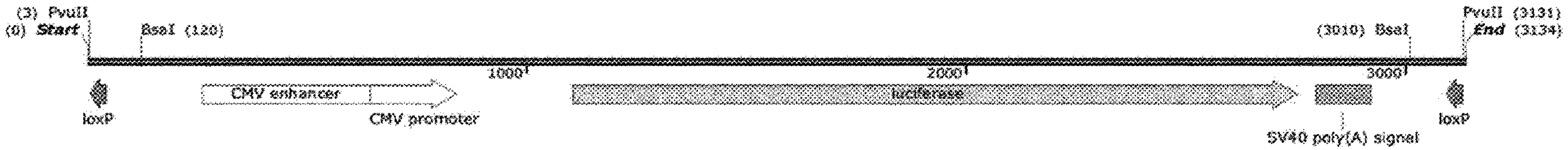
FIG. 21 summarizes the production of closed linear DNA product (hpDNA) and linear DNA product comprising protected nucleotides (oeDNA) encoding the luciferase reporter gene for mammalian expression (SEQ ID NO:12).
Figure 21:
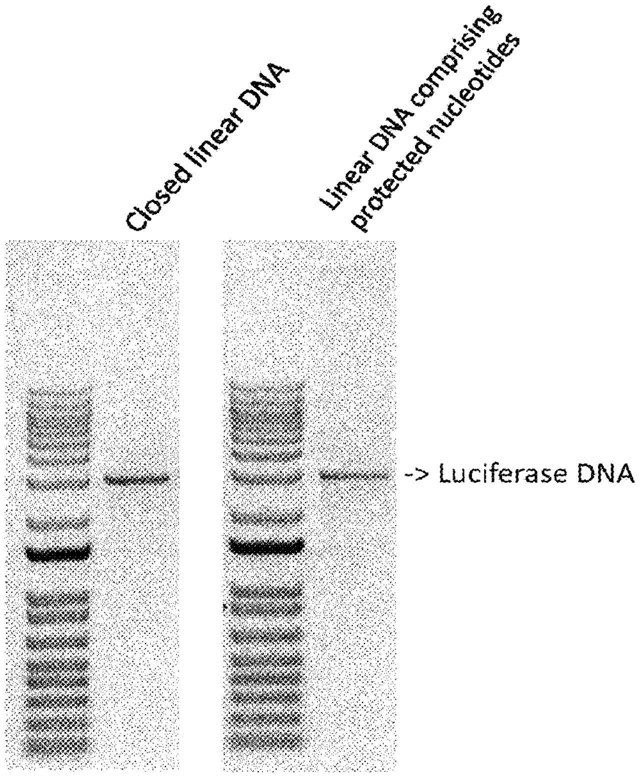

FIG. 21 summarizes the production of closed linear DNA product and linear DNA product comprising protected nucleotides encoding the luciferase reporter gene for mammalian cell expression (SEQ ID NO: 12). A plasmid containing the expression cassette shown in FIG. 21 was subjected to the procedure depicted in FIGS. 1-4 to generate closed linear DNA product (hpDNA) and linear DNA product comprising protected nucleotides (oeDNA). Cre reaction conditions: reaction volume 1 ml, DNA of interest purified after restriction enzyme digestion (2 ng/μl), Cre recombinase (NEB, 0.08 units/μl), incubation time and temperature: 30 min at 37° C. and 20 min at 80° C. Next, to remove remaining non-circular DNA molecules before the amplification step, *E. coli* exonuclease I (NEB, 0.4 units/μl) and III (NEB, 2 units/μl) were added and the reaction was incubated 30 min at 37° C. and 20 min at 80° C. Before the amplification, circularized DNA was first denatured by adding 1 volume of buffer D (400 mM KOH, 10 mM EDTA) and incubating 3 min at room temperature. The sample was then neutralized by adding 1 volume of buffer N (400 mM HCl, 600 mM Tris-HCl pH 7.5). Rolling circle amplification conditions: 20 ml reaction volume, 2 ml TruePrime WGA reaction buffer 10× (4basebio), 3 ml denatured DNA sample, 2 ml TthPrimPol (1 μM), 320 μl QualiPhi Phi29DNApol (12.5 μM), 5 units PPase (Thermo) and 2 ml dNTPs (10 mM). Incubation time and temperature: 20 hours at 30° C. and 10 min at 65° C. Amplified DNA was then incubated with Type II restriction enzyme BsaI, T4 DNA ligase and complementary adaptors (either SEQ ID NO: 4 or SEQ ID NOs: 1 and 2) to the 5' protruding ends generated by BsaI on the amplified DNA. Digestion and ligation reaction conditions: reaction volume 20 ml, 2 ml reaction buffer T4 DNA ligase 10× (NEB), 120 ng/μl amplified DNA, 0.6 units/μl BsaI-HFv2 (NEB), 20 units/μl T4 DNA ligase (NEB), DNA adaptor (1:10 molar excess), incubation time and temperature: 23 hours at 30° C. Exonuclease clean-up reaction conditions: 0.15 units/μl of *E. coli* exonuclease I (NEB) and 0.75 units/μl of *E. coli* exonuclease III (NEB) are then added to remove remaining adaptors and open DNA molecules. Incubation time and temperature: 2 hours at 37° C. Shown in FIG. 21 is the agarose gel electrophoresis analysis of the closed linear DNA product and linear DNA product comprising protected nucleotides produced. The table In FIG. 21 shows the efficiency of the linear partially opened and opened protected DNA generation process.

Example 4—In Vitro Transcription

1 μg of input DNA template was used per sample, then 2 μL 10×T7-FlashScribe™ Transcription Buffer (CellScript), 9 mM ATP, 9 mM CTP (CellScript), 9 mM N1-Methylpseudo-UTP (TriLink), 8 mM ARCA cap structure analog (NEB), 9 mM GTP, 10 mM DTT (CellScript), 0.2 U inorganic pyrophosphatase (Thermo Scientific), 20 U ScriptGuard™ RNase Inhibitor, 2 μL T7-FlashScribe™ Enzyme Solution (CellScript). Incubation time and temperature: 1.5 hour at 37° C. A following DNase I treatment at 1 U was applied (CellScript), incubation time and temperature: 15 min at 37° C.

Example 5—Formaldehyde Denaturing Agarose Gel Electrophoresis 0.8% agarose gel was prepared with 0.7% formaldehyde. Samples were prepared using Formaldehyde Load dye (Invitrogen) and heat denatured at 65° C. for 5 min before addition to the well. Samples were run for 70 min at 80V before imaging.

Example 6—Transfection of HEK Cells—Luciferase mRNA

HEK293 cells were cultured in Dulbecco's Modified Eagle Medium (DMEM) (Gibco cat. no: 11965084) with 10% Fetal Bovine Serum (FBS) (Gibco, cat. no: 16140-071) and 1% Penicillin/Streptomycin (Gibco cat. no: 15070-063).

Transfections in HEK293 cells were performed with commercially available transfection reagent Lipofectamine2000 (ThermoFisher cat. no: 11668019).

Transfections were performed in a 96-well plate at a density of 25×103 cells per well seeded one day prior to transfection.

300 ng of mRNA per well diluted in 50 ul of OptiMEM while 0.5 ul of Lipofectamine2000 was diluted into 50 ul of OptiMEM. The components were incubated for 5 minutes separately then mixed thoroughly and incubated for a further 25 minutes before adding 100 ul OptiMEM to the wells.

All conditions were performed in triplicate. Cells were incubated at 37° C. with 5% CO2. 4 hours post-transfection, the cells were rinsed in PBS, before resuspension in Reporter Lysis buffer (Promega). Plates were incubated at 4° C. for 20 minutes, before −80° C. for 40 minutes. After thawing, luciferase activity was measured following injection of the luciferase assay substrate on the ClarioSTAR plus plate reader (BMG Labtech, Aylesbury, UK). Luciferase expression was normalised to protein content using Pierce BCA Protein Assay, with absorbance measured at 562 nm. Luciferase activity was expressed as Relative Light Units per mg of protein (RLU/mg).

Figure 25:
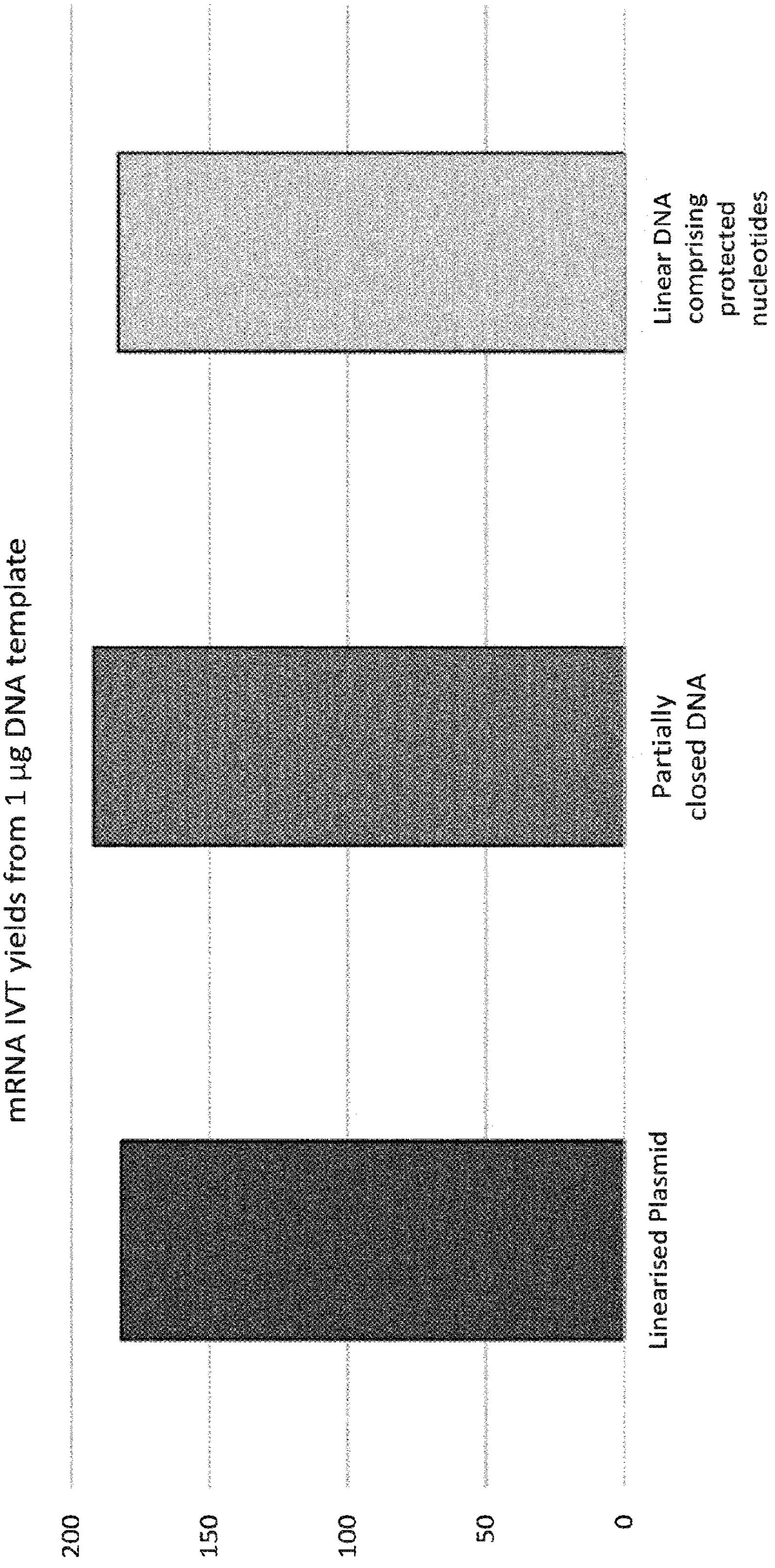
FIG. 25 illustrates yields generated from in vitro transcribed mRNA using T7 RNA polymerase and different DNA templates as in FIG. 22.

FIG. 25 illustrates yields generated from in vitro transcribed mRNA using T7 RNA polymerase and different DNA templates. Specifically, this Figure illustrates the impact of using partially closed linear DNA product (opDNA), linear DNA product comprising protected nucleotides (oeDNA) and linearized plasmid as in vitro transcription templates on mRNA yields. Traditional DNA linearized plasmid templates have been used for comparison. Reaction conditions: 1 μg of input DNA template was used per sample in a final reaction volume of 20 μL, 2 μL 10×T7-FlashScribe™ Transcription Buffer (CellScript), 10 mM NTPs (CellScript), 8 mM CleanCap AG (TriLink), 10 mM DTT (CellScript), 0.2 U inorganic pyrophosphatase (Thermo Scientific), 20 U ScriptGuard™ RNase Inhibitor, 2 μL T7-FlashScribe™ Enzyme Solution (CellScript). Incubation time and temperature: 2 hours at 37° C. A following DNase I treatment at 1 U was applied (CellScript), incubation time and temperature: 15 min at 37° C. mRNA yields measured using Qubit quantification (n=1) via Qubit RNA Broad Range kit (Invitrogen).

Shown in FIG. 25 are in vitro transcription mRNA yields obtained using different DNA templates, demonstrating the impact of using partially closed linear DNA product partially closed linear DNA product (opDNA), linear DNA product comprising protected nucleotides (oeDNA) and linearized plasmid as in vitro transcription templates on mRNA yields. A minimum yield of 180 μg was achieved from oeDNA templates, and a minimum yield of 190 μg was achieved from opDNA templates. Both partially closed linear DNA product (opDNA) and linear DNA product comprising protected nucleotides (oeDNA) produced comparable mRNA yields to traditional linearized plasmid. Reaction conditions: 1 μg of input DNA template was used per sample in a final reaction volume of 20 μL, 2 μL 10×T7-FlashScribe™ Transcription Buffer (CellScript), 10 mM NTPs (CellScript), 8 mM CleanCap AG (TriLink), 10 mM DTT (CellScript), 0.2 U inorganic pyrophosphatase (Thermo Scientific), 20 U ScriptGuard™ RNase Inhibitor, 2 μL T7-FlashScribe™ Enzyme Solution (CellScript). Incubation time and temperature: 2 hours at 37° C. A following DNase I treatment at 1 U was applied (CellScript), incubation time and temperature: 15 min at 37° C.

Figure 26:
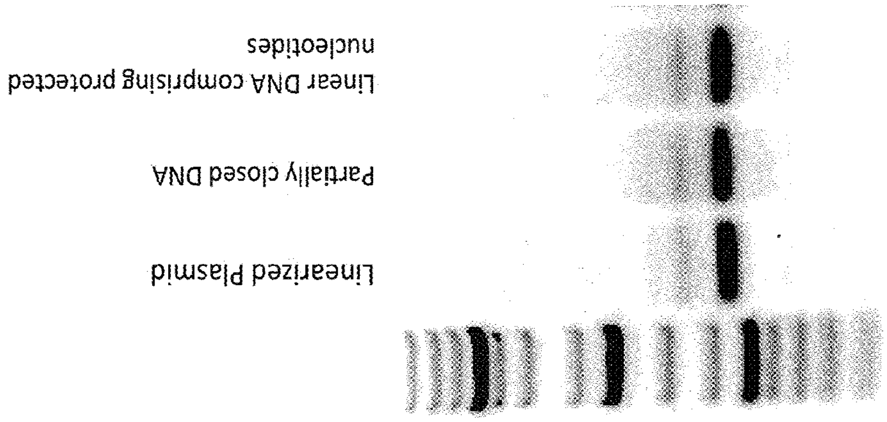
FIG. 26 illustrates in vitro transcribed mRNA samples imaged via native 0.8% agarose gel electrophoresis. mRNA samples were transcribed from DNA templates with different adapted ends.

FIG. 26 illustrates in vitro transcribed mRNA samples imaged via native 0.8% agarose gel electrophoresis. mRNA samples were transcribed from DNA templates with different adapted ends. Samples have been loaded to an equal mass of 1000 ng. mRNA derived from a traditional linearized plasmid has been loaded as a comparison.

Shown in FIG. 26 are in vitro transcribed mRNA samples imaged via native 0.8% agarose gel electrophoresis. mRNA samples were transcribed from DNA products with different adapted ends. The target band of ~0.75 kb can be observed across all samples. Independent of the adapted DNA template end, all samples produced similar band intensity and purity. A second higher molecular weight band can also be observed which corresponds to natural secondary structure folding of mRNA under native conditions.

Figure 27:
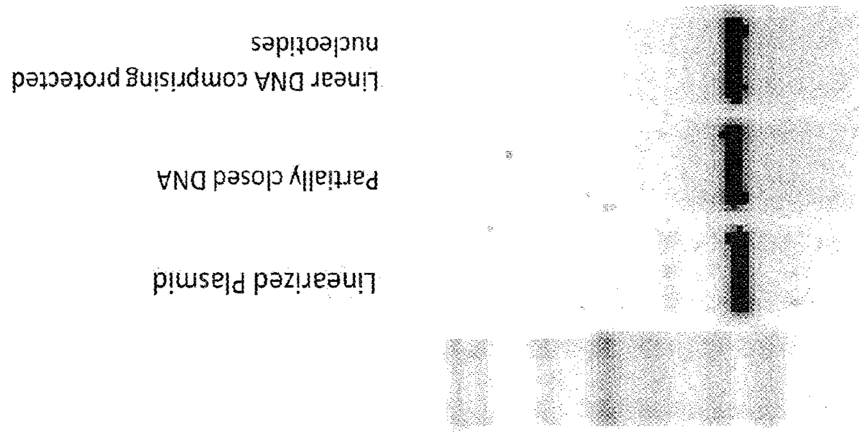
FIG. 27 illustrates in vitro transcribed mRNA samples imaged via denaturing 0.8% agarose gel electrophoresis. mRNA samples were transcribed from DNA templates with different adapted ends.

FIG. 27 illustrates in vitro transcribed mRNA samples imaged via denaturing 0.8% agarose gel electrophoresis. mRNA samples were transcribed from DNA products with different adapted ends. Samples have been loaded to an equal mass of 1000 ng. mRNA derived from a traditional linearized plasmids has been loaded as a comparison. All samples were heat denatured at 70° C. for 5 min and treated with formamide before addition to the gel.

Shown in FIG. 27 are in vitro transcribed mRNA samples imaged via denaturing 0.8% agarose gel electrophoresis. mRNA samples were transcribed from DNA products with different adapted ends. A main band of ~0.75 kb can be observed across all samples, demonstrating that partially closed linear DNA product and linear DNA product comprising protected nucleotides are suitable for transcription processes.

Figure 28:
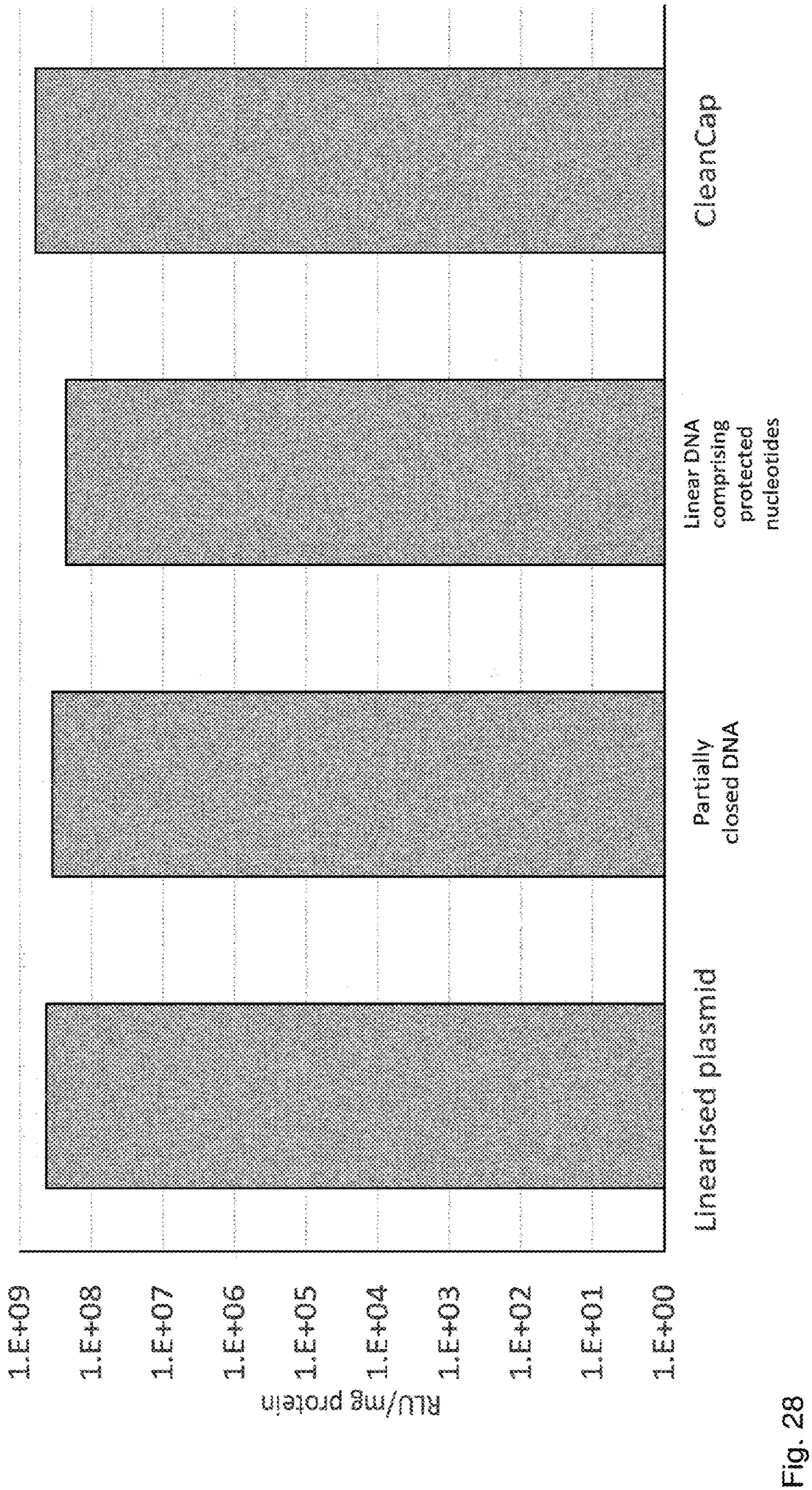
FIG. 28 shows luciferase expression in HEK293 cells transfected with commercially available transfection reagent, Lipofectamine2000 encapsulating mRNA derived from partially closed linear DNA product (opDNA) and linear DNA product comprising protected nucleotides (oeDNA).

FIG. 28 shows luciferase expression in HEK293 cells transfected with commercially available transfection reagent, Lipofectamine2000 encapsulating mRNA derived from partially closed linear DNA product and linear DNA product comprising protected nucleotides. Luciferase expression was measured 4 h post transfection. n-=3 in all experiments, error bars=SD. Linearised plasmid DNA template, and Trilink mRNA were used as positive controls.

Shown in FIG. 28 is Luciferase expression in HEK293 cells transfected with commercially available transfection reagent Lipofectamine2000, encapsulating mRNA derived from partially closed linear DNA product and linear DNA product comprising protected nucleotides. Linearised plasmid derived mRNA and Trilink mRNA were used as positive controls. Luciferase expression ranged between 2.25x10^8 and 6.05x10^8 RLU/mg protein, with equivalency between partially closed linear DNA product (opDNA) and linear DNA product comprising protected nucleotides (oeDNA)-derived mRNA, as compared to linearised plasmid.

Example 7—Transfection of HEK293 Cells—GFP mRNA

HEK293 cells were cultured in Dulbecco's Modified Eagle Medium (DMEM) (Gibco cat. no: 11965084) with 10% Fetal Bovine Serum (FBS) (Gibco, cat. no: 16140-071) and 1% Penicillin/Streptomycin (Gibco cat. no: 15070-063).

Transfections in HEK293 cells were performed with commercially available transfection reagents such as Lipofectamine2000 (ThermoFisher cat. no: 11668019).

Transfections were performed in a 96-well plate at a density of 25×103 cells per well seeded one day prior to transfection.

300 ng of GFP mRNA per well was diluted in 50 ul of OptiMEM while 0.5 ul of Lipofectamine2000 was diluted into 50 ul of OptiMEM. The components were incubated for 5 minutes separately then mixed thoroughly and incubated for a further 25 minutes before adding 100 ul OptiMEM to the wells. All conditions were performed in triplicate. Cells were incubated at 37° C. with 5% CO2. 4 h post-transfection, the cells were rinsed in PBS, before incubation in 0.05% Trypsin, 0.53 mM EDTA (Corning, cat no: 25-052-CV) to detach the cells. Cells were resuspended in PBS for analysis by flow cytometry using the Aligent Novocyte flow cytometer.

Figure 22:
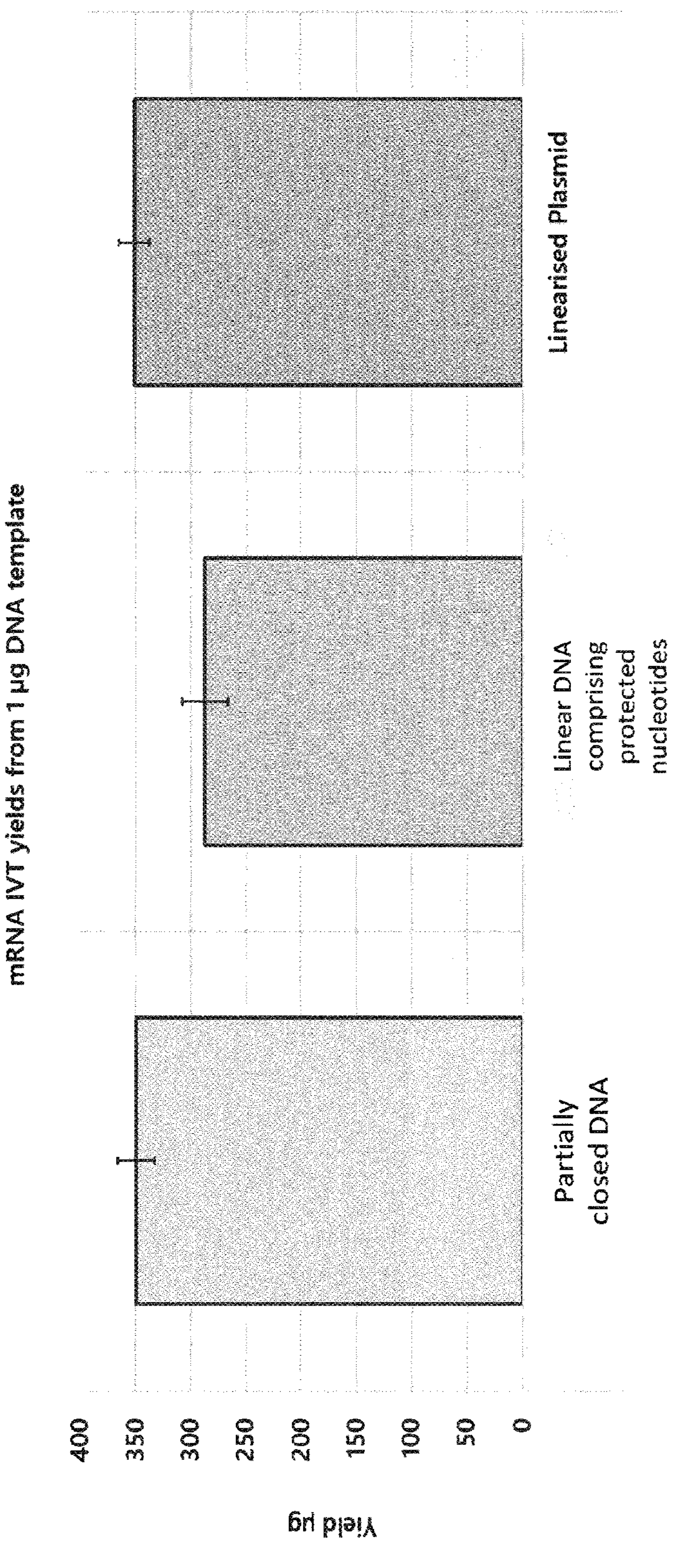
FIG. 22 illustrates yields generated from in vitro transcribed mRNA using T7 RNA polymerase and different DNA products described herein. opDNA-partially closed linear DNA product, oeDNA-linear DNA product comprising protected nucleotides.

FIG. 22 illustrates yields generated from in vitro transcribed mRNA using T7 RNA polymerase and different DNA templates. Specifically, this Figure illustrates the impact of using partially closed linear DNA product (opDNA) and linear DNA product comprising protected nucleotides (oeDNA) and linearized plasmid as in vitro transcription templates on mRNA yields. Traditional DNA linearized plasmid templates have been used for comparison. Reaction conditions: 1 μg of input DNA template was used per sample in a final reaction volume of 40 μL, 4 μL 10×T7-FlashScribe™ Transcription Buffer (CellScript), 10 mM NTPs (CellScript), 8 mM CleanCap AG (TriLink), 10 mM DTT (CellScript), 0.4 U inorganic pyrophosphatase (Thermo Scientific), 40 U ScriptGuard™ RNase Inhibitor, 4 μL T7-FlashScribe™ Enzyme Solution (CellScript). Incubation time and temperature: 2 hours at 37° C. A following DNase I treatment at 1 U was applied (CellScript), incubation time and temperature: 15 min at 37° C. mRNA yields measured using Qubit quantification (n=3) via Qubit RNA Broad Range kit (Invitrogen).

FIG. 22 shows in vitro transcription mRNA yields obtained using different DNA templates, demonstrating the impact of using partially closed linear DNA product (opDNA) and linear DNA product comprising protected nucleotides (oeDNA) and linearized plasmid as in vitro transcription templates on mRNA yields. A minimum yield of 280 μg was achieved from linear DNA product comprising protected nucleotides (oeDNA), and a minimum yield of 340 was achieved from partially closed linear DNA product (opDNA). Both forms of DNA products produced comparable mRNA yields to traditional linearized plasmid. Reaction conditions: 1 μg of input DNA template was used per sample in a final reaction volume of 40 μL, 4 μL 10×T7-FlashScribe™ Transcription Buffer (CellScript), 10 mM NTPs (CellScript), 8 mM CleanCap AG (TriLink), 10 mM DTT (CellScript), 0.4 U inorganic pyrophosphatase (Thermo Scientific), 40 U ScriptGuard™ RNase Inhibitor, 4 μL T7-FlashScribe™ Enzyme Solution (CellScript). Incubation time and temperature: 2 hours at 37° C. A following DNase I treatment at 1 U was applied (CellScript), incubation time and temperature: 15 min at 37° C.

Figure 23:
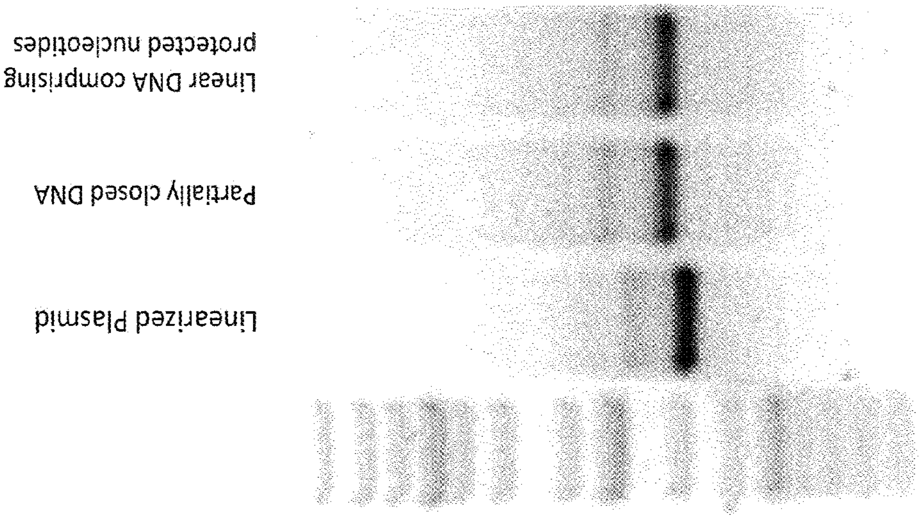
FIG. 23 illustrates in vitro transcribed mRNA samples of FIG. 22 imaged via native 0.8% agarose gel electrophoresis.

FIG. 23 illustrates in vitro transcribed mRNA samples imaged via native 0.8% agarose gel electrophoresis. mRNA samples were transcribed from DNA templates with different adapted ends. Samples have been loaded to an equal mass of 1000 ng. mRNA derived from a traditional linearized plasmid has been loaded as a comparison.

Shown in FIG. 23 are in vitro transcribed mRNA samples imaged via native 0.8% agarose gel electrophoresis. mRNA samples were transcribed from DNA templates with different adapted ends. The target band of ~2 kb can be observed across all samples. Independent of the adapted DNA template end, all samples produced similar band intensity and purity. A second higher molecular weight band can also be observed which corresponds to natural secondary structure folding of mRNA under native conditions.

Figure 24:
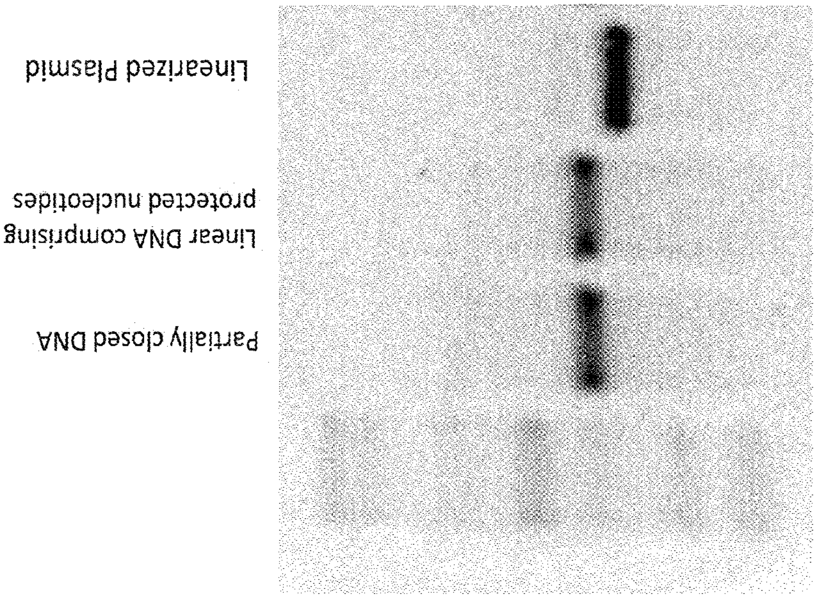
FIG. 24 illustrates in vitro transcribed mRNA samples of FIG. 21 imaged via denaturing 0.8% agarose gel electrophoresis.

FIG. 24 illustrates in vitro transcribed mRNA samples imaged via denaturing 0.8% agarose gel electrophoresis. mRNA samples were transcribed from DNA templates with different adapted ends. Samples have been loaded to an equal mass of 1000 ng. mRNA derived from a traditional linearized plasmids has been loaded as a comparison. All samples were heat denatured at 70° C. for 5 min and treated with formamide before addition to the gel.

Shown in FIG. 24 are in vitro transcribed mRNA samples imaged via denaturing 0.8% agarose gel electrophoresis. mRNA samples were transcribed from DNA templates with different adapted ends. A main band of ~2 kb can be observed across all samples, demonstrating that partially closed linear DNA product (opDNA) and linear DNA product comprising protected nucleotides (oeDNA) are suitable for transcription processes.

Figure 29:
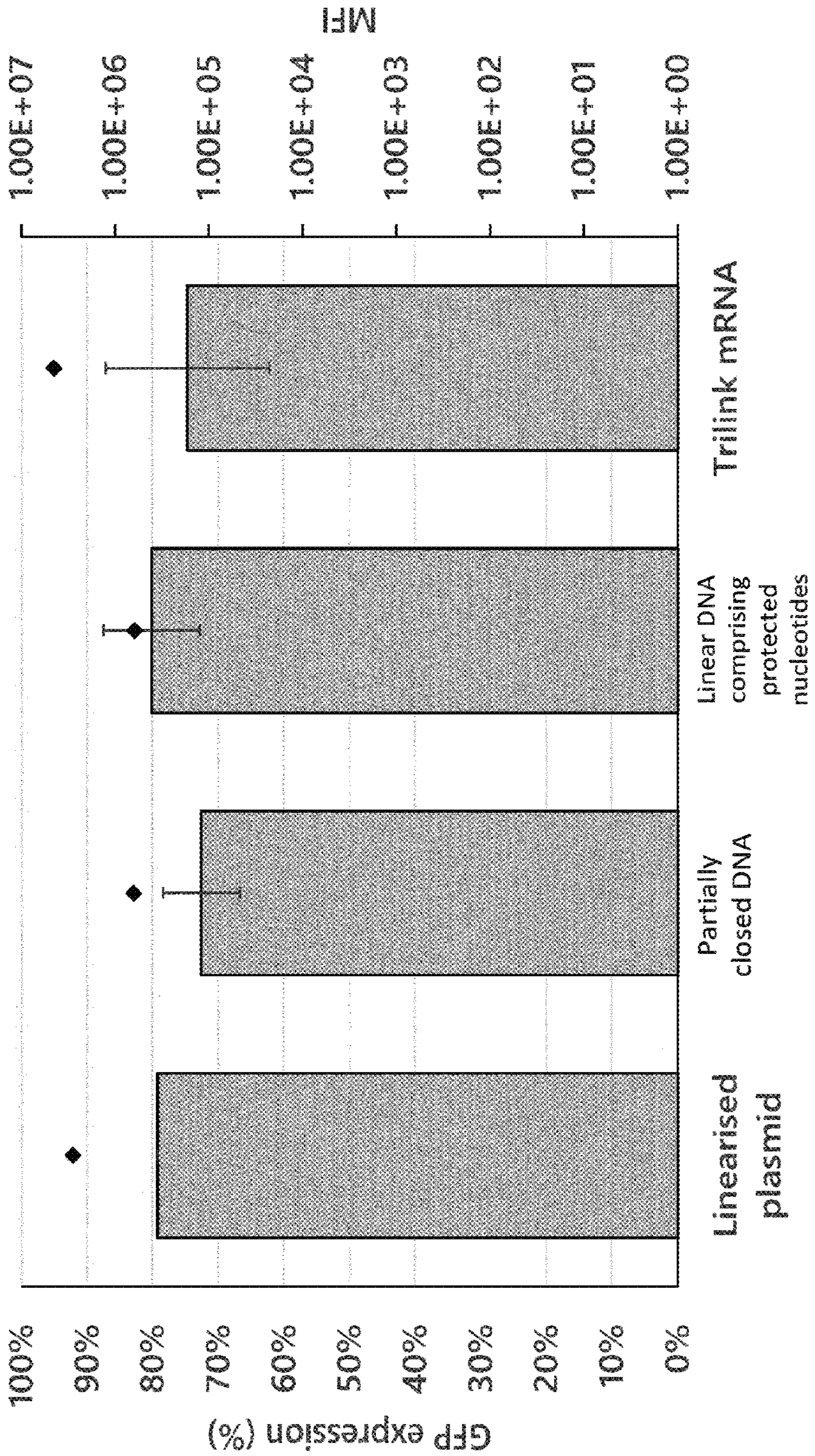
FIG. 29 shows GFP expression in HEK293 cells transfected with commercially available transfection reagent, Lipofectamine2000 encapsulating mRNA derived from partially closed linear DNA product (opDNA) and linear DNA product comprising protected nucleotides (oeDNA).

FIG. 29 shows GFP expression in HEK293 cells transfected with commercially available transfection reagent, Lipofectamine2000 encapsulating mRNA derived from partially closed linear DNA product (opDNA) and linear DNA product comprising protected nucleotides (oeDNA). GFP expression was measured 4 h post transfection. n-=3 in all experiments, error bars=SD. Linearised plasmid DNA template, and Trilink mRNA were used as positive controls.

Shown in FIG. 29 is GFP expression in HEK293 cells transfected with commercially available transfection reagent, Lipofectamine2000 encapsulating mRNA derived from partially closed linear DNA product (opDNA) and linear DNA product comprising protected nucleotides (oeDNA). Linearised plasmid DNA template, and Trilink mRNA were used as positive controls. GFP expression was above 70% across all mRNA, with equivalency between partially closed linear DNA product (opDNA) and linear DNA product comprising protected nucleotides (oeDNA)-derived mRNA, as compared to linearised plasmid.

Example 8—Transfection of HEK Cells—Luciferase Closed Linear DNA (hpDNA) Vs Linear DNA Product Comprising Protected Nucleotides (oeDNA)

HEK293 cells were cultured in Dulbecco's Modified Eagle Medium (DMEM) (Gibco cat. no: 11965084) with 10% Fetal Bovine Serum (FBS) (Gibco, cat. no: 16140-071) and 1% Penicillin/Streptomycin (Gibco cat. no: 15070-063).

Transfections in HEK293 cells were performed with commercially available transfection reagent Lipofectamine2000 (ThermoFisher cat. no: 11668019).

Transfections were performed in a 96-well plate at a density of 25×103 cells per well seeded one day prior to transfection.

300 ng of closed linear DNA productor linear DNA product comprising protected nucleotides per well diluted in 50 ul of OptiMEM while 0.5 ul of Lipofectamine2000 was diluted into 50 ul of OptiMEM. The components were incubated for 5 minutes separately then mixed thoroughly and incubated for a further 25 minutes before adding 100 ul OptiMEM to the wells.

All conditions were performed in triplicate. Cells were incubated at 37° C. with 5% CO2. 48 hours post-transfection, the cells were rinsed in PBS, before resuspension in Reporter Lysis buffer (Promega). Plates were incubated at 4° C. for 20 minutes, before −80° C. for 40 minutes. After thawing, luciferase activity was measured following injection of the luciferase assay substrate on the ClarioSTAR plus plate reader (BMG Labtech, Aylesbury, UK). Luciferase expression was normalised to protein content using Pierce BCA Protein Assay, with absorbance measured at 562 nm. Luciferase activity was expressed as Relative Light Units per mg of protein (RLU/mg).

Figure 30:
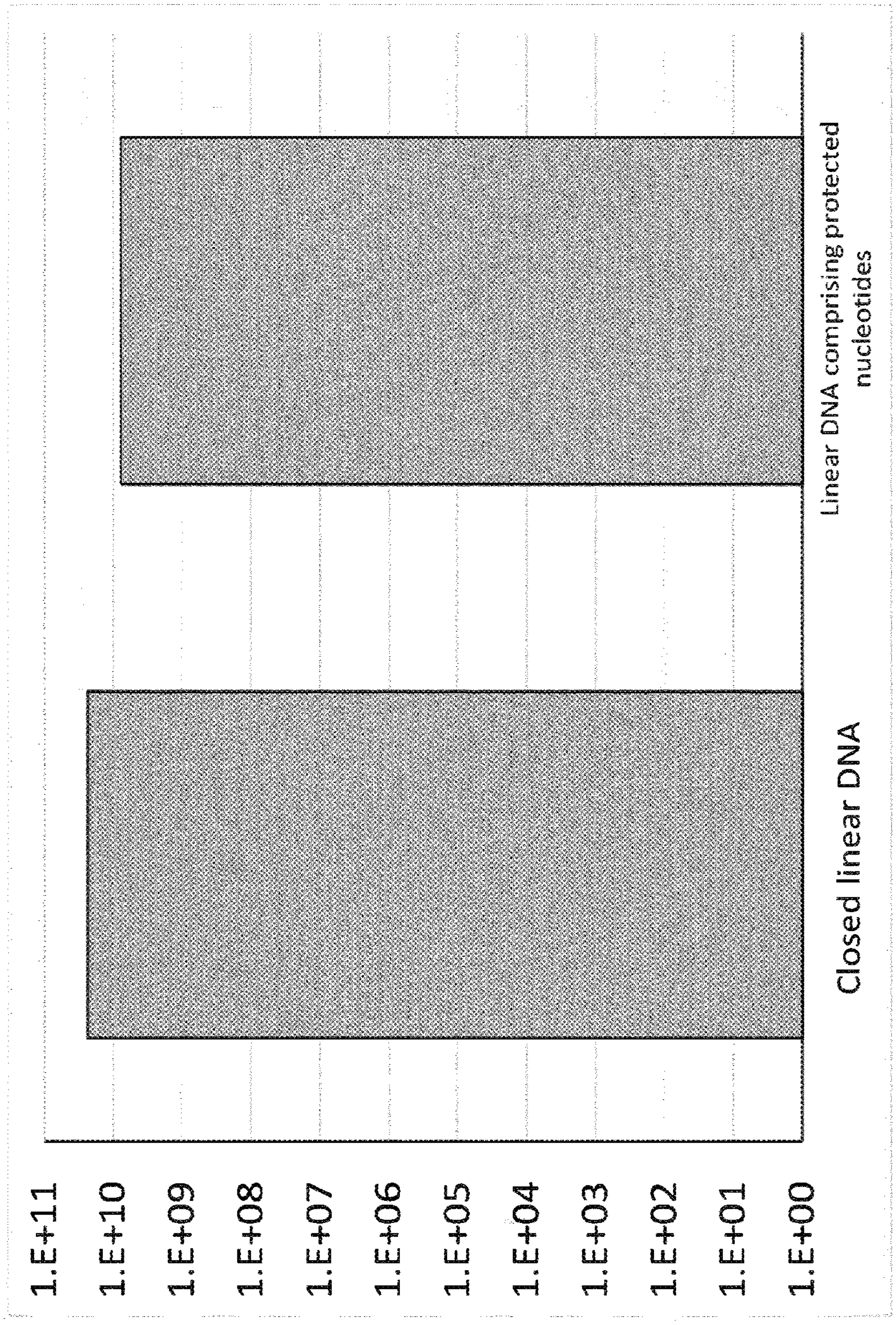
FIG. 30 shows Luciferase expression in HEK293 cells transfected with commercially available transfection reagent, Lipofectamine2000 encapsulating closed linear DNA (hpDNA) or linear DNA product comprising protected nucleotides (oeDNA) encoding Luciferase reporter gene The sequences discussed in the application are provided in the table below.

FIG. 30 shows Luciferase expression in HEK293 cells transfected with commercially available transfection reagent, Lipofectamine2000 encapsulating closed linear DNA product (hpDNA) or linear DNA product comprising protected nucleotides (oeDNA) encoding Luciferase reporter gene. GFP expression was measured 48 h post transfection. n=3 in all experiments, error bars=SD.

Shown in FIG. 30 is Luciferase expression in HEK293 cells transfected with commercially available transfection reagent, Lipofectamine2000, encapsulating closed linear DNA product (hpDNA) or linear DNA product comprising protected nucleotides (oeDNA) encoding Luciferase reporter gene. Luciferase expression was 3.85E+10 for oeDNA vs 1.20E+11 for hpDNA, showing high Luciferase expression irrespective of linear DNA product.

The invention claimed is:

1. A partially closed linear DNA product comprising a double-stranded DNA portion that is closed at a first end and open at a second end, wherein the partially closed linear DNA product comprises: (i) a cassette, wherein the cassette comprises a sense strand and an antisense strand and wherein the cassette comprises a coding sequence; and (ii) one or more nuclease-resistant nucleotides in an open-end region adjacent to the second end.

2. The partially closed linear DNA product of claim 1, wherein the open-end region adjacent to the second end comprises a sense strand and an antisense strand and wherein the open-end region adjacent to the second end comprises one or more nuclease-resistant nucleotides in the sense strand or the antisense strand.

3. The partially closed linear DNA product of claim 1, wherein the open-end region adjacent to the second end comprises a sense strand and an antisense strand and wherein the open-end region adjacent to the second end comprises one or more nuclease-resistant nucleotides in both the sense strand and the antisense strand.

4. The partially closed linear DNA product of claim 1, wherein the nuclease-resistant nucleotides are phosphorothioated nucleotides.

5. The partially closed linear DNA product of claim 1, wherein the open-end region is 3' of the sense strand of the cassette.

6. The partially closed linear DNA product of claim 1, wherein the open-end region is 5' of the sense strand of the cassette.

7. The partially closed linear DNA product of claim 1, wherein the cassette further comprises a promoter.

8. The partially closed linear DNA product of claim 1, wherein the cassette further comprises a promoter, a ribosomal binding site and a translational termination sequence.

9. The partially closed linear DNA product of claim 1, wherein the cassette comprises a homopolymeric sequence.

10. The partially closed linear DNA product of claim 1, wherein the partially closed linear DNA product comprises a spacer.

11. The partially closed linear DNA product of claim 1, wherein the partially closed linear DNA product encodes a sequence of a therapeutic protein, a part of a vaccine, or an element of a genetic engineering mechanism.

12. The partially closed linear DNA product of claim 1, wherein the partially closed linear DNA product comprises a gene sequence encoding a nuclease protein of a CRISPR system and/or a guide RNA.

13. The partially closed linear DNA product of claim 12, wherein the nuclease protein of a CRISPR system is Cas9, Cpf1, or MAD7.

14. The partially closed linear DNA product of claim 9, wherein the homopolymeric sequence is a polyA, polyC, polyT or polyG sequence.

15. The partially closed linear DNA product of claim 9, wherein the homopolymeric sequence is at least 120 nucleotides in length.

16. The partially closed linear DNA product of claim 9, wherein the homopolymeric sequence is between 3-200 nucleotides in length.

17. The partially closed linear DNA product of claim 10, wherein the spacer is at least 20 base pairs long.

* * * * *

SEQUENCE LISTING

```
Sequence total quantity: 25
SEQ ID NO: 1            moltype = DNA  length = 20
FEATURE                 Location/Qualifiers
source                  1..20
                        mol_type = other DNA
                        organism = synthetic construct
SEQUENCE: 1
agggctaaca tttgttggcc                                                  20

SEQ ID NO: 2            moltype = DNA  length = 16
FEATURE                 Location/Qualifiers
source                  1..16
                        mol_type = other DNA
                        organism = synthetic construct
SEQUENCE: 2
ggccaacaaa tgttag                                                      16

SEQ ID NO: 3            moltype = DNA  length = 34
```

```
FEATURE                Location/Qualifiers
source                 1..34
                       mol_type = other DNA
                       organism = Bacteriophage P1
SEQUENCE: 3
ataacttcgt ataatgtatg ctatacgaag ttat                              34

SEQ ID NO: 4           moltype = DNA  length = 41
FEATURE                Location/Qualifiers
source                 1..41
                       mol_type = other DNA
                       organism = synthetic construct
misc_feature           1
                       standard_name = 5' phosphate
SEQUENCE: 4
agggctaaca tttgttggcc actcaggcca acaaatgtta g                      41

SEQ ID NO: 5           moltype = DNA  length = 16
FEATURE                Location/Qualifiers
source                 1..16
                       mol_type = other DNA
                       organism = synthetic construct
misc_feature           1
                       standard_name = 5' phosphate
SEQUENCE: 5
ggccaacaaa tgttag                                                  16

SEQ ID NO: 6           moltype = DNA  length = 20
FEATURE                Location/Qualifiers
source                 1..20
                       mol_type = other DNA
                       organism = synthetic construct
misc_feature           1
                       standard_name = 5' phosphate
SEQUENCE: 6
agggctaaca tttgttggcc                                              20

SEQ ID NO: 7           moltype = DNA  length = 203
FEATURE                Location/Qualifiers
source                 1..203
                       mol_type = other DNA
                       organism = Human cytomegalovirus
SEQUENCE: 7
tgatgcggtt ttggcagtac atcaatgggc gtggatagcg gtttgactca cggggatttc  60
caagtctcca ccccattgac gtcaatggga gtttgttttg gcaccaaaat caacgggact  120
ttccaaaatg tcgtaacaac tccgccccat tgacgcaaat gggcggtagg cgtgtacggt  180
gggaggtcta tataagcaga gct                                          203

SEQ ID NO: 8           moltype = DNA  length = 304
FEATURE                Location/Qualifiers
source                 1..304
                       mol_type = other DNA
                       organism = Human cytomegalovirus
SEQUENCE: 8
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catg                                                               304

SEQ ID NO: 9           moltype = DNA  length = 720
FEATURE                Location/Qualifiers
source                 1..720
                       mol_type = genomic DNA
                       organism = Aequorea victoria
SEQUENCE: 9
atggtcagca agggcgagga actgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgtacc accggcaagc tgcccgtgcc ctggcccacc  180
ctcgtgacca ccctgaccta cggcgtgcaa tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcaactcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtag  720
```

```
SEQ ID NO: 10          moltype = DNA  length = 122
FEATURE                Location/Qualifiers
source                 1..122
                       mol_type = genomic DNA
                       organism = Simian virus 40
SEQUENCE: 10
taagatacat tgatgagttt ggacaaacca caactagaat gcagtgaaaa aaatgcttta  60
tttgtgaaat ttgtgatgct attgctttat ttgtaaccat tataagctgc aataaacaag  120
tt                                                                 122

SEQ ID NO: 11          moltype = DNA  length = 139
FEATURE                Location/Qualifiers
source                 1..139
                       mol_type = genomic DNA
                       organism = Adeno-associated virus 2
SEQUENCE: 11
tgcaggcagc tgcgcgctcg ctcgctcact gaggccgccc gggcaaagcc cgggcgtcgg  60
gcgacctttg gtcgcccggc ctcagtgagc gagcgagcgc gcagagaggg agtggccaac  120
tccatcacta ggggttcct                                               139

SEQ ID NO: 12          moltype = DNA  length = 1653
FEATURE                Location/Qualifiers
source                 1..1653
                       mol_type = genomic DNA
                       organism = Photinus pyralis
SEQUENCE: 12
atggaagacg ccaaaaacat aaagaaaggc ccggcgccat tctatccgct ggaagatgga  60
accgctggag agcaactgca taaggctatg aagagatacg ccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgggcatt  360
tcgcagccta ccgtggtgtt cgtttccaaa aaggggttgc aaaaaatttt gaacgtgcaa  420
aaaaagctcc caatcatcca aaaaattatt atcatggatt ctaaaacgga ttaccaggga  480
tttcagtcga tgtacacgtt cgtcacatct catctacctc ccggttttaa tgaatacgat  540
tttgtgccag agtccttcga tagggacaag acaattgcac tgatcatgaa ctcctctgga  600
tctactggtc tgcctaaagg tgtcgctctg cctcatagaa ctgcctgcgt gagattctcg  660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttc tgaggagcct tcaggattac  840
aagattcaaa gtgcgctgct ggtgccaacc ctattctcct tcttcgccaa aagcactctg  900
attgacaaat acgatttatc taatttacac gaaattgctt ctggtggcgc tcccctctct  960
aaggaagtcg gggaagcggt tgccaagagg ttccatctgc caggtatcag gcaaggatat  1020
gggctcactg agactacatc agctattctg attacacccg agggggatga taaaccgggc  1080
gcggtcggta aagttgttcc atttttttgaa gcgaaggttg tggatctgga taccgggaaa  1140
acgctgggcg ttaatcaaag aggcgaactg tgtgtgagag gtcctatgat tatgtccggt  1200
tatgtaaaca atccggaagc gaccaacgcc ttgattgaca aggatggatg gctacattct  1260
ggagacatag cttactggga cgaagacgaa cacttcttca tcgttgaccg cctgaagtct  1320
ctgattaagt acaaaggcta tcaggtggct cccgctgaat tggaatccat cttgctccaa  1380
caccccaaca tcttcgacgc aggtgtcgca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg gaggagttgt gtttgtggac  1560
gaagtaccga aaggtcttac cggaaaactc gacgcaagaa aaatcagaga gatcctcata  1620
aaggccaaga agggcggaaa gatcgccgtg taa                                 1653

SEQ ID NO: 13          moltype = DNA  length = 18
FEATURE                Location/Qualifiers
source                 1..18
                       mol_type = other DNA
                       organism = synthetic construct
modified_base          11..15
                       mod_base = OTHER
                       note = phosphorothioated
SEQUENCE: 13
aaaaaaaaaa aaaaaaaa                                                18

SEQ ID NO: 14          moltype = DNA  length = 14
FEATURE                Location/Qualifiers
source                 1..14
                       mol_type = other DNA
                       organism = synthetic construct
modified_base          1..5
                       mod_base = OTHER
                       note = phosphorothioated
SEQUENCE: 14
tttttttttt tttt                                                    14

SEQ ID NO: 15          moltype = DNA  length = 47
```

-continued

```
FEATURE                Location/Qualifiers
source                 1..47
                       mol_type = other DNA
                       organism = synthetic construct
SEQUENCE: 15
nagggctaac atttgttggc cactcaggcc aacaaatgtt agccctn              47

SEQ ID NO: 16          moltype = DNA  length = 19
FEATURE                Location/Qualifiers
source                 1..19
                       mol_type = other DNA
                       organism = synthetic construct
modified_base          15..19
                       mod_base = OTHER
                       note = phosphorothioated
SEQUENCE: 16
aaaaaaaaaa aaaaaaaaa                                             19

SEQ ID NO: 17          moltype = DNA  length = 19
FEATURE                Location/Qualifiers
source                 1..19
                       mol_type = other DNA
                       organism = synthetic construct
modified_base          1..5
                       mod_base = OTHER
                       note = phosphorothioated
SEQUENCE: 17
tttttttttt ttttttttt                                             19

SEQ ID NO: 18          moltype = DNA  length = 12
FEATURE                Location/Qualifiers
source                 1..12
                       mol_type = other DNA
                       organism = synthetic construct
SEQUENCE: 18
ggtctcgccc tn                                                    12

SEQ ID NO: 19          moltype = DNA  length = 12
FEATURE                Location/Qualifiers
source                 1..12
                       mol_type = other DNA
                       organism = synthetic construct
SEQUENCE: 19
nagggcgaga cc                                                    12

SEQ ID NO: 20          moltype = DNA  length = 12
FEATURE                Location/Qualifiers
source                 1..12
                       mol_type = other DNA
                       organism = synthetic construct
SEQUENCE: 20
aaaaacgaga cc                                                    12

SEQ ID NO: 21          moltype = DNA  length = 12
FEATURE                Location/Qualifiers
source                 1..12
                       mol_type = other DNA
                       organism = synthetic construct
SEQUENCE: 21
ggtctcgttt tt                                                    12

SEQ ID NO: 22          moltype = DNA  length = 21
FEATURE                Location/Qualifiers
source                 1..21
                       mol_type = other DNA
                       organism = synthetic construct
modified_base          1..5
                       mod_base = OTHER
                       note = phosphorothioated
SEQUENCE: 22
ggccaacaaa tgttagccct n                                          21

SEQ ID NO: 23          moltype = DNA  length = 21
FEATURE                Location/Qualifiers
source                 1..21
                       mol_type = other DNA
                       organism = synthetic construct
modified_base          17..21
                       mod_base = OTHER
```

-continued

```
                         note = phosphorothioated
SEQUENCE: 23
nagggctaac atttgttggc c                                            21

SEQ ID NO: 24            moltype = DNA  length = 1653
FEATURE                  Location/Qualifiers
source                   1..1653
                         mol_type = other DNA
                         organism = synthetic construct
SEQUENCE: 24
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgaatactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagtcc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg taa                               1653

SEQ ID NO: 25            moltype = DNA  length = 720
FEATURE                  Location/Qualifiers
source                   1..720
                         mol_type = other DNA
                         organism = synthetic construct
SEQUENCE: 25
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720
```